US006589962B1

(12) United States Patent
Tata et al.

(10) Patent No.: US 6,589,962 B1
(45) Date of Patent: Jul. 8, 2003

(54) ALPHA-HYDROXY-GAMMA-[[(CARBOCYCLIC-OR HETEROCYCLIC-SUBSTITUTED)AMINO]CARBONYL] ALKANAMIDE DERIVATIVES AND USES THEREOF

(75) Inventors: James R Tata, Westfield, NJ (US); Zhijian Lu, Clinton, NJ (US); Subharekha Raghavan, Teaneck, NJ (US); Tracy T. Huening, Madison, NJ (US); Thomas A. Rano, Somerville, NJ (US); Mark G. Charest, Cambridge, MA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/031,513

(22) Filed: Apr. 16, 2002

Related U.S. Application Data

(60) Provisional application No. 60/144,644, filed on Jul. 20, 1999, and provisional application No. 60/147,226, filed on Aug. 4, 1999.

(51) Int. Cl.$^7$ .................. A01N 43/16; A01N 43/36; A01N 43/40; A01N 43/42; A01N 43/76
(52) U.S. Cl. .................. 514/299; 514/337; 514/342; 514/365; 514/374; 514/422; 514/423; 514/456; 546/115; 546/269.7; 546/279.1; 548/200; 548/215; 548/525; 548/537; 549/399
(58) Field of Search .................. 514/299, 337, 514/342, 365, 374, 422, 423, 456; 546/114, 269.7, 279.1; 548/200, 215, 525, 537; 549/399

(56) References Cited

U.S. PATENT DOCUMENTS

| 5,196,438 A | 3/1993 | Martin et al. |
| 5,413,999 A | 5/1995 | Vacca et al. |
| 5,484,801 A | 1/1996 | Al-Razzak et al. |
| 5,484,926 A | 1/1996 | Dressman et al. |
| 5,644,028 A | 7/1997 | Mimoto et al. |
| 5,646,148 A | 7/1997 | Huff et al. |
| 5,948,811 A | 9/1999 | Chan et al. |
| 5,962,640 A | 10/1999 | Kato et al. |

FOREIGN PATENT DOCUMENTS

| EP | 0 534 511 | 3/1993 |
| EP | 0 706 794 | 4/1996 |
| EP | 0 751 145 | 1/1997 |
| GB | 2 288 801 | 11/1995 |

OTHER PUBLICATIONS

N. E. Koh et al., "Active human immunodeficiency virus protease is required for viral infectivity", Proc. Natl. Acad. Sci. vol. 85, pp. 4686–4690 (Jul. 1988).

L. Ratner et al., "Complete nucleotide sequence of the AIDS virus, HTLV–VIII", Nature, vol. 313, pp. 277–284 (Jan. 1985).

H. Toh et al., "Close structural resemblance between putative polymerase of a Drosophila transposable genetic element 17.6 and pol gene product of Moloney murine leukaemia virus", The EMBO Journal, vol. 4, No. 5, pp. 1267–1272 (1985).

M. D. Power et al., "Nucleotide sequence of SRV–1, a type D Simian Acquired Immune Deficiency Syndrome Retrovirus", Science, vol. 231, pp. 1567–1572 (Mar. 1986).

L. H. Pearl et al., "A structural model for the retroviral proteases", Nature, vol. 329, pp. 351–354 (Sep. 1987).

S. M. Hammer et al., "A Controlled Trial of Two Nucleoside Analogues plus Indinavir in Persons with Human Immunodeficiency Virus Infection and CD4 Cell Counts of 200 per Cubic Millimeter or Less", The New England J. Med., vol. 337, No. 11, pp. 725–733 (Sep. 1997).

R. M. Gulick et al., "Treatment with Indinavir, Zidovudine, and Lamivudine in Adults with Human Immunodeficiency Virus Infection and Prior Antiretroviral Therapy", The New England J. Med., vol. 337, No. 11, pp. 734–739 (Sep. 1997).

J. H. Condra, "Virological and clinical implications of resistance to HIV–1 protease inhibitors", Drugs Resistance Updates, vol. 1, pp. 1–7 (1998).

J. H. Condra et al., "In vivo emergence of HIV–1 variants resistant to multiple protease inhibitors", Nature, vol. 374, pp. 569–571 (Apr. 1995).

J. H. Condra et al., "Genetic Correlates of In Vivo Viral Resistance to Indinavir, a Human Immunodeficiency Virus Type 1 Protease Inhibitor", J. of Virology, vol. 70, No. 12, pp. 8270–8276 (Dec. 1996).

M. Tisdale et al., "Cross–Resistance Analysis of Human Immunodeficiency Virus Type 1 Variants Individually Selected for Resistance to Five Different Protease Inhibitors", Antimicrob. Agents and Chemotherapy, Vo. 39, No. 8, pp. 1704–1710 (Aug. 1995).

A. K. Patick et al., "Genotypic and phenotypic characterization of HIV–1 variants isolated from in vitro selection studies and from patients treated with the protease inhibitor, nelfinavir", Antiviral Therapy, vol. 1, Supp. 1, Abstract 29, pp. 17–18 (1996).

T. Mimoto et al., "Structure—Activity Relationship of Small–sized HIV Protease Inhibitors Containing Allophenylnorstatine", J. Med. Chem., vol. 42, pp. 1789–1802 (1999).

(List continued on next page.)

Primary Examiner—Brian Davis
(74) Attorney, Agent, or Firm—Kenneth R. Walton; Melvin Winokur

(57) ABSTRACT

Certain α-hydroxy-γ-[[(carbocyclic- or heterocyclic-substituted)amino]carbonyl]alkanamide derivatives are described as inhibitors of HIV protease and inhibitors of HIV replication. These compounds are useful in the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described. These compounds are effective against HIV viral mutants which are resistant to HIV protease inhibitors currently used for treating AIDS and HIV infection.

45 Claims, No Drawings

OTHER PUBLICATIONS

E. Takashiro et al., "Structure–Activity Relationship of HIV–1 Protease Inhibitors Containing alpha–Hydroxy–beta–Amino Acids. Detailed Study of P1 Site", Bioorganic and Medicinal Chemistry, vol. 7, pp. 2063–2072 (1999).

T. Punniyamurthy et al., "Polyaniline Supported Cobalt(II) Salen Catalysed Synthesis of Pyrrolidine Containing alpha–Hydroxyamide Core Structures as Inhibitors for HIV Proteases", Tetrahedron Letters, vol. 38, No. 25, pp. 4463–4466 (1997).

ALPHA-HYDROXY-GAMMA-[[(CARBOCYCLIC-OR HETEROCYCLIC-SUBSTITUTED)AMINO]CARBONYL] ALKANAMIDE DERIVATIVES AND USES THEREOF

This application is a 371 of PCT 4500/19626 Jul. 19, 2000 which claims Benefit of 60/144,644 filed Jul. 20, 1999 which claims benefit of 60/147,226 filed Aug. 4, 1999.

FIELD OF THE INVENTION

The present invention is directed to α-hydroxy-γ-[[(carbocyclic- or heterocyclic-substituted)amino]carbonyl] alkanamide derivatives, their pharmaceutically acceptable salts, their synthesis, and their use as inhibitors of HIV protease. The compounds of the present invention are useful for preventing or treating infection by HIV and for treating AIDS.

References are made throughout this application to various publications in order to more fully describe the state of the art to which this invention pertains. The disclosures of these references are hereby incorporated by reference in their entireties.

BACKGROUND OF THE INVENTION

A retrovirus designated human immunodeficiency virus (HIV) is the etiological agent of the complex disease that includes progressive destriction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al., *Proc. Nat'l Acad. Sci.* 1988, 85: 4686, demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, an endonuclease and an HIV protease [Toh et al., *EMBO J.* 1985, 4: 1267; Power et al., *Science* 1986, 231: 1567; Pearl et al., *Nature* 1987, 329: 351].

Several HIV protease inhibitors are presently in clinical use for the treatment of AIDS and HIV infection, including indinavir (see U.S. Pat. No. 5,413,999), nelfinavir (U.S. Pat. No. 5,484,926), saquinavir (U.S. Pat. No. 5,196,438), and ritonavir (U.S. Pat. No. 5,484,801). Each of these protease inhibitors is a peptidomimetic, competitive inhibitor of the viral protease which prevents cleavage of the HIV gag-pol polyprotein precursor. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 1997, 337: 725–733 and Gulick et al., *New England J. Med.* 1997, 337: 734–739.

A substantial and persistent problem in the treatment of AIDS has been the ability of the HIV virus to develop resistance to the therapeutic agents employed to treat the disease. Resistance to HIV-1 protease inhibitors has been associated with 25 or more amino acid substitutions in both the protease and the cleavage sites. Many of these viral variants are resistant to all of the HIV protease inhibitors currently in clinical use. See Condra et al., *Drug Resistance Updates* 1998, 1: 1–7; Condra et al., *Nature* 1995, 374: 569–571; Condra et al., *J. Virol.* 1996, 70: 8270–8276; Patrick et al., *Antiviral Ther.* 1996, Suppl. 1: 17–18; and Tisdale et al., *Antimicrob. Agents Chemother.* 1995, 39: 1704–1710.

Attempts to address the resistance issue with "salvage therapy" consisting of high doses of multiple protease inhibitors have only been moderately successful due to the high level of cross resistance and toxicities associated with these protease inhibitors. Accordingly, there remains a need for new protease inhibitors having improved effectiveness against the viral variants.

The present invention is directed to novel protease inhibitors which are much more potent against HIV viral mutants than the known protease inhibitors.

SUMMARY OF THE INVENTION

The present invention provides a novel group of α-hydroxy-γ-[[(carbocyclic- or heterocyclic-substituted) amino]carbonyl]alkanamide derivatives which are potent inhibitors of HIV protease including mutant forms thereof that are resistant to known protease inhibitors. These compounds are useful in the inhibition of HIV protease, the prevention of infection by HIV, the treatment of infection by HIV and in the treatment of AIDS and/or ARC, when employed as compounds or pharmaceutically acceptable salts or hydrates (when appropriate) thereof, optionally as pharmaceutical composition ingredients, and optionally in combination with other antivirals, anti-infectives, immunomodulators, antibiotics or vaccines. More particularly, the present invention includes a compound of Formula (I):

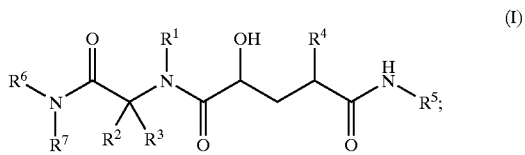

wherein
$R^1$, $R^2$, and $R^3$ are as defined in (A) or in (B) as follows:
(A) $R^1$ is
1) hydrogen,
2) $C_1–C_6$ alkyl, or
3) substituted $C_1–C_6$ alkyl wherein each substituent is independently selected from
   a) halo,
   b) hydroxy,
   c) $C_1–C_3$ alkoxy,
   d) aryl,
   e) substituted aryl, wherein each substituent is independently selected from halo, hydroxy, $C_1–C_4$ alkyl, fluorinated $C_1–C_4$ alkyl, and aryl,
   f) heterocycle, and
   g) substituted heterocycle, wherein each substituent is independently selected from halo, hydroxy, $C_1–C_4$ alkyl, fluorinated $C_1–C_4$ alkyl, and aryl;

$R^2$ and $R^3$ are each independently selected from
1) hydrogen,
2) $C_1$–$C_6$ alkyl,
3) substituted $C_1$–$C_6$ alkyl wherein each substituent is independently selected from
   a) halo,
   b) hydroxy,
   c) $C_1$–$C_3$ alkoxy,
   d) aryl,
   e) substituted aryl, wherein each substituent is independently selected from cyano, halo, hydroxy, $C_1$–$C_4$ alkyl, fluorinated $C_1$–$C_4$ alkyl, and aryl,
   f) heterocycle, and
   g) substituted heterocycle, wherein each substituent is independently selected from cyano, halo, hydroxy, $C_1$–$C_4$ alkyl, fluorinated $C_1$–$C_4$ alkyl, and aryl,
4) aryl,
5) substituted aryl wherein each substituent is independently selected from
   a) halo,
   b) hydroxy,
   c) $C_1$–$C_3$ alkoxy,
   d) aryl,
   e) substituted aryl wherein each substituent is independently selected from cyano, halo, hydroxy, $C_1$–$C_4$ alkyl, and fluorinated $C_1$–$C_4$ alkyl,
   f) heterocycle,
   g) substituted heterocycle wherein each substituent is independently selected from cyano, halo, hydroxy, $C_1$–$C_4$ alkyl, and fluorinated $C_1$–$C_4$ alkyl,
6) heterocycle, and
7) substituted heterocycle wherein each substituent is independently selected from
   a) halo,
   b) hydroxy,
   c) $C_1$–$C_3$ alkoxy,
   d) aryl,
   e) substituted aryl wherein each substituent is independently selected from cyano, halo, hydroxy, $C_1$–$C_4$ alkyl, and fluorinated $C_1$–$C_4$ alkyl,
   f) heterocycle, and
   g) substituted heterocycle wherein each substituent is independently selected from cyano, halo, hydroxy, $C_1$–$C_4$ alkyl, and fluorinated $C_1$–$C_4$ alkyl;
or $R^2$ and $R^3$ together with the carbon to which they are attached form $C_3$–$C_6$ cycloalkyl which is optionally substituted with one or more substituents independently selected from
1) hydroxy
2) $C_1$–$C_6$ alkyl,
3) $C_1$–$C_3$ alkoxy,
4) aryl,
5) substituted aryl wherein each substituent is independently selected from
   a) halo,
   b) hydroxy,
   c) $C_1$–$C_3$ alkoxy,
   d) $C_1$–$C_4$ alkyl,
   e) fluorinated $C_1$–$C_4$ alkyl,
   f) aryl,
   g) substituted aryl wherein each substituent is independently selected from halo, hydroxy, $C_1$–$C_4$ alkyl, and fluorinated $C_1$–$C_4$ alkyl,
   h) heterocycle,
   i) substituted heterocycle wherein each substituent is independently selected from halo, hydroxy, $C_1$–$C_4$ alkyl, and fluorinated $C_1$–$C_4$ alkyl,
6) heterocycle, and
7) substituted heterocycle wherein each substituent is independently selected from
   a) halo,
   b) hydroxy,
   c) $C_1$–$C_3$ alkoxy,
   d) $C_1$–$C_4$ alkyl,
   e) fluorinated $C_1$–$C_4$ alkyl,
   f) aryl,
   g) substituted aryl wherein each substituent is independently selected from halo, hydroxy, $C_1$–$C_4$ alkyl, and fluorinated $C_1$–$C_4$ alkyl,
   h) heterocycle, and
   i) substituted heterocycle wherein each substituent is independently selected from halo, hydroxy, $C_1$–$C_4$ alkyl, and fluorinated $C_1$–$C_4$ alkyl, or (B) $R^1$ and $R^2$ together with the nitrogen to which $R^1$ is attached and the carbon to which $R^2$ is attached form a 4- to 8-membered monocyclic heterocycle containing from 1 to 3 heteroatoms selected from nitrogen, oxygen, and sulfur, wherein at least one heteroatom in the monocyclic heterocycle is nitrogen and wherein the monocyclic heterocycle is optionally substituted with one or more substituents independently selected from
1) halo
2) hydroxy
3) $C_1$–$C_6$ alkyl,
4) $C_1$–$C_3$ alkoxy,
5) aryl, and
6) heterocycle;
and $R^3$ is as defined above in (A) when $R^3$ is independent from and not joined to $R^2$;

$R^4$ is $(CH_2)_m R^a$, wherein m is an integer from zero to 3 and $R^a$ is
1) hydrogen,
2) $C_1$–$C_6$ alkyl,
3) substituted $C_1$–$C_6$ alkyl wherein each substituent is independently selected from
   a) halo,
   b) hydroxy, and
   c) $C_1$–$C_3$ alkoxy,
4) aryl,
5) substituted aryl wherein each substituent is independently selected from
   a) halo,
   b) hydroxy,
   c) $C_1$–$C_3$ alkoxy,
   d) $C_1$–$C_4$ alkyl,
   e) fluorinated $C_1$–$C_4$ alkyl,
   f) aryl,
   g) substituted aryl wherein each substituent is independently selected from halo, hydroxy, $C_1$–$C_4$ alkyl, and fluorinated $C_1$–$C_4$ alkyl,
   h) heterocycle, and
   i) substituted heterocycle wherein each substituent is independently selected from halo, hydroxy, $C_1$–$C_4$ alkyl, and fluorinated $C_1$–$C_4$ alkyl,
6) heterocycle,
7) substituted heterocycle wherein each substituent is independently selected from
   a) halo,
   b) hydroxy,
   c) $C_1$–$C_3$ alkoxy,
   d) $C_1$–$C_4$ alkyl, e) fluorinated $C_1$–$C_4$ alkyl, f) aryl, g) substituted aryl wherein each substituent is independently selected from halo, hydroxy, $C_1$–$C_4$ alkyl, and fluorinated $C_1$–$C_4$ alkyl, h) heterocycle, and i) substituted heterocycle wherein each substituent is independently selected from halo, hydroxy, $C_1$–$C_4$ alkyl, and fluorinated $C_1$–$C_4$ alkyl;

$R^5$ is chroman, thiochroman, indanyl, dioxoisothiochroman, cyclopentyl, substituted chroman, substituted thiochroman, substituted indanyl, substituted dioxothiochroman, or substituted cyclopentyl; wherein each of the substituents on substituted chroman, thiochroman, indanyl, dioxoisothiochroman, or cyclopentyl is independently selected from halogen, cyano, hydroxy, $C_1$–$C_6$ alkyl, fluorinated $C_1$–$C_6$ alkyl, $C_{1-C4}$ alkoxy, or fluorinated $C_1$–$C_4$ alkoxy; and $R^6$ and $R^7$ are each independently 1) hydrogen, 2) $C_1$–$C_6$ alkyl, or 3) substituted $C_1$–$C_6$ alkyl wherein each substituent is independently selected from a) halo, b) hydroxy, c) aryl, d) substituted aryl, wherein each substituent is independently selected from halo, hydroxy, $C_1$–$C_4$ alkyl, fluorinated $C_1$–$C_4$ alkyl, and aryl, e) heterocycle, and f) substituted heterocycle, wherein each substituent is independently selected from halo, hydroxy, $C_1$–$C_4$ alkyl, fluorinated $C_1$–$C_4$ alkyl, and aryl, or $R^6$ and $R^7$ together with the nitrogen to which they are attached form $C_3$–$C_6$ azacycloalkyl which is optionally substituted with one or more substituents independently selected from 1) halo, 2) hydroxy, 3) $C_1$–$C_6$ alkyl, 4) $C_1$–$C_3$ alkoxy, 5) aryl, 6) substituted aryl wherein each substituent is independently selected from a) halo, b) hydroxy, c) $C_1$–$C_3$ alkoxy, d) $C_1$–$C_4$ alkyl, and e) fluorinated $C_1$–$C_4$ alkyl 7) heterocycle, and 8) substituted heterocycle wherein each substituent is independently selected from a) halo, b) hydroxy, c) $C_1$–$C_3$ alkoxy, d) $C_1$–$C_4$ alkyl, and e) fluorinated $C_1$–$C_4$ alkyl;

or pharmaceutically acceptable salt thereof.

The present invention also includes pharmaceutical compositions containing a compound of the present invention and methods of preparing such pharmaceutical compositions. The present invention further includes methods of treating AIDS, methods of preventing infetion by HIV, and methods of treating infection by HIV.

These and other embodiments, aspects and features of the present invention are either further described in or will be apparent from the ensuing description, examples, and appended claims.

DETAILED DESCRIPTION OF THE INVENTION

The present invention includes the compounds of Formula (I) above. These compounds and their pharmaceutically acceptable salts thereof are HIV protease inhibitors.

A first embodiment of the invention is a compound of Formula (I), wherein $R^1$, $R^2$, and $R^3$ are as defined in (A); and all of variables are as originally defined above;

or a pharmaceutically acceptable salt thereof.

A second embodiment of the invention is a compound of Formula (I), wherein $R^1$ is hydrogen or $C_1$–$C_4$ alkyl;

$R^2$ and $R^3$ are each independently selected from hydrogen or $C_1$–$C_4$ alkyl; or $R^2$ and $R^3$ together with the carbon to which they are attached form $C_3$–$C_6$ cycloalkyl;

$R^4$ is $(CH_2)_m R^a$, wherein m is an integer from zero to 3 and $R^a$ is 1) hydrogen, 2) $C_1$–$C_4$ alkyl, 3) substituted $C_1$–$C_4$ alkyl wherein each substituent is independently selected from a) halo, b) hydroxy, and c) $C_1$–$C_3$ alkoxy, 4) phenyl, 5) mono- or di- or tri-substituted phenyl wherein each substituent is independently selected from a) halo, b) hydroxy, c) $C_1$–$C_3$ alkoxy, d) $C_1$–$C_4$ alkyl, e) $(CH_2)_{0-3}CF_3$, f) phenyl, g) mono- or di- or tri-substituted phenyl, wherein each substituent is independently selected from halo, hydroxy, $C_1$–$C_4$ alkyl, and $(CH_2)_{0-3}CF_3$, h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and i) mono- or di- or tri-substituted heterocycle, wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from halo, hydroxy, $C_1$–$C_4$ alkyl, and $(CH_2)_{0-3}CF_3$;

6) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, tetrazolyl, and furopyridyl, or 7) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, tetrazolyl, and furopyridyl, and wherein each substituent is independently selected from
a) halo,
b) hydroxy,
c) $C_1$–$C_3$ alkoxy,
d) $C_1$–$C_4$ alkyl,
e) $(CH_2)_{0-3}CF_3$,
f) phenyl,
g) mono- or di- or tri-substituted phenyl wherein each substituent is independently selected from halo, hydroxy, $C_1$–$C_4$ alkyl, and $(CH_2)_{0-3}CF_3$,
h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and
i) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and wherein each substituent is independently selected from halo, hydroxy, $C_1$–$C_4$ alkyl, and $(CH_2)_{0-3}CF_3$;

$R^5$ is chroman, thiochroman, indanyl, dioxoisothiochroman, cyclopentyl, substituted chroman, substituted thiochroman, substituted indanyl, substituted dioxothiochroman, or substituted cyclopentyl; wherein each of the substituents on substituted chroman, thiochroman, indanyl, dioxoisothiochroman, or cyclopentyl is independently selected from halogen, cyano, hydroxy, $C_1$–$C_4$ alkyl, $(CH_2)_{0-3}CF_3$, $C_{1-C_4}$ alkoxy, or $(CH_2)_{0-3}OCF_3$; and $R^6$ and $R^7$ are each independently
1) hydrogen,
2) $C_1$–$C_4$ alkyl, or
3) substituted $C_1$–$C_4$ alkyl wherein each substituent is independently selected from
a) halo,
b) hydroxy,
c) phenyl,
d) mono- or di- or tri-substituted phenyl, wherein each substituent is independently selected from halo, hydroxy, $C_1$–$C_4$ alkyl, $(CH_2)_{0-3}CF_3$, and phenyl,
e) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and
f) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and wherein each substituent is independently selected from halo, hydroxy, $C_1$–$C_4$ alkyl, $(CH_2)_{0-3}CF_3$, and phenyl;
or
$R^6$ and $R^7$ together with the nitrogen to which they are attached form $C_3$–$C_6$ azacycloalkyl which is optionally substituted with one or more substituents independently selected from
1) halo
2) hydroxy
3) $C_1$–$C_4$ alkyl, and
4) $C_1$–$C_3$ alkoxy;
or a pharmaceutically acceptable salt thereof.

A third embodiment of the invention is a compound of Formula (I), wherein
$R^4$ is $(CH_2)_m R^a$, wherein m is an integer from zero to 3 and $R^a$ is
1) hydrogen,
2) $C_1$–$C_4$ alkyl,
3) substituted $C_1$–$C_4$ alkyl wherein each substituent is independently selected from
a) halo,
b) hydroxy, and
c) $C_1$–$C_3$ alkoxy,
4) phenyl,
5) mono- or di- or tri-substituted phenyl wherein each substituent is independently selected from
a) halo,
b) hydroxy,
c) $C_1$–$C_3$ alkoxy,
d) $C_1$–$C_4$ alkyl,
e) $(CH_2)_{0-3}CF_3$,
f) phenyl,
g) mono- or di- or tri-substituted phenyl, wherein each substituent is independently selected from halo, hydroxy, $C_1$–$C_4$ alkyl, and $(CH_2)_{0-3}CF_3$,
h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and
i) mono- or di- or tri-substituted heterocycle, wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from halo, hydroxy, $C_1$–$C_4$ alkyl, and $(CH_2)_{0-3}CF_3$;
6) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, or
7) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from
a) halo,
b) hydroxy,
c) $C_1$–$C_3$ alkoxy,
d) $C_1$–$C_4$ alkyl,
e) $(CH_2)_{0-3}CF_3$,
f) phenyl,
g) mono- or di- or tri-substituted phenyl wherein each substituent is independently selected from halo, hydroxy, $C_1$–$C_4$ alkyl, and $(CH_2)_{0-3}CF_3$,
h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and
i) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from halo, hydroxy, $C_1$–$C_4$ alkyl, and $(CH_2)_{0-3}CF_3$;

$R^6$ and $R^7$ are each independently
1) hydrogen,
2) $C_1$–$C_4$ alkyl, or
3) substituted $C_1$–$C_4$ alkyl wherein each substituent is independently selected from
   a) halo,
   b) hydroxy,
   c) phenyl,
   d) mono- or di- or tri-substituted phenyl, wherein each substituent is independently selected from halo, hydroxy, $C_1$–$C_4$ alkyl, $(CH_2)_{0-3}CF_3$, and phenyl,
   e) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and
   f) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from halo, hydroxy, $C_1$–$C_4$ alkyl, $(CH_2)_{0-3}CF_3$, and phenyl;

or
$R^6$ and $R^7$ together with the nitrogen to which they are attached form $C_3$–$C_6$ azacycloalkyl which is optionally substituted with one or more substituents independently selected from
1) halo
2) hydroxy
3) $C_1$–$C_4$ alkyl, and
4) $C_1$–$C_3$ alkoxy;

and all other variables are as defined in the second embodiment;
or a pharmaceutically acceptable salt thereof.

A first class of the invention is a compound of Formula (I), wherein
$R^5$ is chroman, indanyl, substituted chroman, or substituted indanyl;
and all other variables are as defined in the second embodiment;
or a pharmaceutically acceptable salt thereof.

In a sub-class of the first class is a compound of Formula (I), wherein
$R^a$ is
1) $C_1$–$C_4$ alkyl,
2) substituted $C_1$–$C_4$ alkyl wherein each substituent is independently selected from
   a) halo,
   b) hydroxy, and
   c) $C_1$–$C_3$ alkoxy,
3) phenyl,
4) mono- or di- or tri-substituted phenyl wherein each substituent is independently selected from
   a) halo,
   b) hydroxy,
   c) $C_1$–$C_3$ alkoxy,
   d) $C_1$–$C_4$ alkyl,
   e) $CF_3$,
   f) phenyl,
   g) mono- or di- or tri-substituted phenyl, wherein each substituent is independently selected from halo, hydroxy, $C_1$–$C_4$ alkyl, and $CF_3$,
   h) heterocycle selected from pyridyl, pyrazinyl and pyrimidinyl, and
   i) mono- or di- or tri-substituted heterocycle, wherein heterocycle is selected from pyridyl, pyrazinyl, and pyrimidinyl, and wherein each substituent is independently selected from halo, hydroxy, $C_1$–$C_4$ alkyl, and $CF_3$;
5) heterocycle selected from pyridyl, pyrazinyl and pyrimidinyl, or
6) mono- or di- or tri-substituted heterocycle wherein heterocycle is selected from pyridyl, pyrazinyl and pyrimidinyl; and wherein each substituent is independently selected from
   a) halo,
   b) hydroxy,
   c) $C_1$–$C_3$ alkoxy,
   d) $C_1$–$C_4$ alkyl,
   e) $CF_3$,
   f) phenyl,
   g) mono- or di- or tri-substituted phenyl wherein each substituent is independently selected from cyano, halo, hydroxy, $C_1$–$C_4$ alkyl, and $CF_3$,
   h) heterocycle selected from pyridyl, pyrazinyl and pyrimidinyl, and
   i) mono- or di- or tri-substituted heterocycle wherein heterocycle is selected from pyridyl, pyrazinyl and pyrimidinyl, and wherein each substituent is independently selected from cyano, halo, hydroxy, $C_1$–$C_4$ alkyl, and $CF_3$; and $R^6$ and $R^7$ are each independently
1) hydrogen,
2) $C_1$–$C_6$ alkyl, or
3) substituted $C_1$–$C_6$ alkyl wherein each substituent is independently selected from
   a) halo,
   b) hydroxy,
   c) phenyl,
   d) mono- or di- or tri-substituted phenyl, wherein each substituent is independently selected from halo, hydroxy, $C_1$–$C_4$ alkyl, and $CF_3$,
   e) heterocycle selected from pyridyl, pyrazinyl and pyrimidinyl, and
   f) mono- or di- or tri-substituted heterocycle wherein heterocycle is selected from pyridyl, pyrazinyl and pyrimidinyl, and wherein each substituent is independently selected from halo, hydroxy, $C_1$–$C_4$ alkyl, and $(CH_2)_{0-3}CF_3$; and all other variables are as defined in the first class;
or a pharmaceutically acceptable salt thereof.

In another sub-class of the first class is a compound of Formula (I), wherein
$R^4$ is $CH_2R^a$, wherein $R^a$ is
1) phenyl,
2) mono- or di- or tri-substituted phenyl wherein each substituent is independently selected from
   a) halo,
   b) hydroxy,
   c) $C_1$–$C_3$ alkoxy,
   d) $C_1$–$C_4$ alkyl, and
   e) $CF_3$,
3) heterocycle selected from pyridyl, pyrazinyl and pyrimidinyl, or
4) mono- or di- or tri-substituted heterocycle wherein heterocycle is selected from pyridyl, pyrazinyl and pyrimidinyl; and wherein each substituent is independently selected from a) halo,
b) hydroxy,
c) $C_1$–$C_3$ alkoxy,
d) $C_1$–$C_4$ alkyl, and
e) $CF_3$;

and all other variables are as defined in the first class;
or a pharmaceutically acceptable salt thereof.

A second class of the invention is a compound of Formula (I), wherein
$R^5$ is chroman, indanyl, substituted chroman, or substituted indanyl;
and all other variables are as defined in the third embodiment;
or a pharmaceutically acceptable salt thereof.

The second class of the invention has sub-classes analogous to the sub-classes set forth above for the first class of the invention.

Exemplifying the invention are compounds selected from the group consisting of ($\alpha$S,$\gamma$R)-$\gamma$-[[((3S,4S)-3,4-dihydro-3-hydroxy-2H-1-benzopyran-4-yl)amino]carbonyl]-$\alpha$-hydroxy-N-[1-[[[(2-methylphenyl)methyl]amino]carbonyl]cyclopentyl] benzene pentanamide;

($\alpha$S,$\gamma$R)-$\gamma$-[[((3S,4S)-3,4-dihydro-3-hydroxy-2H-1-benzopyran-4-yl)amino]carbonyl]-$\alpha$-hydroxy-N-[1,1-dimethyl-2-[[(2-methylphenyl)methyl]amino]-2-oxoethyl] benzenepentanamide;

and pharmaceutically acceptable salts thereof.

A fourth embodiment of the invention is a compound of Formula (II):

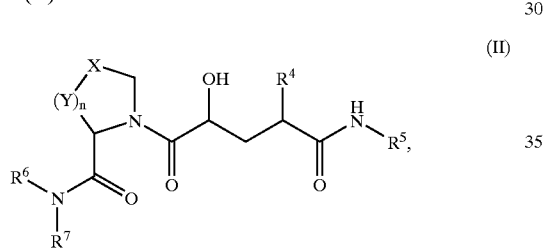

(II)

wherein X is
1) $S(O)_p$ wherein p is an integer equal to 0,1, or 2
2) O, or
3) $CR^bR^c$, wherein $R^b$ and $R^c$ are each independently
   a) hydrogen,
   b) hydroxy,
   c) halo,
   d) $C_1$–$C_4$ alkyl,
   e) $C_1$–$C_3$ alkoxy,
   f) aryl, or
   g) heterocycle;

Y is $CR^dR^e$, wherein $R^d$ and $R^e$ are each independently
   a) hydrogen,
   b) halo, or
   c) $C_1$–$C_4$ alkyl;

n is an integer equal to 0, 1, or 2;
and all other variables are as originally defined;
or a pharmaceutically acceptable salt thereof.

In a fifth embodiment of the invention, the compound is of Formula (II), wherein
$R^4$ is $(CH_2)_mR^a$, wherein m is an integer from zero to 3 and $R^a$ is
1) hydrogen,
2) $C_1$–$C_4$ alkyl,
3) substituted $C_1$–$C_4$ alkyl wherein each substituent is independently selected from a) halo,
b) hydroxy, and
c) $C_1$–$C_3$ alkoxy,
4) phenyl,
5) mono- or di- or tri-substituted phenyl wherein each substituent is independently selected from
   a) halo,
   b) hydroxy,
   c) $C_1$–$C_3$ alkoxy,
   d) $C_1$–$C_4$ alkyl,
   e) $(CH_2)_{0-3}CF_3$,
   f) phenyl,
   g) mono- or di- or tri-substituted phenyl, wherein each substituent is independently selected from halo, hydroxy, $C_1$–$C_4$ alkyl, and $(CH_2)_{0-3}CF_3$,
   h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and
   i) mono- or di- or tri-substituted heterocycle, wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and wherein each substituent is independently selected from halo, hydroxy, $C_1$–$C_4$ alkyl, and $(CH_2)_{0-3}CF_3$;
6) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, tetrazolyl, and furopyridyl, or
7) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, tetrazolyl, and furopyridyl, and wherein each substituent is independently selected from
   a) halo,
   b) hydroxy,
   c) $C_1$–$C_3$ alkoxy,
   d) $C_1$–$C_4$ alkyl,
   e) $(CH_2)_{0-3}CF_3$,
   f) phenyl,
   g) mono- or di- or tri-substituted phenyl wherein each substituent is independently selected from halo, hydroxy, $C_1$–$C_4$ alkyl, and $(CH_2)_{0-3}CF_3$,
   h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and
   i) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from halo, hydroxy, $C_1$–$C_4$ alkyl, and $(CH_2)_{0-3}CF_3$;

$R^5$ is chroman, thiochroman, indanyl, dioxoisothiochroman, cyclopentyl, substituted chroman, substituted thiochroman, substituted indanyl, substituted dioxothiochroman, or substituted cyclopentyl; wherein each of the substituents on substituted chroman, thiochroman, indanyl, dioxoisothiochroman, or cyclopentyl is independently selected from halogen, cyano, hydroxy, $C_1$–$C_4$ alkyl, $(CH_2)_{0-3}CF_3$, $C_1$–$C_4$ alkoxy, or $(CH_2)_{0-3}OCF_3$;

$R^6$ and $R^7$ are each independently
1) hydrogen,
2) $C_1$–$C_4$ alkyl, or
3) substituted $C_1$–$C_4$ alkyl wherein each substituent is independently selected from
   a) halo,
   b) hydroxy,
   c) phenyl, and
   d) mono- or di- or tri-substituted phenyl, wherein each substituent is independently selected from halo, hydroxy, $C_1$–$C_4$ alkyl, and $(CH_2)_{0-3}CF_3$,
   e) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and
   f) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and wherein each substituent is independently selected from halo, hydroxy, $C_1$–$C_4$ alkyl, and $(CH_2)_{0-3}CF_3$;

or $R^6$ and $R^7$ together with the nitrogen to which they are attached form $C_3$–$C_6$ azacycloalkyl which is optionally substituted with one or more substituents independently selected from
1) halo
2) hydroxy
3) $C_1$–$C_4$ alkyl, and
4) $C_1$–$C_3$ alkoxy;

and all other variables are as defined in the second embodiment;
or a pharmaceutically acceptable salt thereof.

A sixth embodiment of the invention is a compound of Formula (II) wherein
$R^4$ is $(CH_2)_m R^a$, wherein m is an integer from zero to 3 and $R^a$ is
1) hydrogen,
2) $C_1$–$C_4$ alkyl,
3) substituted $C_1$–$C_4$ alkyl wherein each substituent is independently selected from
   a) halo,
   b) hydroxy, and
   c) $C_1$–$C_3$ alkoxy,
4) phenyl,
5) mono- or di- or tri-substituted phenyl wherein each substituent is independently selected from
   a) halo,
   b) hydroxy,
   c) $C_1$–$C_3$ alkoxy,
   d) $C_1$–$C_4$ alkyl,
   e) $(CH_2)_{0-3}CF_3$,
   f) phenyl,
   g) mono- or di- or tri-substituted phenyl, wherein each substituent is independently selected from halo, hydroxy, $C_1$–$C_4$ alkyl, and $(CH_2)_{0-3}CF_3$,
   h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and
   i) mono- or di- or tri-substituted heterocycle, wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from halo, hydroxy, $C_1$–$C_4$ alkyl, and $(CH_2)_{0-3}CF_3$;
6) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, or
7) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from
   a) halo,
   b) hydroxy,
   c) $C_1$–$C_3$ alkoxy,
   d) $C_1$–$C_4$ alkyl,
   e) $(CH_2)_{0-3}CF_3$,
   f) phenyl,
   g) mono- or di- or tri-substituted phenyl wherein each substituent is independently selected from halo, hydroxy, $C_1$–$C_4$ alkyl, and $(CH_2)_{0-3}CF_3$,
   h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, traizolyl, and tetrazolyl, and
   i) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from halo, hydroxy, $C_1$–$C_4$ alkyl, and $(CH_2)_{0-3}CF_3$;

and all other variables are as defined in the third embodiment;
or a pharmaceutically acceptable salt thereof.

A seventh embodiment of the invention is a compound of Formula (III):

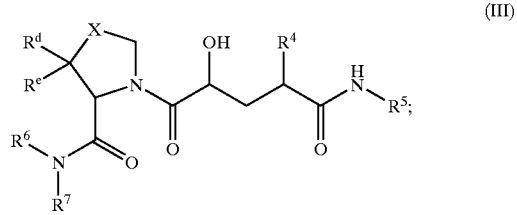

(III)

wherein
X is S, O or $CR^b R^c$, wherein $R^b$ and $R^c$ are each independently hydrogen, hydroxy, halo, or $C_1$–$C_3$ alkoxy;
and all other variables are as defined in the fifth embodiment;
or a pharmaceutically acceptable salt thereof.

An eighth embodiment of the invention is a compound of Formula (III), wherein
X is S, O or $CR^b R^c$, wherein $R^b$ and $R^c$ are each independently hydrogen, hydroxy, halo, or $C_1$–$C_3$ alkoxy;
and all other variables are as defined in the sixth embodiment;
or a pharmaceutically acceptable salt thereof.

A third class of the invention is a compound of Formula (III), wherein
$R^5$ is chroman, indanyl, cyclopentyl, substituted chroman, substituted indanyl, or substituted cyclopentyl;
and all other variables are as defined in the seventh embodiment;
or a pharmaceutically acceptable salt thereof.

A fourth class of the invention is a compound of Formula (III), wherein
$R^5$ is chroman, indanyl, cyclopentyl, substituted chroman, substituted indanyl, or substituted cyclopentyl;
and all other variables are as defined in the eighth embodiment;
or a pharmaceutically acceptable salt thereof.

A fifth class of the invention is a compound of Formula (III), wherein
$R^a$ is
1) $C_1$–$C_4$ alkyl,
2) substituted $C_1$–$C_4$ alkyl wherein each substituent is independently selected from
   a) halo,
   b) hydroxy, and
   c) $C_1$–$C_3$ alkoxy,
3) phenyl,
4) mono- or di- or tri-substituted phenyl wherein each substituent is independently selected from
   a) halo,
   b) hydroxy,
   c) $C_1$–$C_3$ alkoxy,
   d) $C_1$–$C_4$ alkyl,
   e) $CF_3$,
   f) phenyl,
   g) mono- or di- or tri-substituted phenyl, wherein each substituent is independently selected from halo, hydroxy, $C_1$–$C_4$ alkyl, and $CF_3$,
   h) heterocycle selected from pyridyl, pyrazinyl and pyrimidinyl, and
   i) mono- or di- or tri-substituted heterocycle, wherein heterocycle is selected from pyridyl, pyrazinyl and pyrimidinyl, and wherein each substituent is independently selected from halo, hydroxy, $C_1$–$C_4$ alkyl, and $CF_3$;
5) heterocycle selected from pyridyl, pyrazinyl, pyrimidinyl, oxazolyl, thiazolyl, and furopyridyl, or
6) mono- or di- or tri-substituted heterocycle wherein heterocycle is selected from pyridyl, pyrazinyl, pyrimidinyl, oxazolyl, thiazolyl, and furopyridyl; and wherein each substituent is independently selected from
   a) halo,
   b) hydroxy,
   c) $C_1$–$C_3$ alkoxy,
   d) $C_1$–$C_4$ alkyl,
   e) $CF_3$,
   f) phenyl,
   g) mono- or di- or tri-substituted phenyl wherein each substituent is independently selected from cyano, halo, hydroxy, $C_1$–$C_4$ alkyl, and $CF_3$,
   h) heterocycle selected from pyridyl, pyrazinyl and pyrimidinyl, and
   i) mono- or di- or tri-substituted heterocycle wherein heterocycle is selected from pyridyl, pyrazinyl and pyrimidinyl, and wherein each substituent is independently selected from cyano, halo, hydroxy, $C_1$–$C_4$ alkyl, and $CF_3$; and $R^6$ and $R^7$ are each independently
1) hydrogen,
2) $C_1$–$C_4$ alkyl, or
3) substituted $C_1$–$C_4$ alkyl wherein each substituent is independently selected from
   a) halo,
   b) hydroxy,
   c) phenyl,
   d) mono- or di- or tri-substituted phenyl, wherein each substituent is independently selected from halo, hydroxy, $C_1$–$C_4$ alkyl, and $CF_3$,
   e) heterocycle selected from pyridyl, pyrazinyl and pyrimidinyl, and
   f) mono- or di- or tri-substituted heterocycle wherein heterocycle is selected from pyridyl, pyrazinyl and pyrimidinyl, and wherein each substituent is independently selected from halo, hydroxy, $C_1$–$C_4$ alkyl, and $(CH_2)_{0-3}CF_3$;
and all other variables are as defined in the third class;
or a pharmaceutically acceptable salt thereof.

In one aspect of the fifth class, $R^4$ is $CH_2R^a$, wherein $R^a$ is
1) phenyl,
2) mono- or di- or tri-substituted phenyl wherein each substituent is independently selected from
   a) halo,
   b) hydroxy,
   c) $C_1$–$C_3$ alkoxy,
   d) $C_1$–$C_4$ alkyl, and
   e) $CF_3$,
3) heterocycle selected from pyridyl, pyrazinyl, pyrimidinyl, oxazolyl, thiazolyl, and furopyridyl, or
4) mono- or di- or tri-substituted heterocycle wherein heterocycle is selected from pyridyl, pyrazinyl, pyrimidinyl, oxazolyl, thiazolyl, and furopyridyl; and wherein each substituent is independently selected from
   a) halo,
   b) hydroxy,
   c) $C_1$–$C_3$ alkoxy,
   d) $C_1$–$C_4$ alkyl, and
   e) $CF_3$.

In another aspect of the fifth class, X is S or $CR^bR^c$.

A sixth class of the invention is a compound of Formula (III), wherein
$R^a$ is
1) $C_1$–$C_4$ alkyl,
2) substituted $C_1$–$C_4$ alkyl wherein each substituent is independently selected from
   a) halo,
   b) hydroxy, and
   c) $C_1$–$C_3$ alkoxy,
3) phenyl,
4) mono- or di- or tri-substituted phenyl wherein each substituent is independently selected from
   a) halo,
   b) hydroxy,
   c) $C_1$–$C_3$ alkoxy,
   d) $C_1$–$C_4$ alkyl,
   e) $CF_3$,
   f) phenyl,
   g) mono- or di- or tri-substituted phenyl, wherein each substituent is independently selected from halo, hydroxy, $C_1$–$C_4$ alkyl, and $CF_3$,
   h) heterocycle selected from pyridyl, pyrazinyl and pyrimidinyl, and i) mono- or di- or tri-substituted heterocycle, wherein heterocycle is selected from pyridyl, pyrazinyl, and pyrimidinyl, and wherein each substituent is independently selected from halo, hydroxy, $C_1$–$C_4$ alkyl, and $CF_3$;

5) heterocycle selected from pyridyl, pyrazinyl, pyrimidinyl, or
6) mono- or di- or tri-substituted heterocycle wherein heterocycle is selected from pyridyl, pyrazinyl, and pyrimidinyl; and wherein each substituent is independently selected from
a) halo,
b) hydroxy,
c) $C_1$–$C_3$ alkoxy,
d) $C_1$–$C_4$ alkyl,
e) $CF_3$,
f) phenyl,
g) mono- or di- or tri-substituted phenyl wherein each substituent is independently selected from cyano, halo, hydroxy, $C_1$–$C_4$ alkyl, and $CF_3$,
h) heterocycle selected from pyridyl, pyrazinyl and pyrimidinyl, and
i) mono- or di- or tri-substituted heterocycle wherein heterocycle is selected from pyridyl, pyrazinyl and pyrimidinyl, and wherein each substituent is independently selected from cyano, halo, hydroxy, $C_1$–$C_4$ alkyl, and $CF_3$; and $R^6$ and $R^7$ are each independently
1) hydrogen,
2) $C_1$–$C_4$ alkyl, or
3) substituted $C_1$–$C_4$ alkyl wherein each substituent is independently selected from
a) halo,
b) hydroxy,
c) phenyl,
d) mono- or di- or tri-substituted phenyl, wherein each substituent is independently selected from halo, hydroxy, $C_1$–$C_4$ alkyl, and $CF_3$,
e) heterocycle selected from pyridyl, pyrazinyl and pyrimidinyl, and
f) mono- or di- or tri-substituted heterocycle wherein heterocycle is selected from pyridyl, pyrazinyl and pyrimidinyl, and wherein each substituent is independently selected from halo, hydroxy, $C_1$–$C_4$ alkyl, and $(CH_2)_{0-3}CF_3$;

and all other variables are as defined in the fourth class; or a pharmaceutically acceptable salt thereof.

In one aspect of the sixth class, $R^4$ is $CH_2R^a$, wherein $R^a$ is
1) phenyl,
2) mono- or di- or tri-substituted phenyl wherein each substituent is independently selected from
a) halo,
b) hydroxy,
c) $C_1$–$C_3$ alkoxy,
d) $C_1$–$C_4$ alkyl, and
e) $CF_3$,
3) heterocycle selected from pyridyl, pyrazinyl, pyrimidinyl, oxazolyl, and furopyridyl, or
4) mono- or di- or tri-substituted heterocycle wherein heterocycle is selected from pyridyl, pyrazinyl, pyrimidinyl, oxazolyl, and furopyridyl; and wherein each substituent is independently selected from
a) halo,
b) hydroxy,
c) $C_1$–$C_3$ alkoxy,
d) $C_1$–$C_4$ alkyl, and
e) $CF_3$.

In another aspect of the sixth class, X is S or $CR^bR^c$.

Also exemplifying the invention are compounds selected from the group consisting of (4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-5,5-dimethyl-N-[(2-methylphenyl) methyl]-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(2,2,2-trifluoroethyl)-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-5,5-dimethyl-N-(1,1-dimethylethyl)-4-thiazolidinecarboxamide;

(4R)-3-[(2S,4R)-5-[((1S,2R)-2,3-dihydro-2-hydroxy-1H-inden-1-yl)amino]-2-hydroxy-1,5-dioxo-4-(phenylmethyl) pentyl]-5,5-dimethyl-N-(2,2,2-trifluoroethyl)-4-thiazolidinecarboxamide;

(4R)-3-[(2S,4R)-5-[((1S,2R)-2,3-dihydro-2-hydroxy-1H-inden-1-yl)amino]-2-hydroxy-1,5-dioxo-4-(phenylmethyl) pentyl]-5,5-dimethyl-N-(1,1-dimethylethyl)-4-thiazolidinecarboxamide;

(4R)-3-[(2S,4R)-5-[((1S,2R)-2,3-dihydro-2-hydroxy-1H-inden-1-yl)amino]-2-hydroxy-1,5-dioxo-4-(phenylmethyl) pentyl]-5,5-dimethyl-N-[(2-methylphenyl)-methyl]-4-thiazolidinecarboxamide;

(2S)-1-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-N-[(2-methylphenyl)-methyl]-2-pyrrolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-5,5-dimethyl-N-(4-pyridinylmethyl)-4-thiazolidinecarboxamide;

(2S)-1-[(2S,4R)-5-[((1S,2R)-2,3-dihydro-2-hydroxy-1H-inden-1-yl)amino]-2-hydroxy-1,5-dioxo-4-(phenylmethyl) pentyl]-N-[(2-methylphenyl)-methyl]-2-pyrrolidinecarboxamide;

(4R)-3-[(2S,4R)-5-[((1S,2R)-2,3-dihydro-2-hydroxy-1H-inden-1-yl)amino]-2-hydroxy-1,5-dioxo-4-(phenylmethyl) pentyl]-5,5-dimethyl-N-(3-pyridinylmethyl)-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-5,5-dimethyl-N-(2-phenylethyl)-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(3-pyridinylmethyl) pentyl]-5,5-dimethyl-N-[(2-methylphenyl methyl]-4-thiazolidinecarboxamide;

(4R)3-[(2S,4R)-5-[((1S,2R,5R)-5-methyl-2-hydroxy-1-cyclopentyl)amino]-2-hydroxy-1,5-dioxo-4-(phenylmethyl) pentyl]-5,5-dimethyl-N-[(2-methylphenyl)-methyl]-4-thiazolidinecarboxamide;

(2S,4S)-1-[(2S,4R)-5-[((1S,2R)-2,3-dihydro-2-hydroxy-1H-inden-1-yl)amino]-2-hydroxy-1,5-dioxo-4-(phenylmethyl) pentyl]-N-[(2-methylphenyl)methyl]-4-chloro-2-pyrrolidinecarboxamide;

and pharmaceutically acceptable salts thereof.

Also exemplifying the invention are compounds selected from the group consisting of (4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-3,3-dimethyl-N-[(2,6-dimethylphenyl)-methyl]-2-pyrrolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-3,3-dimethyl-N-[(3-methyl-2-pyridylmethyl)]-2-pyrrolidinecarboxamide;

(4R)-3-[(2S,4R)-5-[((3S,4S)-3,4-dihydro-3-dihydro-3-hydroxy-2H-1-benzopyran-4-yl)amino]-2-hydroxy-1,5-dioxo-4-(phenylmethyl) pentyl]-5,5-dimethyl-N-[(2,6-dimethylphenyl) methyl]-4-oxazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-5,5-dimethyl-N-[(2,6-dimethylphenyl) methyl]-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-5,5-dimethyl-N-[(3-methyl-2-pyridinylmethyl)]-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-5,5-dimethyl-N-[(3,5-dimethyl-4-isoxazolemethyl)]-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl) pentyl]-5,5-dimethyl-N-[(2,6-dimethylphenyl) methyl]-4-thiazolidinecarboxamide-1,1-dioxide;

(4R)-N-[(2-chloro-6-methylphenyl)methyl]-3-[(2S,4S)-5-[((3S,4S)-3,4-dihydro-3-hydroxy-2H-1-benzopyran-4-yl)amino]-4-(furo[2,3-c]pyridin-2-ylmethyl)-2-hydroxy-1,5-dioxopentyl]-5,5-dimethyl-4-thiazolidinecarboxamide;

(4R)-N-[(2-chloro-6-methylphenyl)methyl]-3-[(2S,4S)-5-[((3S,4S)-3,4-dihydro-3-hydroxy-2H-1-benzopyran-4-yl) amino]-2-hydroxy-4-(5-oxazolymethyl)-1,5-dioxopentyl]-5,5-dimethyl-4-thiazolidinecarboxamide;

and pharmaceutically acceptable salts thereof.

Other embodiments of the present invention include the following:

(a) A pharmaceutical composition comprising a therapeutically effective amount of a compound of Formula (I) and a pharmaceutically acceptable carrier.

(b) A pharmaceutical composition made by combining a therapeutically effective amount of a compound of Formula (I) and a pharmaceutically acceptable carrier.

(c) The pharmaceutical composition of (a), wherein the composition further comprises a therapeutically effective amount of at least one HIV infection/AIDS treatment agent selected from the group consisting of HIV/AIDS antiviral agents, immunomodulators, and anti-infective agents.

(d) The pharmaceutical composition of (a), wherein the composition further comprises a therapeutically effective amount of at least one antiviral selected from the group consisting of non-nucleoside HIV reverse transcriptase inhibitors and nucleoside HIV reverse transcriptase inhibitors.

(e) The pharmaceutical composition of (d), further comprising a therapeutically effective amount of an additional HIV protease inhibitor.

(f) A method of inhibiting HIV protease in a subject in need thereof which comprises administering to the subject a therapeutically effective amount of a compound of Formula (I).

(g) A method of preventing or treating infection by HIV in a subject in need thereof which comprises administering to the subject a therapeutically effective amount of a compound of Formula (I).

(h) The method of (g), wherein the compound of Formula (I) is administered in combination with a therapeutically effective amount of at least one antiviral selected from the group consisting of non-nucleoside HIV reverse transcriptase inhibitors and nucleoside HIV reverse transcriptase inhibitors.

(i) A method of treating AIDS in a subject in need thereof which comprises administering to the subject a therapeutically effective amount of a compound of Formula (I).

(j) The method of (i), wherein the compound is administered in combination with a therapeutically effective amount of at least one HIV infection/AIDS treatment agent selected from the group consisting of HIV/AIDS antiviral agents, immunomodulators, and anti-infective agents.

(k) The method of (i), wherein the compound is administered in combination with a therapeutically effective amount of at least one antiviral selected from the group consisting of non-nucleoside HIV reverse transcriptase inhibitors and nucleoside HIV reverse transcriptase inhibitors.

(l) A method of inhibiting HIV protease in a subject in need thereof which comprises administering to the subject a therapeutically effective amount of the composition of (a) or (b).

(m) A method of preventing or treating infection by HIV in a subject in need thereof which comprises administering to the subject a therapeutically effective amount of the composition of (a) or (b) or (c) or (d) or (e).

(n) A method of treating AIDS in a subject in need thereof which comprises administering to the subject a therapeutically effective amount of the composition of (a) or (b) or (c) or (d) or (e).

Additional embodiments of the invention include the pharmaceutical compositions and methods set forth in (a)–(n) above, wherein the compound employed therein is a compound of one of the embodiments, classes, or subclasses of compounds described above.

As used herein, the term "$C_1$–$C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl.

The term "$C_1$–$C_6$ alkoxy" means an —O-alkyl group wherein alkyl is $C_1$ to $C_6$ alkyl as defined above. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy. Similarly, "$C_1$–$C_3$ alkoxy" is selected from methoxy, ethoxy, n-propoxy, and isopropoxy.

The term "$C_3$–$C_7$ cycloalkyl" means a cyclic ring of an alkane having three to seven total carbon atoms (i.e., cyclopropyl, cyclobutyl, cyclopentyl, cyclohexyl, or cycloheptyl). The term "$C_3$–$C_6$ cycloalkyl" refers to a cyclic ring selected from cyclopropyl, cyclobutyl, cyclopentyl, and cyclohexyl. "$C_3$–$C_5$ cycloalkyl" has an analogous meaning.

The term "halogen" (which may alternatively be referred to as "halo") refers to fluorine, chlorine, bromine and iodine (alternatively, fluoro, chloro, bromo, and iodo).

The term "fluorinated $C_1$–$C_6$ alkyl" (which may alternatively be referred to as "$C_1$–$C_6$ fluoroalkyl") means a $C_1$ to $C_6$ linear or branched alkyl group as defined above with one or more fluorine substituents. The term "fluorinated $C_1$–$C_4$ alkyl" has an analogous meaning. Representative examples of suitable fluoroalkyls include the series $(CH_2)_{0-3}CF_3$ (i.e., trifluoromethyl, 2,2,2-trifluoroethyl, 3,3,3-trifluoro-n- propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. The terms "fluorinated $C_1$–$C_4$ alkoxy" and "fluorinated $C_1$–$C_3$ alkoxy" have analogous meanings. Representative examples include the series $O(CH_2)_{0-3}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "aryl" refers to aromatic mono- and polycarbocyclic ring systems, wherein the carbocyclic rings in the polyring systems may be fused or attached to each other via single bonds. Suitable aryl groups include, but are not limited to, phenyl, naphthyl, and biphenylenyl.

The term "substituted aryl" refers to aryl groups as defined above having one or more substituents independently selected from cyano, halo, hydroxy, $C_1$–$C_6$ alkyl, $C_1$–$C_6$ alkoxy, fluorinated $C_1$–$C_6$ alkyl, fluorinated $C_1$–$C_6$ alkoxy, aryl and the like.

The term "heterocycle" (which may alternatively be referred to as "heterocyclic") broadly refers to a 4- to 8-membered monocyclic ring or 7- to 10-membered bicyclic ring system, any ring of which is saturated or unsaturated, and which consists of carbon atoms and one or more heteroatoms selected from N, O and S, and wherein the nitrogen and sulfur heteroatoms may optionally be oxidized, and the nitrogen heteroatom may optionally be quaternized. The heterocyclic ring may be attached at any heteroatom or carbon atom, provided that attachment results in the creation of a stable structure. It is understood that "unsaturated" means that the ring or rings may be partially or completely unsaturated. Representative examples of heterocyclics include piperidinyl, piperazinyl, azepinyl, pyrrolyl, pyrrolidinyl, pyrazolyl, pyrazolidinyl, imidazolyl, imidazolidinyl, imidazolinyl, pyridyl, pyrazinyl, pyrimidinyl, pyridazinyl, oxazolyl oxazolidinyl, isoxazolyl, isoxazolidinyl, morpholinyl, thiazolyl, thiazolidinyl, isothiazolyl, quinoxazolinyl, isothiazolidinyl, quinolinyl, isoquinolinyl, benzimidazolyl, thiadazolyl, benzopyranyl, benzothiazolyl, benzoazolyl, furyl, tetrahydrofuryl, tetrahydropuranyl, thienyl (also referred to as thiophenyl), benzothiophenyl, oxadiazolyl, and furopyridyl.

The term "substituted heterocycle" (alternatively "substituted heterocyclic") refers to a heterocycle as defined above having one or more substituents independently selected from cyano, halo, hydroxy, $C_1$–$C_6$ alkyl, $C_1$–$C_6$ alkoxy, fluorinated $C_1$–$C_6$ alkyl, fluorinated $C_1$–$C_6$ alkoxy, aryl and the like.

The term "substituted" includes mono- and poly-substitution by a named substituent to the extent such single and multiple substitution is chemically allowed and results in a chemically stable compound.

When any variable or term occurs more than one time in any constituent or in Formula (I), its definition on each occurrence is independent of its definition at every other occurrence. Thus, for example, if $R^2$ and $R^3$ are both designated as "$C_1$–$C_4$ alkyl", $R^2$ and $R^3$ can represent the same or different alkyl groups embraced by the term.

Combinations of substituents and/or variables are permissible only if such combinations result in stable compounds.

The present invention includes pharmaceutical compositions useful for inhibiting HIV protease, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV protease, and a method of treating infection by HIV, or of treating AIDS or ARC. Additionally, the present invention is directed to a pharmaceutical composition comprising a therapeutically effective amount of a compound of the present invention in combination with a therapeutically effective amount of an HIV infection/AIDS treatment agent selected from:

(1) an HIV/AIDS antiviral agent,
(2) an anti-infective agent, and
(3) an immunomodulator.

The present invention also includes the use of a compound of the present invention as described above in the preparation of a medicament for (a) inhibiting HIV protease, (b) preventing or treating infection by HIV, or (c) treating AIDS or ARC.

The present invention further includes the use of any of the HIV protease inhibiting compounds of the present invention as described above in combination with one or more HIV infection/AIDS treatment agents selected from an HIV/AIDS antiviral agent, an anti-infective agent, and an immunomodulator for the manufacture of a medicament for (a) inhibiting HIV protease, (b) preventing or treating infection by HIV, or (c) treating AIDS or ARC, said medicament comprising an effective amount of the HIV protease inhibitor compound and an effective amount of the one or more treatment agents.

The compounds of the present invention may have asymmetric centers and may occur, except when specifically noted, as mixtures of stereoisomers or as individual diastereomers, or enantiomers, with all isomeric forms being included in the present invention.

The compounds of the present invention in a therapeutically effective amount are useful in the inhibition of HIV protease, the prevention or treatment of infection by human immunodeficiency virus (HIV) and the treatment of consequent pathological conditions such as AIDS. Treating AIDS or preventing or treating infection by HIV is defined as including, but to limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery. The compounds of the invention can also be used in "salvage" therapy; i.e., the compounds can be used to treat HIV infection, AIDS, or ARC in HIV-positive subject whose viral load achieved undetectable levels via conventional therapies employing known protease inhibitors, and then rebounded due to the emergence of HIV mutants resistant to the known inhibitors.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition, Thus the compounds of this invention are commercial products to be sold for these purposes.

The present invention also provides for the use of a compound of structural Formula (I) to make a pharmaceutical composition useful for inhibiting HIV protease and in the treatment of AIDS or ARC.

The compounds of the present invention may be administered in the form of pharmaceutically acceptable salts. The term "pharmaceutically acceptable salt" refers to all acceptable salts of the compounds of Formula (I) (in the form of water- or oil-soluble or dispersible products) and includes the conventional non-toxic salts or the quaternary ammonium salts which are formed, e.g., from inorganic or organic acids or bases. Examples of acid addition salts include acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like. Base salts include ammonium salts, alkali metal salts such as sodium and potassium salts, alkaline earth metal salts such as calcium and magnesium salts, salts with organic bases such as ethylenediamine, N-methylglutamine, N,N'-dibenzylethylene-diamine, chloroprocaine, diethanolamine, procaine, choline, N-benzylphenethylamine, diethylamine, piperazine, tris(hydroxymethyl) aminomethane, tetramethylammonium hydroxide, and dicyclohexylamine, and salts with amino acids such as arginine, lysine, ornithine, and so forth. Also, the basic nitrogen-containing groups may be quaternized with such agents as lower alkyl halides, such as methyl, ethyl, propyl, and butyl chlorides, bromides, and iodides; dialkyl sulfates such as dimethyl, diethyl, dipropyl, dibutyl, and diamyl sulfates; long chain halides such as decyl, lauryl, myristyl and stearyl chlorides, bromides, and iodides; and aralkyl halides such as benzyl and phenethyl bromides and others. The salt can be used as a dosage form for modifying the solubility or hydolysis characteristics of the compound or can be used in sustained release or pro-drug formulations.

Also, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intraveneous, intramuscular, intrasternal injection or infusion techniques), by inhalation spray, or rectally, in dosage unit formulations containing conventional non-toxic pharmaceutically-acceptable carriers, adjuvants and vehicles.

The term "administration" and variants thereof (e.g., "administering" a compound) in reference to a compound of the invention each mean providing the compound or a prodrug of the compound to the individual in need of treatment. When a compound of the invention or prodrug thereof is provided in combination with one or more other active agents (e.g., HIV/AIDS antivirals), "administration" and its variants are each understood to include concurrent and sequential provision of the compound or prodrug thereof and other agents.

Thus, in accordance with the present invention there is further provided a method of treating and a pharmaceutical composition for treating HIV infection and AIDS. The treatment involves administering to a subject in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results, directly or indirectly, from combination of the specified ingredients in the specific amounts.

By "pharmaceutically acceptable" it is meant the carrier, diluent or excipient must be compatible with the other ingredients of the formulation and not deleterious to the recipient thereof.

The term "subject," (alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

These pharmaceutical compositions may be in the form of orally-administrable suspensions or tablets, nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 0.01 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV protease inhibitor compounds with one or more agents useful in the treatment of HIV infection and AIDS. For example, the compounds of this invention may be effectively administered, whether at periods of pre-exposure and/or post-exposure, in combination with effective amounts of the HIV/AIDS antivirals, imunomodulators, antiinfectives, or vaccines, such as those in Table 1 as follows:

| Drug Name | Manufacturer | Indication |
| --- | --- | --- |
| ANTIVIRALS | | |
| 097 | Hoechst/Bayer | HIV infection, AIDS, ARC (non-nucleoside reverse transcriptase inhibitor) |
| Amprenavir 141 W94 GW 141 | Glaxo Wellcome | HIV infection, AIDS, ARC (protease inhibitor) |
| Abacavir GW 1592 1592U89 | Glaxo Welcome | HIV infection, AIDS, ARC (reverse transcriptase inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (−)6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, ADS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide | Peninsula Labs (Belmont, CA) | AIDS |

| Drug Name | Manufacturer | Indication |
|---|---|---|
| Sequence Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Squibb | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |

-continued

| Drug Name | Manufacturer | Indication |
|---|---|---|
| Total Enteral Nutrition | Norwich Eaton Pharmaceuticals | diarrhea and malabsorption related to AIDS |

It will be understood that the scope of combinations of the compounds of this invention will HIV/AIDS antivirals, immunomodulators, anti-infectives or vaccines is not limited to the list in Table 1 above, but includes in principle any combination with any pharmaceutical composition useful for the treatment of AIDS.

One preferred combination is a compound of the present invention and a nucleoside inhibitor of HIV reverse transcriptase such as AZT, 3TC, ddC, or ddI. Another preferred combination is a compound of the present invention and a non-nucleoside inhibitor of HIV reverse transcriptase, such as efavirenz, and optionally a nucleoside inhibitor of HIV reverse transcriptase, such as AZT, 3TC, ddC or ddI. Still another preferred combination is any one of the foregoing combinations further comprising an additional HIV protese inhibitor such as indinavir, Compound A, nelfinavir, ritonavir, saquinavir, amprenavir, or abacavir. A preferred additional inhibitor of HIV protease is the sulfate salt of indinavir. Other preferred additional protease inhibitors are nelfinavir and ritonavir. Still another preferred additional inhibitor of HIV protease is saquinavir which is administered in a dosage of 600 or 1200 mg tid.

Other preferred combinations include a compound of the present invention with the following (1) efavirenz, optionally with AZT and/or 3TC and/or ddI and/or ddC, and optionally with indinavir; (2) any of AZT and/or ddI and/or ddC and/or 3TC, and optionally with indinavir; (3) d4T and 3TC and/or AZT; (4) AZT and 3TC; and (5) AZT and d4T.

In such combinations the compound of the present invention and other active agents may be administered together or separately. In addition, the administration of one agent may be prior to, concurrent to, or subsequent to the administration of other agent(s). These combinations may have unexpected effects on limiting the spread and degree of infection of HIV.

Efavirenz is (–)-6-chloro-4-cyclopropylethynyl-4-trifluoromethyl-1,4-dihydro-2H-3,1-benzoxazin-2-one, also known as DMP-266 or SUSTIVA® (DuPont) or STOCRIN® (Merck). Efavirenz and its utility as an HIV reverse transcriptase inhibitor is described in U.S. Pat. No. 5,519,021 and in the corresponding PCT published application, WO 95/20389. Efavirenz can be synthesized by the protocol of U.S. Pat. No. 5,633,405. Additionally, the asymmetric synthesis of an enantiomeric benzoxazinone by a highly enantioselective acetylide addition and cyclization sequence is described in Thompson et al., *Tetrahedron Letters* 1995, 36: 8937–40, as well as in the PCT publication, WO 96/37457.

AZT is 3'-azido-3'-deoxythymidine, is also known as zidovudine, and is available from Burroughs-Wellcome under the tradename RETROVIR®. Stavudine is 2',3'-didehydro-3'-deoxythymidine, is also known as 2',3'-dihydro-3'-deoxythymidine and d3T, and is available from Bristol-Myers Squibb under the tradename ZERIT®. 3TC is (2R-cis)-4-Amino-1-[2-(hydroxymethyl)-1,3-oxathiolan-5-yl]-2(1H)-pyrimidinone, is also known as (–)-1-[(2R,5S)-2-(hydroxymethyl)-1,3-oxathiolan-5-yl]cytosine and lamivudine, and is available from Glaxo Wellcome under the tradename EPIVIR®. ddC is 2',3'-dideoxycytidine, is also known as zalcitabine, and is available from Hoffman LaRoche under the tradename HIVID®. ddI is 2',3'-dideoxyinosine, is also known as didanosine, and is available from Bristol-Myers-Squibb under the tradename VIDEX®. The preparation of ddC, ddI and AZT are also described in EPO 0,484,071.

Indinavir is N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide, and can be prepared as described in U.S. Pat. No. 5,413,999. Indinavir is generally administered as the sulfate salt at a dosage of 800 mg three times a day. Indinavir is available from Merck under the tradename CRIXIVAN®.

Compound A is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl)) pentaneamide, preferably administered as the sulfate salt. Compound A can be prepared as described in U.S. Pat. No. 5,646,148.

Ritonavir is [5S-(5R*,8R*,10R*,11R*)]-10-hydroxy-2-methyl-5-(1-methylethyl)-1-[2-(1-methylethyl)-4-thiazolyl]-3,6-dioxo-8,11-bis (phenylmethyl)-2,4,7,12-tetraazatridecan-13-oic acid 5-thiazolylmethyl ester, also known as 5-thiazolylmethyl [(aS)-a-[(1S,3S)-1-hydroxy-3-[(2S)-2-[3-[(2-isopropyl-4-thiazolyl) methyl]-3-methylureido]-3-methylbutyramido]-4-phenylbutyl] phenethyl]carbamate. It is available from Abbott under the tradename NORVIR®. Ritonavir can be prepared as described in U.S. Pat. No. 5,484,801.

Nelfinavir is [3S-[2(2S*,3S*),3a,4ab,8ab]]-N-(1,1-dimethylethyl) decahydro-2-[2-hydroxy-3-[(3-hydroxy-2-methylbenzoyl) amino]-4-(phenylthio)butyl]-3-isoquinolinecarboxamide monomethanesulfonate and VIRACEPT®, which is commercially available from Agouron. Nelfinavir can be prepared as described in U.S. Pat. No. 5,484,926.

Saquinavir is N-tert-butyl-decahydro-2-[2(R)-hydroxy-4-phenyl-3(S)-[[N-(2-quinolylcarbonyl)-L-asparaginyl] amino]butyl]-(4aS,8aS)-isoquinoline-3(S)-carboxamide, also known as INVIRASE®. Saquinavir can be prepared in accordance with procedures disclosed in U.S. Pat. No. 5,196,438. INVIRASE® (saquinavir mesylate) is available from Roche Laboratories. Saquinavir can be prepared as described in U.S. Pat. No. 5,196,438.

Amprenavir is 4-amino-N-((2 syn,3S)-2-hydroxy-4-phenyl-3-((S)-tetrahydrofuran-3-yloxycarbonylamino)-butyl)-N-isobutyl-benzenesulfonamide, also known as Compound 168 W94. Amprenavir is an aspartyl protease inhibitor that can be prepared by following the procedures described in U.S. Pat. No. 5,585,397. Amprenavir is available under the tradename AGENERASE® from Glaxo Wellcome. Amprenavir can be prepared as described in U.S. Pat. No. 5,783,701.

Abacavir is (1S,4R)-cis-4-[2-amino-6-(cyclopropylamino)-9H-purin-9-yl]-2-cyclopentene-1-methanol, also known as 1592U89. Abacavir can be prepared by following the protocol of EP 0434450.

Abbreviations used in the instant specification, particularly the Schemes and Examples, are as follows:

AcOH=acetic acid
AIB=aminoisobutyric acid
BOC or Boc=t-butyloxycarbonyl
CBZ=carbobenzoxy (alternatively, benzyloxycarbonyl)
DAST=(diethylamino)sulfur trifluoride
DCM=dichloromethane
DIEA=diisopropylethylamine DME=dimethoxyethane
DMF=dimethylformamide
DMSO=dimethyl sulfoxide
EDC=1-ethyl-3-(3-dimethylaminoproyl) carbodiimide
EtOAc=ethyl acetate
HBTU=1-hydroxybenzotriazole
HOAT=1-hydroxy-7-azabensotriazole
HOBT=1-hydroxy benzotriazole hydrate
LC=liquid chromatography
LDA=lithium diisopropyl amide
mCPBA=meta-chloroperbenzoic acid
MS=mass spectrometry
NMR=nuclear magnetic resonance
Ph=phenyl
TBAF=tetrabutylammonium fluoride
TBSCI=t-butyldimethylsilyl chloride
TFA=trifluoroacetic acid
THF=tetrahydrofuran
TLC=thin layer chromatography The compounds of the present invention can be readily prepared according to the following reaction schemes and examples, or modifications thereof using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicates, all variables are as defined above.

The preparation of the compounds of the present invention can be carried out in sequential or convergent synthetic routes, as shown in Schemes 1–6 below. A compound of Formula (I) can be prepared in accordance with Scheme 1, wherein Compound 1 is readily prepared via literature procedures described in Dorsey et al., *J. Med. Chem.* 1994, 37:3443–3451, and also in U.S. Pat. No. 5,413.999. Oxidation of compound 1 to acid 2 can be carried out by a number of methods known to those skilled in the art including oxidation with chromium trioxide in acetic acid. Amide coupling of compound 2 with an amine such as 3 is typically performed by the carbodiimide method with reagents such as EDC and HOBT in an inert solvent such as dichloromethane. Other methods of forming the amide or peptide bond include, but are not limited to, the synthetic routes via an acid chloride, azide, mixed anhydride or activated ester. Compound 4 is then hydrolyzed with aqueous lithium hydroxide and the resulting hydroxy acid 5 is conveniently protected with a standard silyl protecting group such as t-butyldimethyl silyl by reaction with either 5-butyldimethylsilyl chloride in the presence of imidazole in an inert solvent or the reaction with the silyl triflate and diisopropyl ethylamine again in an inert solvent such as dichloromethane. Mild aqueous hydrolysis of the silyl ester provides the protected hydroxy-acid 6 which is then coupled to $NH_2R^5$ using standard amide coupling reactions as described above to produce compound 7. The protecting group is removed with fluoride to arrive at compound 8.

As shown in Scheme 2, compounds of the invention of Formula (II) can be prepared in accordance with Scheme 1 by substituting the appropriate amine 9 for 3 in the amide coupling reaction with acid 2 to produce compound 10, which is then carried on to the desired compound 11.

SCHEME 1

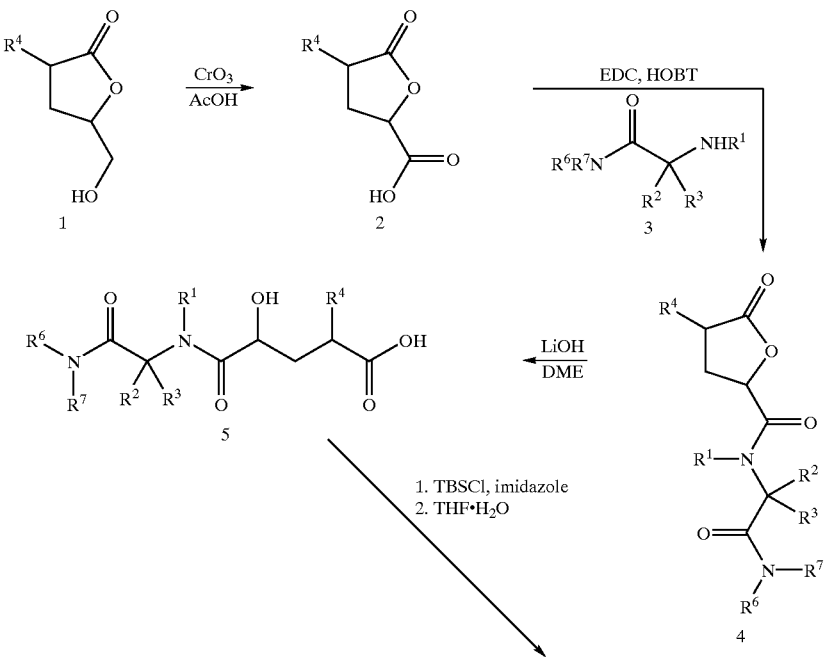

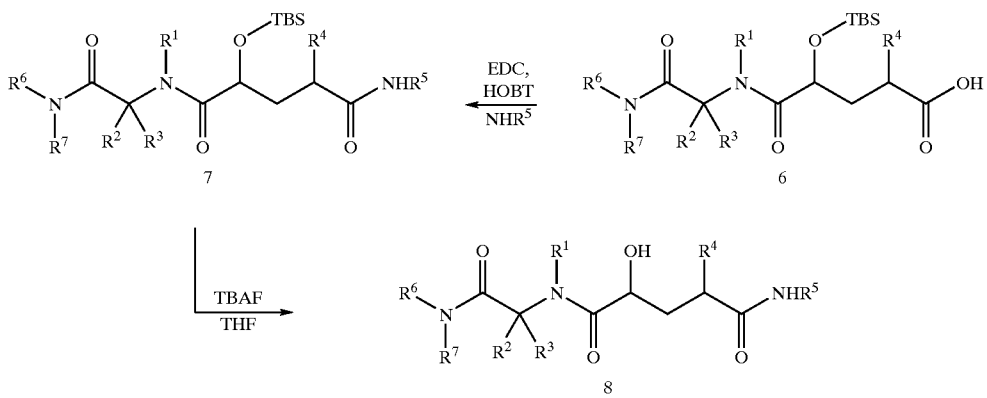

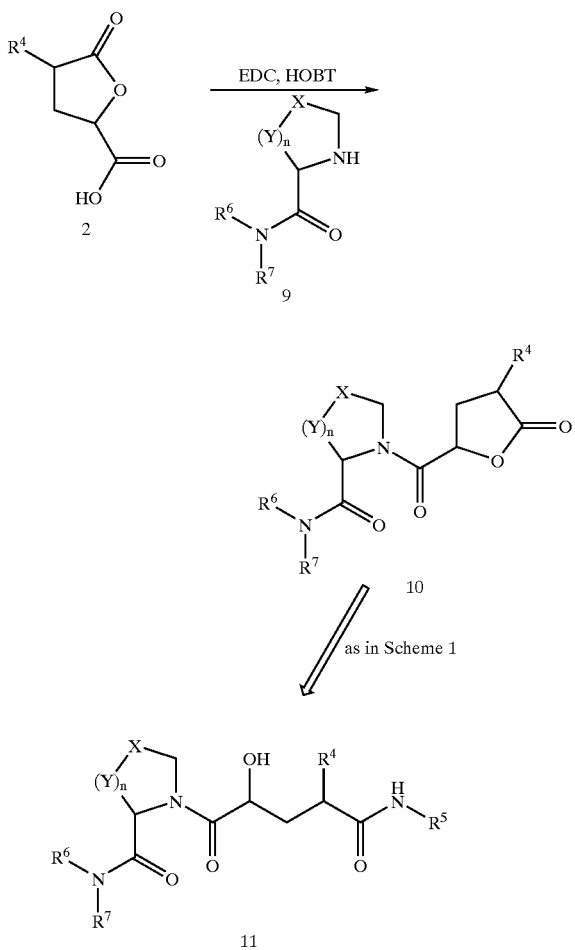

commercially available where the protecting group L is, for example, a BOC or CBZ group. Other suitably protected natural and unnatural amino acids can be prepared by literature methods including classical methods familiar to those skilled in the art, including Williams, *Synthesis of Optically Active α-Amino Acids*, 17, Pergamon Press, Oxford, 1989; and Williams, *Aldrichimica Acta* 1992, 25: 11–25.

Boc protecting groups can be removed by treatment with strong acids such as trifluoroacetic acid in dichloromethane or HCl in methanol. CBZ groups are readily removed by hydrogenolysis with a palladium catalyst under a hydrogen atmosphere in an alcoholic solvent such as methanol or ethanol. Removal of the protecting group can also be accomplished by a number of methods known in the art, such as those described in Greene, *Protective Groups in Organic Synthesis*, John Wiley and Sons, New York, 1991.

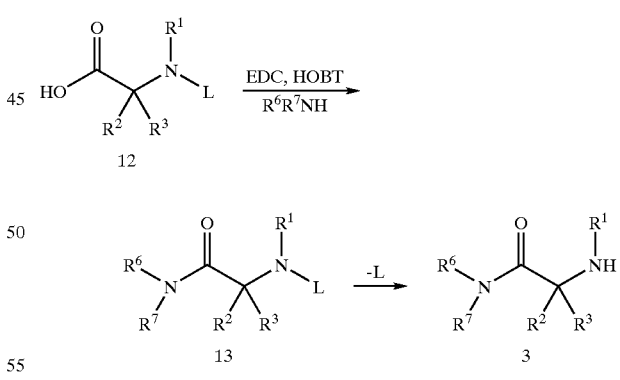

Intermediate compounds 3 can be produced by coupling a suitably protected amino acid such as 12 to an amine $NHR^6R^7$ using known amide coupling procedures as shown in Scheme 3 to produce 13. Removal of the protecting group then provides 3 which is ready for amide coupling. The desired protected amino acid derivatives are, in many cases, Chemical modifications of known amino acids provides another source of amines for coupling to acid 2 as exemplified by 4-hydroxyproline in Scheme 4. Amide coupling of $NHR^6R^7$ to 4-hydroxyproline as above provides 15. The chloro and fluoro compounds are available by treatment of 15 with $CCl_4$/$PPh_3$ or DAST as reported in *Bioorganic & Medicinal Chemistry* 1996, 4: 1365–1377. Acid removal of the BOC protecting group then provides 17 which can be elaborated to the compounds of interest according to the synthetic route described in Scheme 1.

SCHEME 4

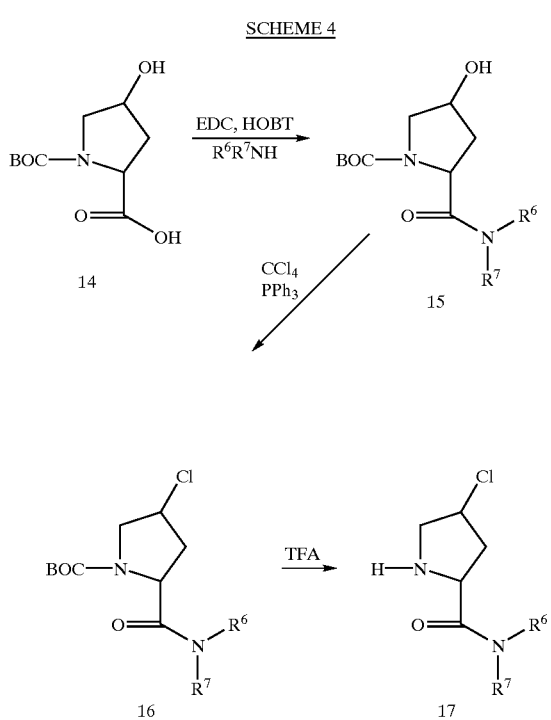

Intermediates of formula $NH_2R^5$ can be readily prepared via procedures set forth in the literature including, but not limited to, those found in *Tetrahedron Letters* 1991, 32: 711–714, *Tetrahedron Letters* 1995, 36: 3993–3996 and *Synthesis* 1998, 938–961.

A sequential synthetic route to the compounds of the invention is shown in Scheme 5. An amino acid allyl ester can be coupled to acid 2 using standard amide coupling chemistry as described above in Scheme 1. Removal of the allyl group is accomplished with a palladium catalyst in the presence of dimethylbarbituric acid and the resulting acid 20 can then be coupled to $NHR^6R^7$ to provide lactone 4.

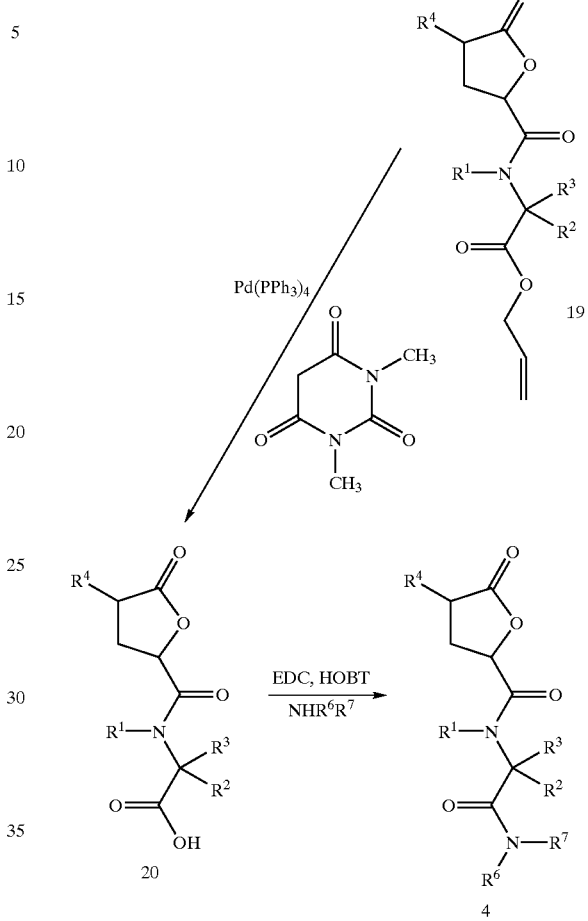

Another method for preparing intermediate 1 of the invention is shown in Scheme 6. Compound 21 can be prepared according to known procedures including those described in *Tetrahedron Letters* 1995, 36: 2195–2198. Iodolactonization of 21 provides 22 which is then converted into 1 by treatment with silver trifluoroacetate followed by base hydrolysis with sodium carbonate in methanol. Compound 1 is then elaborated to the compounds of interest as shown in Scheme 1.

SCHEME 5

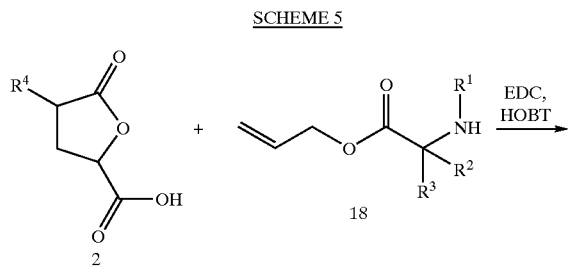

SCHEME 6

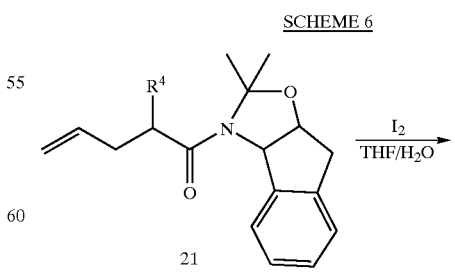

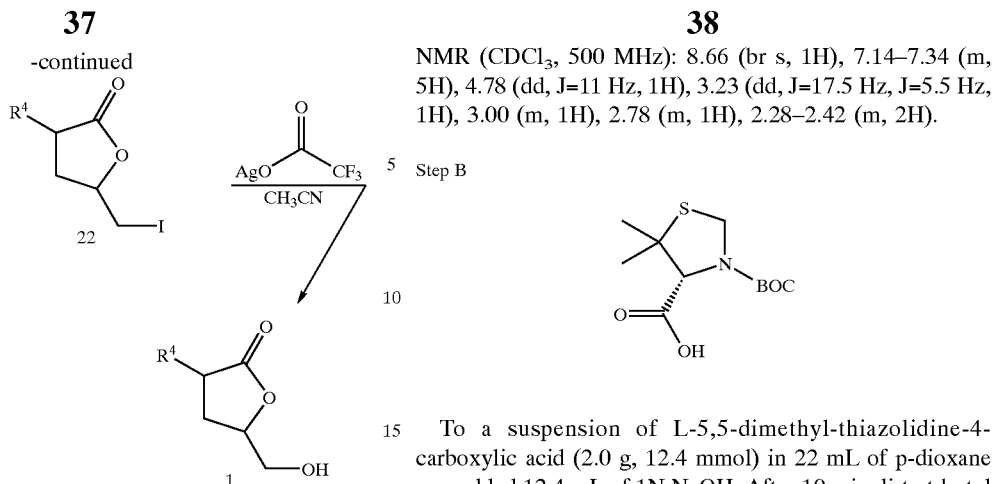

The following examples serve only to illustrate the invention and its practice. The examples are not to be constructed as limitations on the scope of spirit of the invention.

EXAMPLE 1

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2-methylphenyl) methyl]-4-thiazolidinecarboxamide

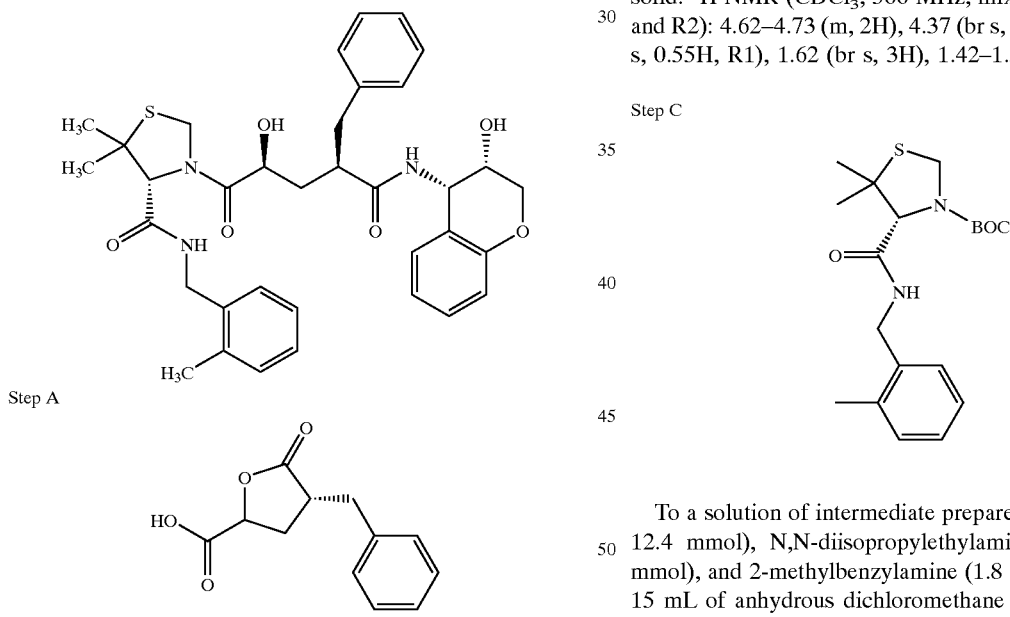

Step A

To a solution of the intermediate lactone alcohol (150 mg, 0.727 mmol), prepared as in *J. Med. Chem.* 1994, 37, 3443, in 5 mL of acetone was added 0.50 mL of Jones reagent (prepared from $CrO_3$ (26.72 g, 262 mmol), sulfuric acid (23 mL), and water (100 mL). The resulting rust-colored mixture was stirred at room temperature. After 5 hours, the starting material was consumed as evidenced by TLC. Ethyl alcohol (5 mL) was added and the resulting light blue reaction mixture was diluted with ethyl acetate (20 mL) and was washed with water (20 mL×2) and brine (20 mL). The organic layer was dried over anhydrous sodium sulfate and concentrated to give the tilted compound as a clear oil. The crude product was used without further purification. $^1$H NMR ($CDCl_3$, 500 MHz): 8.66 (br s, 1H), 7.14–7.34 (m, 5H), 4.78 (dd, J=11 Hz, 1H), 3.23 (dd, J=17.5 Hz, J=5.5 Hz, 1H), 3.00 (m, 1H), 2.78 (m, 1H), 2.28–2.42 (m, 2H).

Step B

To a suspension of L-5,5-dimethyl-thiazolidine-4-carboxylic acid (2.0 g, 12.4 mmol) in 22 mL of p-dioxane was added 12.4 mL of 1N NaOH. After 10 min di-tert-butyl dicarbonate (2.97 g, 13.64 mmol) was added and the resulting mixture was stirred at room temperature overnight. After approximately 20 hours the reaction mixture was concentrated in vacuo to half volume and was then diluted with 50 mL of ethyl acetate. The pH of the reaction mixture was adjusted to 2 by dropwise addition of aqueous sodium hydrogensulfate and the product extracted with ethyl acetate (50 mL×4). The organic layers were combined, washed with brine, dried over anhydrous sodium sulfate, filtered and concentrated in vacuo to give the titled compound as a white solid. $^1$H NMR ($CDCl_3$, 500 MHz, mixture of rotamers R1 and R2): 4.62–4.73 (m, 2H), 4.37 (br s, 0.45H, R2), 4.23 (br s, 0.55H, R1), 1.62 (br s, 3H), 1.42–1.54 (m, 12H).

Step C

To a solution of intermediate prepared in Step B (3.24 g, 12.4 mmol), N,N-diisopropylethylamine (6.48 mL, 37.2 mmol), and 2-methylbenzylamine (1.8 mL, 14.88 mmol) in 15 mL of anhydrous dichloromethane at 0° C. was added bromo-tri-pyrrolidin-phosphonium hexafluorophosphase (6.06 g, 13.02 mmol). The mixture was allowed to warm to room temperature and progress of reaction was monitored by TLC. After 4 hours the reaction was quenched with 10% aqueous citric acid and then diluted with 50 mL of dichloromethane. The organic layer was separated, washed with saturated aqueous sodium hydrogencarbonate and brine, dried over anhydrous sodium sulfate and concentrated in vacuo. The crude reaction mixture was purified by flash column chromatography on silica gel with 1:3 ethyl acetate/hexane as the eluant to give the titled compound as a white solid. $^1$H NMR ($CDCl_3$, 300 MHz): 7.15–7.27 (m, 4H), 6.12 (br s, 1H), 4.40–4.60 (m, 4H), 4.12 (m, 1H), 2.33 (s, 3H), 1.61 (s, 3H), 1.42 (m, 12H).

Step D

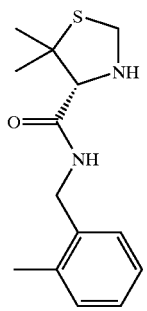

The intermediate prepared in Step C (4.20 g, 11.5 mmol) was dissolved in 10 mL of 30% trifluoroacetic acid/dichloromethane (v/v). The reaction mixture was stirred at room temperature and progress of reaction monitored by TLC. After 4 hours the reaction mixture was diluted with 60 mL of dichloromethane and was washed with saturated sodium hydrogencarbonate and brine, dried over anhydrous sodium sulfate and concentrated in vacuo to give the titled compound as a white solid. The product was used in Step E without further purification. $^1$H NMR (CDCl$_3$, 500 MHz): 7.18–7.28 (m, 4H), 6.75 (br s, 1H), 4.47 (d, J=5Hz, 2H), 4.20 (dd, J=5.5, J=10 Hz, 2H), 3.48 (s, 1H), 2.33 (s, 3H), 1.70 (s, 3H), 1.36 (s, 3H), LC-MS (M$^+$+1) (EI) 265.

Step E

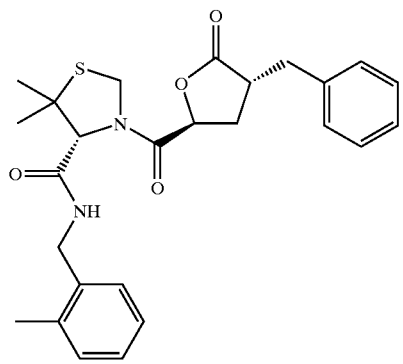

To a solution of the intermediate prepared in Step A (154 mg, 0.72 mmol), the intermediate prepared in Step D (190 mg, 0.72 mmol), and 1-hydroxybenzotriazole (150 mg, 1.11 mmol) in 2.5 mL of dichloromethane at 0° C. was added 1-[3-(dimethylamino)propyl]-3-ethylcarbodiimide hydrochloride (208 mg, 1.11 mmol). The mixture was allowed to warm to room temperature and progress of reaction was monitored by TLC. After 20 hours the crude reaction mixture was purified by preparatory TLC with 1:1 ethyl acetate/hexane as the eluant to give the titled compound as a white solid. $^1$H NMR (CDCl$_3$, 500 MHz, mixture of rotamers R1 and R2 0.55/0.45 ratio): 7.14–7.36 (m, 9H), 6.26 (br t, 0.45H, R2), 5.84 (br t, 0.55H, R1), 4.92 (m, 1H), 4.82 (m, 1H, R1 and R2), 4.69 (d, J=8 Hz, 0.55H, R1), 4.62 (d, J=11 Hz, 0.45 H, R2), 4.38–4.57 (m, 2H, R1 and R2), 4.32 (s, 0.55H, R1), 4.07 (s, 0.45H, R2), 3.28 (dd, J=14, J=14, J=4.5 Hz, 0.45H, R2), 3.10–3.19 (m, 1.1H), 2.88 (dd, J=12.5, J=7.5 Hz, 0.55H, R1), 2.78 (dd, J=12.5, J=7.5 Hz, 0.45H, R2), 2.56 (m, 0.45H, R2), 2.34 (s, 1.35H, R2), 2.32 (s, 1.65H, R1), 2.24 (m, 1H), 2.32 (m, 1H), 1.44–1.58 (m, 6H, R1 and R2), LC-MS (M$^+$+1) (EI) 467.

Step F

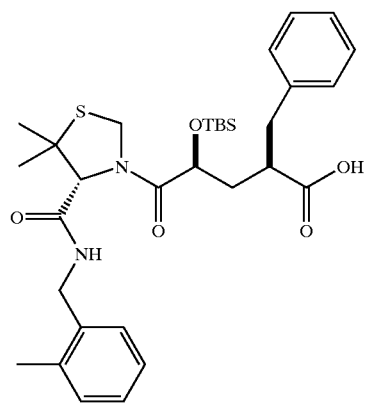

To a solution of the intermediate prepared in Step E (90 mg, 0.19 mmol) in 3 mL of p-dioxane was added a solution of lithium hydroxide monohydrate (9.0 mg, 0.21 mmol) in 2 mL of distilled water. The mixture was stirred at room temperature and progress of reaction was monitored by TLC. After 1 hour the reaction mixture was concentrated in vacuo. The product was azeotroped with toluene (10 mL×3) and dried under high vacuum. N,N-dimethylformamide (4 mL) was added followed by imidazole (196 mg, 2.88 mmol) and tert-butyldimethylsilyl chloride (230 mg, 1.50 mmol). The resulting solution was stirred at room temperature and reaction progress monitored by TLC. After 2 hours the reaction mixture was poured into a pH=7 buffer solution and the product was extracted with ethyl acetate (25 mL×3). The organic layers were combined, dried over anhydrous sodium sulfate and concentrated in vacuo to give the titled compound as an oil. The crude product was used in Step G without further purification. LC-MS (M$^+$1) (EI) 599.

Step G

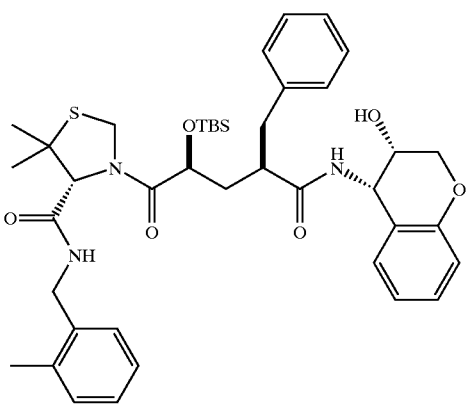

To a solution of intermediate prepared in Step F (115 mg, 0.19 mmol), cis-aminochromanol (36 mg, 0.22 mmol) prepared in Step L and 1-hydroxybenzotriazole (37 mg, 0.22 mmol) in 2 mL of anhydrous dichloromethane at 0° C. was added 1-[3-(dimethylamino)propyl]-3-ethylcarbodiimide hydrochloride (53 mg, 0.22 mmol). The reaction mixture was allowed to warm to room temperature and progress of reaction was monitored by TLC. After 20 hours the crude reaction mixture was purified by preparatory TLC with 45% ethyl acetate/hexane as the eluant to give the titled compound as a solid. $^1$H NMR (CDCl$_3$, 500 MHz, mixture of rotamers R1 and R2 0.55/0.45 ratio). 7.00–7.36 (m, 11H), 6.86–6.94 (m, 1H, R1 and R2), 6.76–6.83 (m, 1.45H), 5.84–5.89 (m, 1H), 5.68 (d, J=8 Hz, 0.55H, R1), 5.12 (dd, J=4.5, J=8 Hz, 0.55H, R1), 4.96 (dd, J=4.5, J=8 Hz, 0.45H, R2), 4.90 (d, J=9.5 Hz, 0.55H, R1), 4.82 (s, 0.55H, R1), 4.76 (d, J=9.5 Hz, 0.45H, R2), 4.72 (s, 0.45H, R2), 4.28–4.48 (m, 3H), 4.06 (br d, J=10.5 Hz, 0.55H, R1), 3.88–3.99 (m, 1.45H), 3.82 (m, 1H), 2.71–2.89 (m, 4H), 2.24–2.52 (m, 3.55H), 2.12 (m, 0.45H, R2), 1.80–1.89 (m, 1H), 1.43–1.58 (m, 6H), 0.84–0.93 (m, 9H), −0.05–.011 (m, 6H), LC-MS (M$^+$+1) (EI) 746.

Step H:

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2-methylphenyl) methyl]-4-thiazolidinecarboxamide To a solution of intermediate obtained in Step G (70 mg, 0.093 mmol) in 4 mL of anhydrous tetrahydrofuran was added tetrabutylammonium fluoride (93 μL, 0.10 mmol, 1.0M in tetrahydrofuran). The reaction mixture was stirred at room temperature and progress of reaction was monitored by TLC. After 2 hours the starting material was consumed and the reaction mixture was concentrated and purified by preparatory TLC with 96/4 dichloromethane/methanol as the eluant to give the titled compound as a white solid. $^1$H NMR (CDCl$_3$, 500 MHz, mixture of roamers R1 and R2 0.6/0.4 ratio): 7.06–7.36 (m 11H), 6.93–7.02 (m, 1.4H), 6.82–6.91 (m, 1H), 6.78 (d, J=7.5 Hz, 0.6H, R1), 5.78–5.89 (m, 1H), 5.14 (m, 0.4H, R2), 4.86–4.96 (m, 1.2H), 4.72–4.82 (m, 1H), 4.68 (s, 0.6H, R1), 4.53–4.62 (m, 1H), 4.40 (s, 0.4H, R2), 4.27 (m, 0.4H, R2), 3.88–4.06 (m, 4H), 3.68–3.76 (m, 1.4H), 3.48–3.54 (m, 1.6H), 3.02 (m, 0.6H, R1), 2.90 (m, 1H), 2.70–2.81 (m, 2.4H), 2.32 (s, 1.2H, R2), 2.02–2.14 (m, 2.4H), 1.44–1.68 (m, 6.4H), LC-MS (M$^+$+1) (EI) 632.

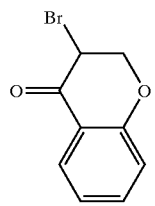

Step I

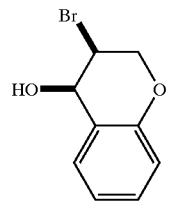

To a solution of 4-chloromanone (10 g, 67.49 mmol) in 400 mL dichloromethane at 0° C. was added bromine (4.45 mL, 86.39 mmol) dropwise slowly. The reaction was monitored by TLC. After half an hour the reaction mixture was diluted with methylene chloride (100 mL) and was washed with water (300 mL). The organic layer was dried over anhydrous sodium sulfate and concentrated. The resulting product was dissolved in HOAc (100 mL) and sodium sulfate (8 g) was added. The reaction mixture was stirred at room temperature and reaction progress was monitored by TLC. After 48 hours the reaction mixture was poured into water and the product was extracted with methylene chloride. The organic layer was dried over anhydrous sodium sulfate and concentrated in vacuo to give the titled compound as a white solid. $^1$H NMR (CDCl$_3$, 400 MHz): 7.93 (d, J=8.8 Hz, 1H), 7.54 (t, 1H), 7.08 (t, 1H), 7.02 (d, J=8.0 Hz, 1H), 4.63 (m, 4H)

Step J

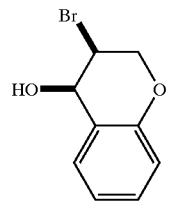

To a solution of 3-bromo-4-chromanone (2 g, 8.81 mmol) in methanol (20 mL) was added sodium borohydride (0.4 g, 10.57 mmol). The reaction was stirred at room temperature and monitored by TLC. After 2 hours the solvent was removed in vacuo and then diluted with ethyl acetate (50 mL). The resulting solution was washed with brine, dried over anhydrous sodium sulfate, filtered and concentrated in vacuo to give the titled compound as a white solid. $^1$H NMR (CDCl$_3$, 300 MHz): 7.32 (d, J=7.2 Hz, 1H), 7.23 (t, 1H), 6.96 (t, 1H), 6.84 (d, J=9.0 Hz, 1H), 4.82 (m, 1H), 4.54 (m, 1H), 4.38 (m, 2H).

Step K

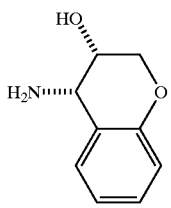

To a solution of 3-bromo-4-chromanol (2 g, 8.72 mmol) in acetonitrile (20 mL) was added concentrated sulfuric acid (1 mL, 17.47 mol). The reaction mixture was stirred at 45° C.–50° C. for 18 hours. The solvent was removed in vacuo. Then water (10 mL) was added. The reaction mixture was heated to reflux. After 5 hours the reaction mixture was cooled to room temperature. The pH of the reaction mixture was adjusted to 12–13 by dropwise addition of aqueous 50% sodium hydroxide. The product was extracted with tetrahydrofuran three times. The organic layer were combined and dried over anhydrous sodium sulfate, filtered and concentrated in vacuo to give the title compound as a white solid. $^1$H NMR (CDCl$_3$, 300 MHz): 7.29 (d, J=7.8 Hz, 1H), 7.16 (t, 1H), 6.93, (t,1H), 6.83 (d, J=8.4 Hz, 1H), 4.12 (m, 1H), 3.99 (m, 2H), 3.84 (m, 1H).

Step L

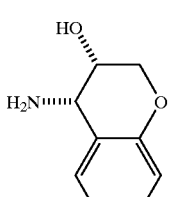

To a suspension of the racemic 4-amino-3-chromal in ethanol (35 mL per gram of 4-amino-3-chromanol) was added 1.0 equivalent of (S)-(+) mandelic acid. The suspension was heated to 70° C. until forming a homogeneous solution. The solution was cooled to room temperature and white crystal was formed. After filtering the white crystal was dissolved in 3N aqueous sodium hydroxide solution and the resolved product was extracted with ethyl acetate three times. The combined organic layer was dried over anhydrous sodium sulfate, filtered and concentrated in vacuo to give the titled compound as a white solid. The purity of the compound was verified by chiral HPLC with Crownpak CR+column eluted with pH 1.0 perchloric acid solution. $^1$H NMR (CDCl$_3$, 300 MHz): 7.29 (d, J=7.8 Hz, 1H), 7.16 (t, 1H), 6.93, (t, 1H), 6.83 (d, J=8.4 Hz, 1H), 4.12 (m, 1H), 3.99 (m, 2H), 3.84 (m, 1H).

EXAMPLE 2

(4R)-3-[(2S,4R)-5-[((3S,4S)-3,4-dihydro-3-hydroxy-2H-1-benzopyran-4-yl)amino]-2-hydroxy-1,5-dioxo-4-phenylmethyl)pentyl]-5,5-dimethyl-N-(2,2,2-trifluoroethyl)-4-thiazolidinecarboxamide

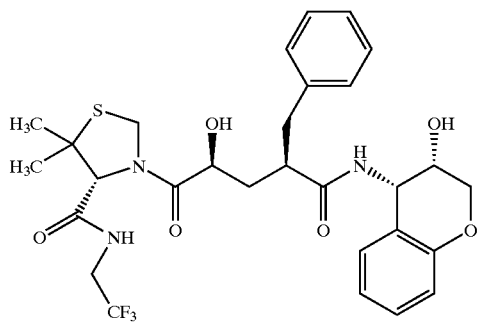

Step A

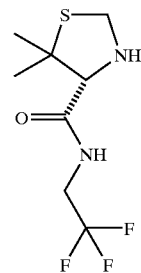

To a solution of of L-5,5-dimethyl-thiazolidine-4-carboxylic acid (200 mg, 1.24 mmol), 1-hydroxybenzotriazole (160 mg, 1.24 mmol) and 2,2,2-trifluoroethylamine (0.147 mL, 1.86 mmol) in 30 mL of anhydrous dichloromethane at 0° C. was added 1-[3-(dimethylamino)propyl]-3-ethylcarbodiimide hydrochloride (ED) (350 mg, 1.86 mmol). A white precipitate formed immediately upon addition of EDC. The reaction was allowed to warm to room temperature and progress of reaction was monitored by TLC. After 2 hours the solvent was removed in vacuo. The crude reaction mixture was purified by flash column chromatography on silica gel with 1:1 ethyl acetate/hexane as the eluant to give the titled compound as a white crystalline solid. $^1$H NMR (CDCl$_3$, 400 MHz); 7.30 (br s, 1H), 4.28 (d, J=9.5 Hz, 1H), 4.19 (d, J=9.5 Hz, 1H), 3.80–4.00 (m, 2H), 3.60 (s, 1H), 1.70 (s, 3H), 1.39 (s, 3H), LC-MS (M$^+$+1(EI) 243.

Step B

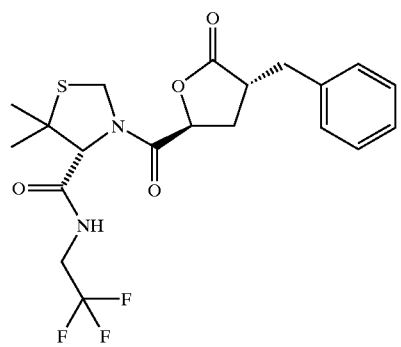

The titled compound was obtained following the procedure described in Example 1, Step E starting with intermediate prepared as in Example 1, Step A (168 mg, 0.76 mmol) and intermediate prepared in Step A (184 mg, 0.176 mmol). $^1$H NMR (CDCl$_3$, 400 MHz, mixture of rotamers R1 and R2 0.6/0.4 ratio): 7.14–7.36 (m, 5H), 6.32 (m, 0.4H, R2), 6.22 (m, 0.6H, R1), 4.76–4.94 (m, 1.6H), 4.46–4.72 (m, 1H), 4.50 (m, 0.4H, R2), 4.30–4.36 (m, 1H), 4.04–4.22 (m, 1H), 3.67–3.77 (m, 1H), 2.96–3.28 (m, 1.6H), 2.74–2.88 (m, 1H) 2.54–2.62 (m, 0.4H, R2), 2.04–2.35 (m, 2H), 1.42–1.58 (m, 6H), LC-MS (M$^+$+1) (EI) 445.

Step C

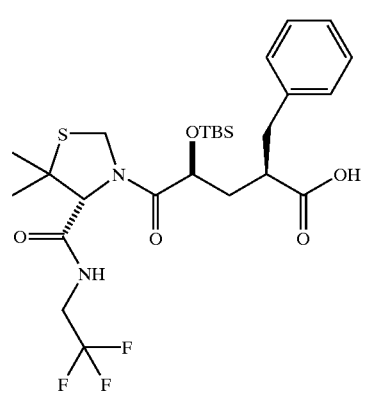

The titled compound was obtained following the procedures described in Example 1, Step F starting with the intermediate prepared in Step B (107 mg, 0.24 mmol) in this example. The crude product was used in Step D without further purification. LC-MS (M$^+$+1) (EI) 577.

Step D

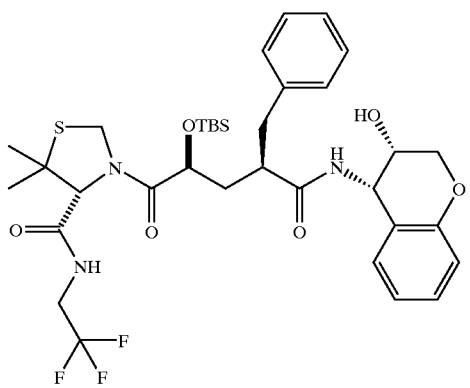

The titled compound was obtained following the procedure described in Example 1, Step G starting with the intermediate prepared in Step C (138 mg, 0.24 mmol) of this example. LC-MS (M$^+$+1) (EI) 724.

Step E:

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(2,2,2-trifluoroethyl)-4-thiazolidine-carboxamide The titled compound was obtained following the procedure described in Example 1, Step H starting with the intermediate prepared in Step D (62 mg, 0.085 mmol) of this example. $^1$H NMR (CDCl$_3$, 400 MHz, mixture of rotamers R1 and R2 0.55/0.45 ratio): 7.10–7.40 (m, 7.45H), 6.88–6.98 (m, 1.45H), 6.82 (t, J=8 Hz, 0.55H, R1), 6.11 (br t, 0.55H, R1), 5.98 (d, J=7.5 Hz, 0.55H, R1), 5.88 (d, J=7.5 Hz, 0.45H, R2), 5.20 (m, 1H), 4.86–4.95 (m, 1.55H), 4.77 (s, 0.45H, R2), 4.66 (d, J=9.5 Hz, 0.55H, R1), 4.43 (s, 0.55H, R1), 4.34 (br, d, J=9.5 Hz, 0.45H, R2), 3.96–4.22 (m, 3H), 3.62–3.78 (m, 1.45H), 3.22–3.32 (m, 1H), 2.80–3.09 (m, 2.45H), 2.29 (m, 0.45H, R2), 2.12 (m, 0.55H, R1), 1.58–1.72 (m, 3.55H), 1.46–1.52 (m, 3H), LC-MS (M$^+$+1) (EI) 610.

EXAMPLE 3

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl]-5,5-dimethyl-N-[(2-methylphenyl)-methyl]-4-thiazolidinecarboxamide

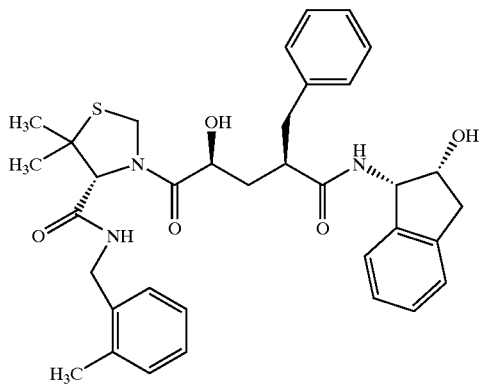

Step A

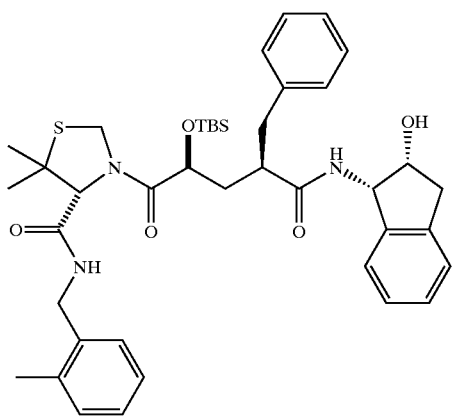

To a solution of the intermediate prepared as in Example 1, Step F (141 mg, 0.23 mmol), cis-aminoindanol (39 mg, 0.26 mmol), N,N-diisopropylethylamine (26 μL, 0.35 mmol) and 1-hydroxy-7-azabenzotriazole (50 mg, 0.35 mmol) in 2 mL of anhydrous dichloromethane at 0° C. was added 1-[3-dimethylamino)propyl]-3-ethylcarbodiimide hydrochloride (68 mg, 0.35 mmol). The reaction mixture was allowed to warm to room temperature and progress of reaction was monitored by TLC. After 2 hours the crude reaction mixture was purified by preparatory TLC with 1:1 ethyl acetate/hexane as the eluant to give the titled compound as a white solid. $^1$H NMR (CDCl$_3$, 500 MHz, mixture of rotamers R1 and R2 0.55/0.45 ratio): 7.12–7.36 (m, 12H), 7.04 (m, 0.55H, R1), 6.95 (m, 0.45H, R2), 6.85 (br t, 0.45H, R2), 5.96 (br t, 0.55H, R1), 5.79 (d, J=7.5 Hz, 0.55H, R1), 5.70 (d, J=7.5 Hz, 0.45H, R2), 5.22 (dd, J=8, J=5 Hz, 0.55H, R1), 5.02 (dd, J=8, J=5 Hz, 0.45H, R2), (d, J=9.5 Hz, 0.55H, R1), 4.72–4.86 (m, 2H), 4.20–4.50 (m, 3.45H), 2.70–3.06 (m, 4H), 2.10–2.35 (m, 5H), 1.84 (m, 1H), 1.42–1.58 (m, 7H), 0.94 (s, 4.05H, R2), 0.86 (s, 4.95H, R1), −0.04–0.15 (m, 6H, R1 and R2), LC-MS (M$^+$+1) (EI) 730.

Step B:

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl]-5,5-dimethyl-N-[(2-methylphenyl)-methyl]-4-thiazolidinecarboxamide The titled compound was obtained following the procedure described in Example 1, Step H starting with the intermediate prepared in Step A (45 mg, 0.061 mmol) of this example. $^1$H NMR (CDCl$_3$, 500 MHz, mixture of rotamers R1 and R2 0.6/0.4 ratio): 7.12–7.38 (m, 12H), 6.90–7.05 (m, 2H), 5.80 (m, 1H), 5.27 (dd, J=8.5, J=5Hz, 0.4H, R2), 4.84–4.98 (m, 2.6H), 4.75 (s, 0.6H, R1), 4.56–4.65 (m, 1H), 4.44 (s, 0.40H, R2), 4.26–4.34 (m, 1H), 4.20 (br t, J=3 Hz, 0.4H, R2), 3.92–4.08 (m, 1.6H), 3.47–3.56 (m, 1H), 2.50–3.04 (m, 5H), 2.34 (s, 1.2H, R2), 2.06–2.18 (m, 1H), 2.02 (s, 1.8H, R1), 1.54–1.74 (m, 8H), LC-MS (M$^+$+1) (EI) 616.

EXAMPLE 4

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl]-5,5-dimethyl-N-(2,2,2-trifluoroethyl)-4-thiazolidinecarboxamide

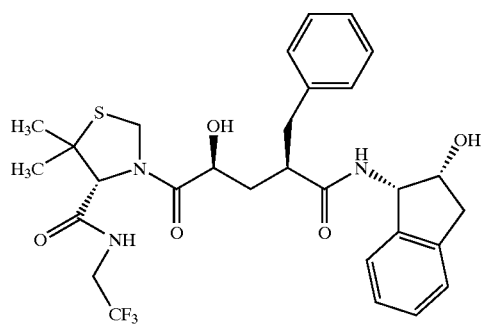

Step A

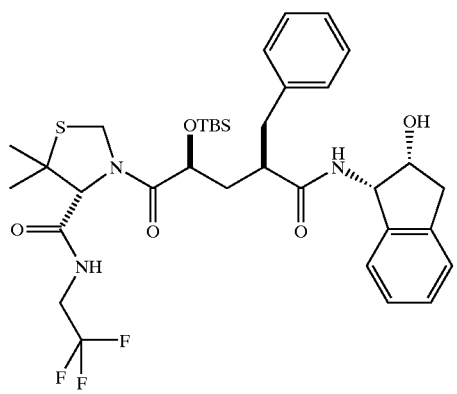

The titled compound was obtained following the procedure described in Example 3, Step A starting with the intermediate prepared as in Example 2, Step C (138 mg, 0.24 mmol). $^1$H NMR (CDCl$_3$, 500 MHz, mixture of rotamers R1 and R2 0.6/0.4 ratio): 7.16–7.38 (m, 9.4H), 6.26 (br t, 0.6H, R1), 5.83 (d, J=9 Hz, 0.6H, R1), 5.79 (d, J=9 Hz, 0.4H, R2), 5.31 (dd, J=8.5, J=5 Hz, 0.4H, R2), 5.21 (dd, J=8.5, J=5 Hz, 0.6H, R1), 5.00 (d, J=9 Hz, 0.6H, R1), 4.79–4.88 (m, 2.2H), 4.44 (t, J=6.5 Hz, 0.6H, R1), 4.37 (s, 0.6H, R1), 4.24–4.32 (m, 1.6H), 3.98–4.05 (m, 0.6H, R1), 3.79–3.88 (m, 1.4H), 3.66–3.74 (m, 0.4H, R2), 3.02–3.11 (m, 1H), 2.80–2.98 (m, 3.4H), 2.69–2.75 (m, 0.6H, R1), 2.34–2.42 (m, 0.6H, R1), 2.30–2.38 (m, 0.4H, R2), 1.81–1.93 (m, 1H), 1.56–1.62 (m, 3H), 1.44–1.47 (m, 3H), 0.88–0.94 (m, 9H), −0.02–0.12 (m, 6H), LC-MS (M$^+$+1) (EI) 708.

Step B:

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl]-5,5-dimethyl-N-(2,2,2-trifluoroethyl)-4-thiazolidinecarboxamide The titled compound was obtained following the procedure described in Example 1, Step H starting with intermediate prepared in Step A (55 mg, 0.078 mmol) of this example, $^1$H NMR (CDCl$_3$, 500 MHz, mixture of rotamers R1 and R2 0.6/0.4 ratio): 7.14–7.42 (m, 9H), 6.94 (d, J=7 Hz, 0.6H, R1), 6.21 (br t, 0.4H, R2), 6.02 (d, J=10 Hz, 0.6H, R1), 5.90 (d, J=10 Hz, 0.4H, R2), 5.28 (m, 1H, R1 and R2), 4.88–4.96 (m, 1.6H), 4.81 (s, 0.6H, R1), 4.65 (d, J=9.5 Hz, 0.4H, R2), 4.45 (s, 0.4H, R1), 4.34 (m, 0.4H, R1), 4.11–4.26 (m, 2H), 3.96 (m, 0.6H, R1), 3.64–3.74 (m, 0.4H, R2), 3.45–3.54 (m, 1H), 2.80–3.20 (m, 5.6H), 2.29 (m, 0.4H, R2), 2.13 (t, J=12.5 Hz, 0.6H, R1), 1.58–1.74 (m, 4H), 1.48–1.52 (m, 3H), LC-MS (M$^+$+1) (EI) 594.

EXAMPLE 5

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(1,1-dimethylethyl)-4-thiazolidinecarboxamide

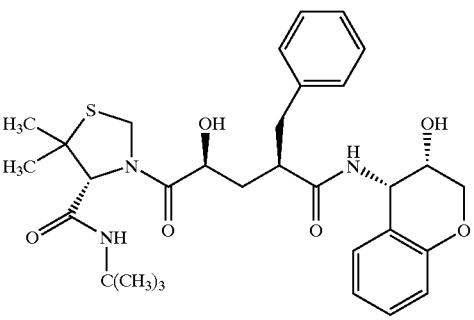

Step A

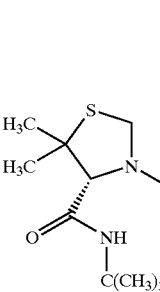

The titled compounds was obtained following the procedure described in Example 2, Step A starting with tert-butylamine (4.0 mL, 38 mmol) and L-5,5-dimethyl-thiazolidine-4-carboxylic acid (1.55 g, 9.6 mmol). $^1$H NMR (CDCl$_3$, 500 MHz): 6.33 (br s, 1H), 4.27 (d, J=9.5 Hz, 1H), 4.18 (d, J=9.5 Hz, 1H), 3.34 (s, 1H), 1.50 (s, 3H), 1.38 (s, 9H), 1.35 (s, 3H).

Step B

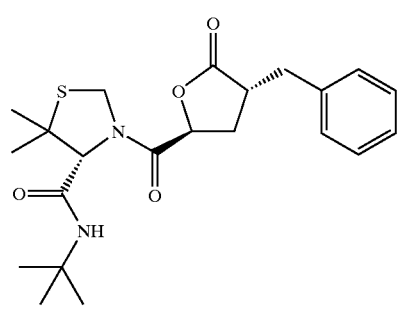

To a solution of intermediate prepared in Step A (250 mg, 1.2 mmol), the intermediate prepared as in Example 1, Step A (500 mg, 2.3 mmol), N,N-diisopropylethylamine (210 μL, 1.2 mmol) and 1-hydroxy-7-azabenzotriazole (315 mg, 2.3 mmol) in 4 mL of anhydrous dichloromethane at 0° C. was added 1-[3-(dimethylamino)propyl]-3-ethylcarbodiimide hydrochloride (440 mg, 2.3 mmol). The reaction mixture was allowed to warm to room temperature and progress of the reaction was monitored by TLC. After 22 hours the crude reaction mixture was purified by flash column chromatography on silica gel with 1:1 ethyl acetate/hexane as the eluant to give the titled compound as a white crystalline solid. $^1$H NMR (CDCl$_3$, 500 MHz, mixture of rotamers R1 and R2): 7.18–7.36 (m, 5H), 5.92 (br s, 0.5H), 5.73 (br s, 0.5H), 4.78–4.98 (m, 2H), 4.69 (d, J=8.5 Hz, 0.5H), 4.60 (d, J=11.5 Hz, 0.5H), 4.20 (s, 0.5H), 3.08–3.30 (m, 2H), 2.83 (dd, J=13.5, J=8.5 Hz, 0.5H), 2.75 (dd, J=13.5, J=8.5 Hz, 0.5H), 2.60 (m, 0.5H), 2.12–2.30 (m, 1.5H), 1.43–1.54 (m, 6H), 1.28–1.38 (m, 9H), LC-MS (M$^+$+1) (EI) 419.

Step C

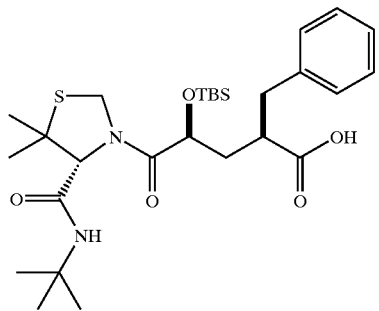

The titled compound was obtained following the procedure described in Example 1, Step F starting with intermediate prepared in Step B (320 mg, 0.77 mmol) of this example. The crude product was used in Step D without further purification. LC-MS (M$^+$+1) (EI) 551.

Step D

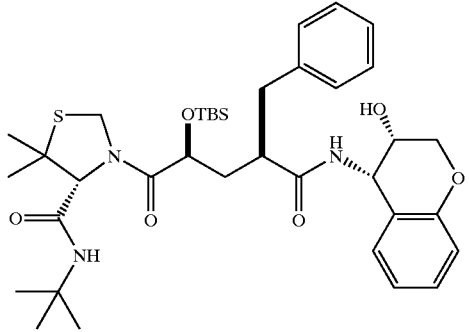

The titled compound was obtained following the procedure described in Example 3, Step A starting with the intermediate prepared in Step C (210 mg, 0.39 mmol) of this example and cis-aminochromanol (75 mg, 0.45 mmol). $^1$H NMR (CDCl3, 500 MHz, mixture of rotamers 1:1 ratio): 7.12–7.37 (m, 7H), 6.89 (m, 1H), 6.80 (t, J=8 Hz, 1H), 6.21 (s, 0.5H), 5.82 (d, J=8 Hz, 0.5H), 5.72 (d, J=8Hz, 0.5H), 5.51 (s, 0.5H), 5.33 (m, 0.5H), 5.14 (m, 0.5H), 4.93 (d, J=9.5 Hz, 0.5H), 4.76–4.82 (m, 1.5H), 4.49 (m, 1H), 4.32 (d, J=8.5 Hz, 0.5H), 4.23 (s, 0.5H), 4.03–4.16 (m, 1H), 3.90–3.98 (m, 1.5H), 3.82 (m, 0.5H), 2.78–2.94 (m, 3H), 2.45 (d, J=5.5 Hz, 0.5H), 2.28–2.36 (m, 1H), 2.14 (m, 0.5H), 1.92 (m, 0.5H), 1.82 (m, 0.5H), 1.46–1.58 (m, 6H), 1.28–1.38 (m. 9H), 0.86–0.94 (m, 9H), −0.06–0.14 (m, 6H), LC-MS (M$^+$+1) (EI) 698.

Step E:

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(1,1-dimethylethyl)-4-thiazolidinecarboxamide The titled compound was obtained following the procedure described in Example 1, Step H starting with intermediate prepared in Step D (80 mg, 0.11 mmol) of this example $^1$H NMR (CDCl$_3$, 500 MHz, mixture of rotamers 1:1 ratio): 7.22–7.38 (m, 5H), 7.12–17.18 (m, 2), 6.90 (m, 1H), 6.80 (d, J=8 Hz, 1H), 6.17 (br s, 0.5H), 5.81 (d, J=8 Hz, 1H), 5.48 (br s, 0.5H), 5.29 (dd, J=8.5, J=4 Hz, 0.5H), 5.19 (dd, J=8.5, J=4 Hz, 0.5H), 4.94 (d, J=10 Hz, 0.5H), 4.80–4.88 (m, 1H), 4.64 (d, J=9 Hz, 0.5H), 4.40 (s, 0.5H), 4.35 (m, 0.5H), 4.24 (s, 0.5H), 3.96–4.12 (m, 3.5H), 3.73–3.84 (m, 1H), 3.52 (d, J=7.5 Hz, 0.5H), 3.38 (d, J=7.5 Hz, 0.5H), 2.82–3.05 (m, 2H), 2.31 (m, 0.5H), 2.11 (m, 0.5H), 2.01 (d, J=6 Hz, 0.5H), 1.81 (d, J=6 Hz, 0.5H), 1.50–1.70 (m, 7H), 1.26–1.36 (m, 9H), LC-MS (M$^+$+1) (EI) 584.

EXAMPLE 6

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl)]-5,5-dimethyl-N-(1,1-dimethylethyl)-4-thiazolidinecarboxamide

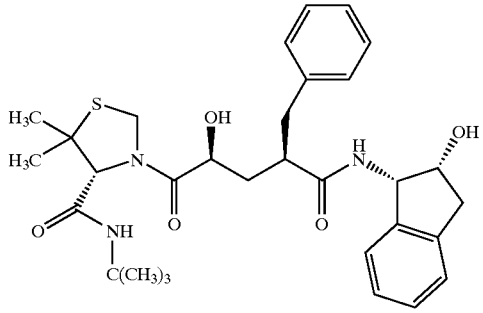

Step A

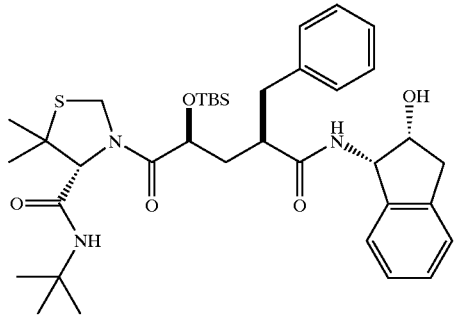

The titled compound was obtained following the procedure described in Example 3, Step A starting with the intermediate prepared as in Example 5, Step C (210 mg, 0.39 mmol). $^1$H NMR (CDCl$_3$, 500 MHz, mixture of rotamers R1 and R2 1:1 ratio): 7.16–7.38 (m, 9H), 6.38 (br s, 0.5H), 5.77 (m, 1H), 5.56 (br s, 0.5H), 5.39 (dd, J=9, J=5 Hz, 0.5H), 5.24 (dd, J=9, J=5 Hz, 0.5H), 4.98 (d, J=9.5 Hz, 0.5H), 4.76–4.86 (m, 1.5H), 4.48–4.56 (m, 1H), 4.23–4.35 (m, 2H), 3.04 (m, 1H), 2.56–2.98 (m, 4H), 2.34 (m, 0.5H), 1.92 (m, 0.5H), 1.84 (m, 0.5H), 1.44–1.56 (m, 6H), 1.24–1.38 (m, 10H), 0.90 (m, 9H), 0.02–0.16 (m, 6H), LC-MS (M$^+$+1) (EI) 682.

Step B:

(4R)-3-[(2S,4R)-5-[((1S,2R)-2,3-dihydro-2-hydroxy-1H-inden-1-yl)amino]-2-hydroxy-1,5-dioxo-4-(phenylmethyl)

pentyl]-5,5-dimethyl-N-(1,1-dimethylethyl)-4-thiazolidinecarboxamide

The titled compound was obtained following the procedure described in Example 1, Step H starting with the intermediate prepared in Step A (200 mg, 0.29 mmol) of this example. $^1$H NMR (CDCl$_3$, 500 MHz, mixture of rotamers 1:1 ratio): 7.10–7.40 (m, 9H), 6.26 (br s, 0.5H), 5.85 (m, 1H), 5.52 (br s, 0.5H), 5.38 (dd, J=9., J=4Hz, 0.5H), 5.30 (dd, J=9, J=4 Hz, 0.5H), 4.86–4.96 (m, 1.5H), 4.64 (d, J=9.5 Hz, 0.5H), 4.48 (s, 0.5H), 4.35 (br d, J=11 Hz, 0.5H), 4.20–4.26 (m, 1.5H), 4.08 (br d, J=11 Hz, 0.5H), 3.48–3.54 (m, 1H), 2.78–3.08 (m, 5H), 2.31 (m, 0.5H), 2.12 (t, J=12.5 Hz, 0.5H), 1.48–1.72 (m, 7H), 1.20–1.40 (m, 9H), LC-MS (M$^+$+1) (EI) 568.

EXAMPLE 7

(4R)-3-[(2S,4R)-5-[((1S,2R,5R)-5-methyl-2-hydroxy-1-cyclopentyl)amino]-2-hydroxy-1,5-dioxo-4-(phenylmethyl)pentyl]-5,5-dimethyl-N-[(2-methylphenyl)-methyl]-4-thiazolidinecarboxamide

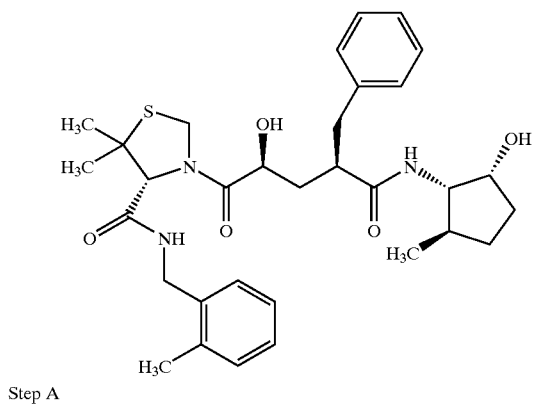

Step A

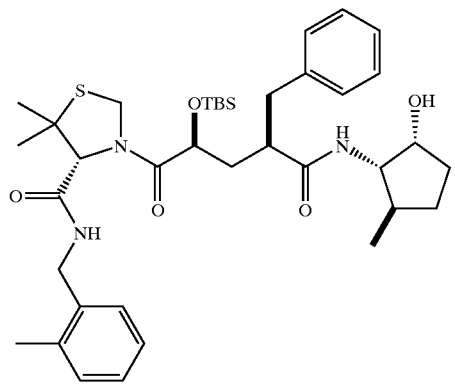

To a solution of the intermediate prepared as in Example 1, Step F (146 mg, 0.24 mmol), 2-amino-3-methylcyclohexanol (34 mg, 0.30 mmol), N,N-diisopropylethylamine (63 μL, 0.36 mmol) and 1-hydroxy-7-azabenzotriazole (50 mg, 0.35 mmol) in 2 mL of anhydrous dichloromethane at 0° C. was added 1-[3-(dimethylamino)propyl]-3-ethylcarbodiimide hydrochloride (70 mg, 0.37 mmol). The reaction mixture was allowed to warm to room temperature and progress of reaction was monitored by TLC. After 4 hours the crude reaction mixture was purified by preparatory TLC with 1:1 ethyl acetate/hexane as the eluant to give the titled compound as a white solid. $^1$H NMR (CDCl$_3$, 500 MHz, mixture of rotamers R1 and R2 0.65/0.35): 7.14–7.38 (m, 9H), 6.85 (br t, 0.35H, R2), 5.96 (br t, 0.65H, R1), 5.26 (m, 1H, R1 and R2), 4.90 (d, J=9.5 Hz, 0.65H, R1), 4.78–4.84 (m, 1H, R1 and R2), 4.63–4.72 (m, 0.7H), 4.22–4.56 (m, 4.65H), 3.64–3.74 (m, 1H, R1 and R2), 3.48 (m, 0.65H, R1), 3.33 (m, 0.35H, R2), 2.62–2.92 (m, 3.65H), 2.30–2.36 (m, 3.35H), 2.04–2.12 (m, 1H), 1.40–1.96 (m, 11H), 0.80–1.05 (m, 12H), –0.02–0.15 (m, 6H), LC-MS (M$^+$+1) (EI) 696.

Step B:

(4R)-3-[(2S,4R)-5-[((1S,2R,5R)-5-methyl-2-hydroxyl-1-cyclopentyl)amino]-2-hydroxy-1,5-dioxo-4-(phenylmethyl)pentyl]-5,5-dimethyl-N-[(2-methylphenyl)-methyl]-4-thiazolidinecarboxamide The titled compound was obtained following the procedure described in Example 1, Step H starting with the intermediate prepared in Step A (32 mg, 0.046 mmol). $^1$H NMR (CDCl$_3$, 500 MHz, mixture of rotamers R1 and R2 0.65/0.35): 7.16–7.38 (m, 9H), 7.02 (m, 0.35H, R2), 5.80 (m, 0.65H, R1), 5.36–5.42 (m, 1H, R1 and R2), 4.84–4.94 (m, 1.35H), 4.61–4.71 (m, 1.35H), 4.55 (d, J=9.5 Hz, 0.65H, R1), 4.43 (s, 0.65H, R1), 4.33 (dd, J=14.5, J=4 Hz, 0.65H, R1), 4.29 (dd, J=14.5, J=4 Hz, 0.35H, R2), 4.12 (d, J=10 Hz, 0.65H, R1), 3.96 (d, J=10 Hz, 0.35H, R2), 3.66 (m, 1H), 3.49 (m, 0.65H, R1), 3.20–3.26 (m, 1H), 2.68–3.03 (m, 5.35H), 2.32–2.36 (m, 3H), 1.30–2.32 (m, 11H), 0.80–1.04 (m, 4H), LC-MS (M$^+$+1) (EI) 582.

EXAMPLE 8

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-(2-phenylethyl)-4-thiazolidinecarboxamide

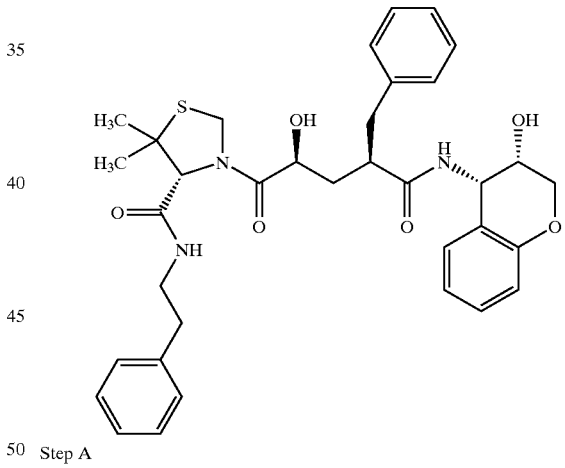

Step A

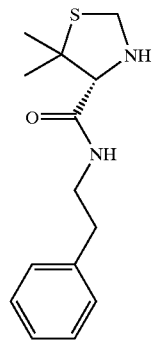

The titled compound was obtained following the procedure described in Example 2, Step A starting with phenethylamine (3.5 mL, 27.9 mmol) and L-5,5-dimethyl-thiazolidine-4-carboxylic acid (1.11 g, 6.8 mmol). $^1$H NMR (CDCl$_3$, 500 MHz): 7.20–7.35 (m, 5H), 6.56 (br s, 1H), 4.22 (d, J=9.5 Hz, 1H), 4.16 (d, J=9.5 Hz, 1H), 3.57 (q, J=6.5 Hz, 2H), 3.39 (s, 1H), 2.85 (t, J=6.5 Hz, 2H), 1.64 (s, 3H), 1.28 (s, 3H), LC-MS (M$^+$+1) (EI) 265.

Step B

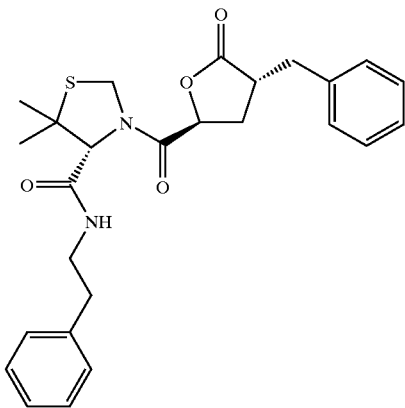

The titled compound was obtained following the procedure described in Example 5, Step B starting with the intermediate prepared in Step A (145 mg, 0.55 mmol) and this example and the intermediate prepared as in Example 1, Step A (180 mg, 0.82 mmol). $^1$H NMR (CDCl$_3$, 500 MHz, mixture of rotamers 1:1 ratio): 7.16–7.34 (m, 10H), 6.08 (br t, 0.5H), 5.67 (br t, 0.5H), 4.78–4.86 (m, 1.5H), 4.52–4.64 (m, 1.5H), 4.20 (s, 0.5H), 3.96 (s, 0.5H), 3.46–3.59 (m, 2H), 3.10–3.26 (m, 1.5H), 2.72–2.86 (m, 3H), 2.58 (m, 0.5H), 2.22 (m, 1H), 2.08 (m, 0.5H), 1.45 (m, 3H), 1.28–1.36 (m, 3H), LC-MS (M$^+$+1) (EI) 467.

Step C

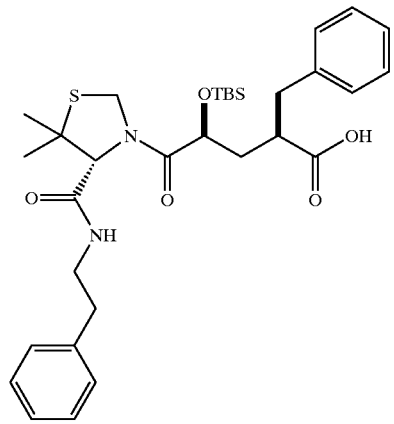

The titled compound was obtained following the procedure described in Example 1, Step F starting with the intermediate prepared in Step B (80 mg, 0.171 mmol) of this example. The crude product was used in Step D without further purification. LC-MS (M$^+$+1) (EI) 599.

Step D

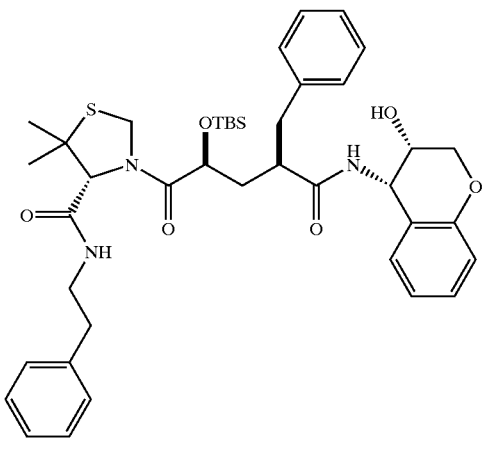

The titled compound was obtained following the procedure described in Example 3, Step A starting with intermediate prepared in Step C (100 mg, 0.167 mmol) of this example and cis-aminochromanol (31 mg, 0.19 mmol). $^1$H NMR (CDCl$_3$, 500 MHz, mixture of rotamers 1:1 ratio): 7.08–7.36 (m, 13H), 6.87 (m, 0.5H), 6.76–6.82 (m, 0.5H), 6.46 (br t, J=5.5 Hz, 0.5H), 5.78 (d, J=8 Hz, 0.5H), 5.70 (m, 1H), 5.23 (dd, J=8, J=4 Hz, 0.5H), 5.12 (dd, J=8, J=4 Hz, 0.5H), 4.80 (d, J=9 Hz, 0.5H), 4.68–4.72 (m, 1.5H), 4.54 (s, 0.5H), 4.38 (t, J=6.5 Hz, 0.5H), 4.29 (dd, J=9.5, J=2 Hz, 0.5H), 4.24 (s, 0.5H), 4.06 (m, 1H), 3.98–4.02 (m, 0.5H), 3.90–3.93 (m, 0.5H), 3.84 (m, 1H), 3.50 (m, 1H), 3.36–3.44 (m, 1H), 2.72–2.96 (m, 5H), 2.45 (m, 1H), 2.29 (m, 0.5H), 2.12 (m, 0.5H), 1.78–1.90 (m, 1H), 1.50 (s, 1.5H), 1.46 (s, 1.5H), 1.37 (s, 1.5H), 1.33 (s, 1.5H), 0.88 (s, 9H), 0.06 (m, 3H), 0.02 (s, 1.5H), −0.03 (s, 1.5H), LC-MS (M$^+$+1) (EI) 746.

Step E:

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(2-phenylethyl)-4-thiazolidinecarboxamide The titled compound was obtained following the procedure described in Example 1, Step H starting with the intermediate prepared in Step D (96 mg, 0.13 mmol) of this example. $^1$H NMR (CDCl$_3$, 500 MHz, mixture of rotamers 1:1 ratio): 7.10–7.38 (m, 12H), 7.04 (m, 0.5H), 6.98 (m, 0.5H), 6.88 (m, 0.5H), 6.76–6.82 (m, 0.5H), 6.48 (m, 0.5H), 5.80–5.84 (m, 1H), 5.62 (m, 0.5H), 5.16–5.18 (m, 1H), 4.83 (d, J=9.5 Hz, 0.5H), 4.79 (d, J=9.5 Hz, 0.5H), 4.72 (d, J=9.5 Hz, 0.5H), 4.59 (d, J=9.5 Hz, 0.5H), 4.50 (s, 0.5H), 4.26–4.32 (m, 1H), 3.96–4.08 (m, 2.5H), 3.66–3.78 (m, 1.5H), 3.60 (m, 0.5H), 3.42–3.49 (m, 1H), 3.34 (d, J=8 Hz, 0.5H), 3.14–3.22 (m, 0.5H), 2.78–3.02 (m, 4H), 2.66–2.72 (m, 1H), 2.10–2.20 (m, 2H), 1.48–1.66 (m, 4H), 1.38 (m, 3H), LC-MS (M$^+$+1) (EI) 632.

EXAMPLE 9

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(4-pyridinylmethyl)-4-thiazolidinecarboxamide

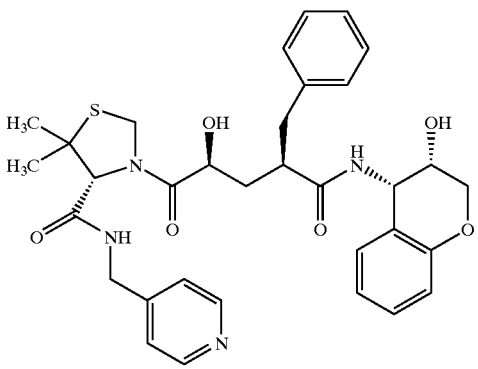

Step A

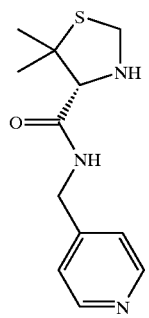

The titled compound was obtained following the procedure described in Example 2, Step A starting with 4-(aminomethyl)pyridine (1.29 mL, 12.7 mmol) and L-5,5-dimethyl-thiazolidine-4-carboxylic acid (510 mg, 3.2 mmol). $^1$H NMR (CDCl$_3$, 500 MHz): 8.53 (m, 2H), 7.42 (br s, 1H), 7.19 (dd, J=4.5, J=1.5 Hz, 2H), 4.45 (dd, J=6, J=1.5 Hz, 2H), 4.26 (d, J=9.5 Hz, 1H), 4.19 (d, J=9.5 Hz, 1H), 3.57 (s, 1H), 1.68 (s, 3H), 1.34 (s, 3H), LC-MS (M$^+$+1) (EI) 252.

Step B

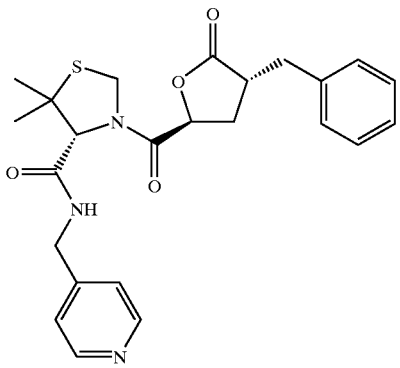

The titled compound was obtained following the procedure described in Example 5, Step B starting with the intermediate prepared in Step A (252 mg, 1.0 mmol) of this example and the intermediate prepared as in Example 1, Step A (331 mg, 1.5 mmol). $^1$H NMR (CDCl$_3$, 500 MHz, mixture of rotamers R1 and R2 0.6/0.4 ratio): 8.50–8.60 (m, 2H), 7.14–7.34 (m, 7H), 6.56 (br t, 0.4H, R2), 6.25 (br t, 0.6H, R1), 4.82–4.90 (m, 1.4H), 4.68 (d, J=9.5 Hz, 0.6H, R1), 4.60–4.67 (m, 1H), 4.37–4.53 (m, 2H), 4.34 (s, 0.6H, R1), 4.10 (s, 0.4H, R2), 3.08–3.26 (m, 2H), 2.84–2.92 (m, 1H), 2.77 (dd, J=9, J=4 Hz, 0.4H, R2), 2.58 (m, 0.6H, R1), 2.30 (m, 0.4H, R2), 2.22 (m, 0.4H, R2), 2.08–2.17 (m, 1.2H), 1.56 (s, 1.8H, R1), 1.50 (s, 1.2H, R2), 1.40–1.44 (m, 3H), LC-MS (M$^+$+1) (EI) 454.

Step C

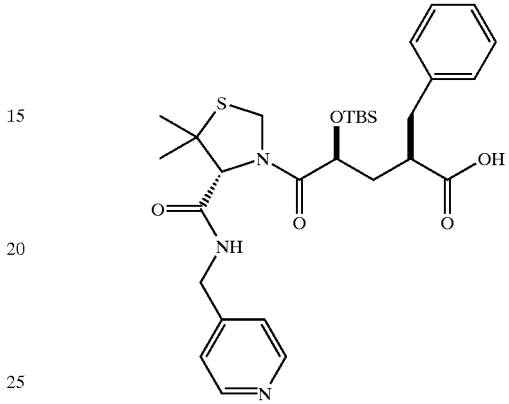

The titled compound was obtained following the procedure described in Example I, Step F starting with intermediate prepared in Step B (176 mg, 0.39 mmol) of this example. The crude product was used in Step D without further purification. LC-MS (M$^+$+1) (EI) 586.

Step D

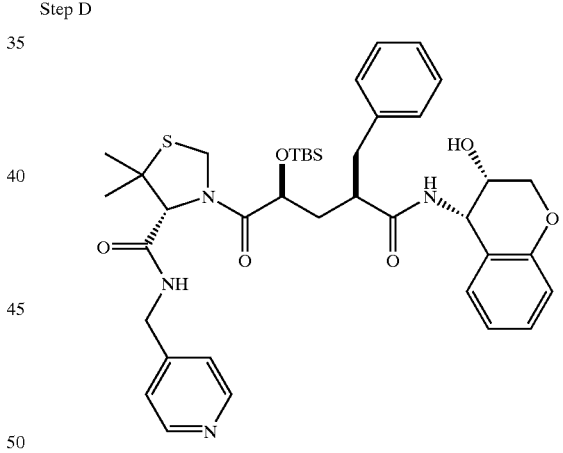

The titled compound 85% pure was obtained following the procedure described in Example 3, Step A starting with the intermediate prepared in Step C (112 mg, 0.19 mmol) of this example and cis-aminochromanol (35 mg, 0.21 mmol). $^1$H NMR (CDCl$_3$, 500 MHz, mixture of rotamers R1 and R2 0.6/0.4 ratio): 8.46–8.60 (m, 2H), 7.02–7.38 (m, 9H), 6.74–6.94 (m, 2H), 6.24–6.28 (m, 1H), 5.87 (d, J=8.5 Hz, 0.6H, R1), 5.73 (d, J=8.5 Hz, 0.4H, R2), 5.10 (dd, J=8, J=3.5 Hz, 0.6H, R1), 5.02 (dd, J=8, J=3.5 Hz, 0.4H, R2), 4.99 (d, J=9.5 Hz, 0.4H, R2), 4.64–4.84 (m, 2.6H), 4.28–4.48 (m, 3H), 4.14 (s, 0.6H, R1), 4.06–4.11 (m, 0.4H), 4.04 (s, 0.4H, R2), 3.92–3.98 (m, 0.6H, R1), 3.82 (m, 0.6H, R1), 3.76 (m, 0.4H, R2), 3.62–3.66 (m, 0.4H, R2), 3.50–3.55 (m, 0.6H, R1), 3.28 (m, 0.4H, R2), 2.68–3.04 (m, 2.6H), 2.44–2.50 (m, 0.6H, R1), 2.28 (m, 0.4H, R2), 1.94–1.98 (m, 0.6H, R1), 1.80–1.89 (m, 0.4H, R2), 1.58 (s, 1.8H, R1), 1.54 (s, 1.2H, R2), 1.45 (s, 1.8H, R1), 1.43 (s, 1.2H, R2), 0.84–0.88 (m, 9H), −0.04–0.09 (m, 6H), LC-MS (M⁺+1) (EI) 733.

Step E:

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(4-pyridinylmethyl)-4-thiazolidinecarboxamide The titled compound was obtained following the procedure described in Example 1, Step H starting with intermediate prepared in Step D (70 mg, 0.096 mmol) of this example. ¹H NMR (CDCl₃, 500 MHz, mixture of rotamers R1 and R2 0.75/0.25 ratio): 8.55 (d, J=5.5 Hz, 0.25H, R2), 8.42 (d, J=5.5 Hz, 0.75H, R1), 7.06–7.36 (m, 10.25H), 6.78–6.92 (m, 2.75H), 6.16 (br t, J=6 Hz, 0.25H, R2), 5.87 (br t, J=6 Hz, 0.75H, R1), 5.16 (dd, J=8, J=3.5 Hz, 0.25H, R2), 4.95 (d, J=9.5 Hz, 0.75H, R1), 4.88 (d, J=9.5 Hz, 0.75H, R1), 4.84 (d, J=9.5 Hz, 0.25H, R2), 4.78 (dd, J=8, J=3.5 Hz, 0.75H, R1), 4.73 (s, 0.75H, R1), 4.61–4.67 (m, 1H), 4.59 (dd, J=15.5, J=7 Hz, 0.25H, R2), 4.45 (s, 0.25H, R2), 4.28–4.36 (m, 1H), 3.94–4.06 (m, 2H), 3.89 (dd, J=15.5, J=3.5 Hz, 0.25H, R2), 3.78 (d, J=11.5 Hz, 0.75H, R1), 3.71 (m, 0.25H, R2), 3.46–3.52 (m, 1.75H), 2.89–3.05 (m, 2H), 2.74–2.82 (m, 1H), 2.08–2.24 (m, 1H), 1.46–1.72 (m, 4H), 1.38 (m, 0.25H), 1.23–1.27 (m, 3H), 0.98 (m, 0.75H, R1), LC-MS (M⁺+1) (EI) 619.

EXAMPLE 10

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl]-5,5-dimethyl-N-(3-pyridinylmethyl)-4-thiazolidinecarboxamide

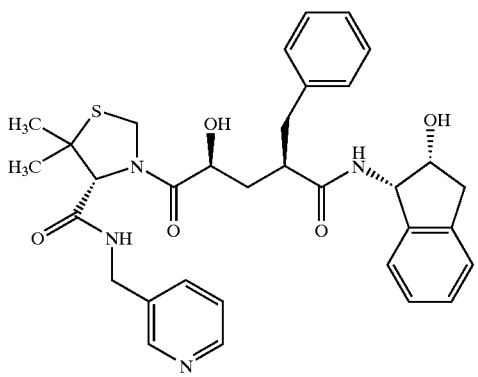

Step A

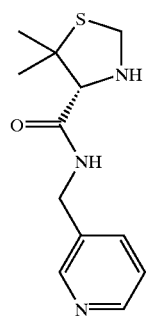

The titled compound was obtained following the procedure described in Example 2, Step A starting with 3-(aminomethyl)pyridine (1.30 mL, 12.8 mmol) and L-5,5-dimethyl-thiazolidine-4-carboxylic acid (520 mg, 3.2 mmol). ¹H NMR (CDCl₃, 500 MHz): 8.50–8.53 (m, 2H), 7.63 (m, 1H), 7.22–7.28 (m, 2H), 4.45 (d, J=6 Hz, 2H), 4.24 (d, J=9.5 Hz, 1H), 4.16 (d, J=9.5 Hz, 1H), 3.51 (s, 1H), 1.68 (s, 3H), 1.32 (s, 3H), LC-MS (M⁺+1) (EI) 252.

Step B

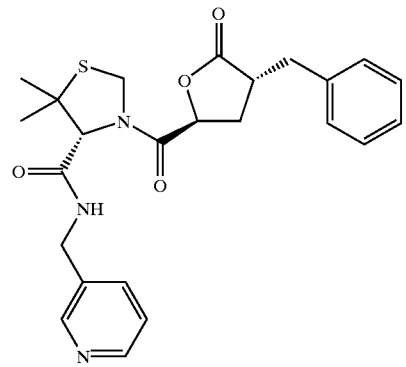

The titled compound was obtained following the procedure described in Example 5, Step B starting with the intermediate prepared in Step A (260 mg, 1.0 mmol) of this example and the intermediate prepared as in Example 1, Step A (340 mg, 1.5 mmol). ¹H NMR (CDCl₃, 500 MHz, mixture of rotamers R1 and R2 0.6/0.4 ratio): 8.46–8.56 (m, 2H), 7.63 (m, 1H), 7.17–7.34 (m, 6H), 6.72 (br t, J=7 Hz, 0.4H, R2), 6.42 (br t, J=7 Hz, 0.6H, R1), 4.89 (dd, J=8.5, J=2.5 Hz, 0.6H, R1), 4.80–4.86 (m, 1H), 4.78 (d, J=11 Hz, 0.4H, R2), 4.68 (d, J=9 Hz, 0.6H, R1), 4.56–4.62 (m, 0.8H), 4.36–4.48 (m, 1.6H), 4.33 (s, 0.6H), 4.08 (s, 0.4H), 3.06–3.24 (m, 2H), 2.85 (dd, J=13.5, J=8 Hz, 0.6H, R1), 2.75 (dd, J=13.5, J=8 Hz, 0.4H, R2), 2.58 (m, 0.6H, R1), 2.04–2.28 (m, 1.4H), 1.53 (s, 1.8H, R1), 1.48 (s, 1.2H, R2), 1.40 (s, 1.2H, R2), 1.38 (s, 1.8H, R1), LC-MS (M⁺+1) (EI) 454.

Step C

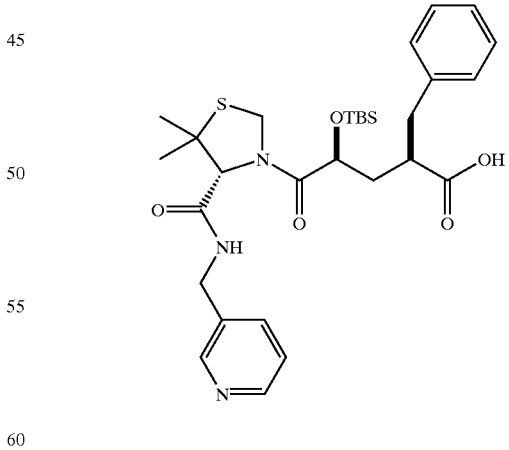

The titled compound was obtained following the procedure described in Example 1, Step F starting with intermediate prepared in Step B (191 mg, 0.42 mmol) of this example. The crude product was used in Step D without further purification. LC-MS (M⁺+1) (EI) 586.

Step D

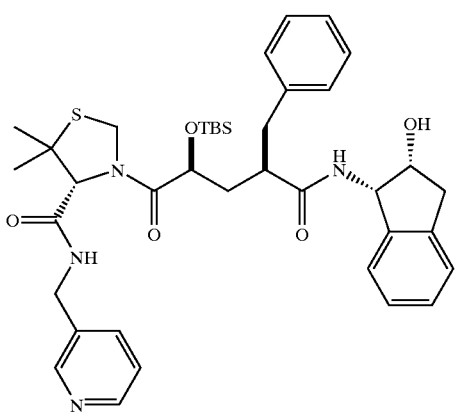

The titled compound was obtained following the procedure described in Example 3, Step A starting with the intermediate prepared in Step C (247 mg, 0.42 mmol) of this example and cis-aminoindanol (39 mg, 0.26 mmol). $^1$H NMR (CDCl$_3$, 500 MHz, mixture of rotamers R1 and R2 0.6/0.4 ratio): 8.28–8.54 (m, 2H), 7.58 (d, J=8 Hz, 0.6H, R1), 7.44 (d, J=8 Hz, 0.4H, R2), 7.06–7.27 (m, 10.4H), 6.49 (m, 0.6H, R1), 6.28 (m, 0.6H, R1), 5.83 (m, 0.4H, R2), 5.22 (dd, J=8, J=4.5 Hz, 0.6H, R1), 5.09 (dd, J=8, J=4.5 Hz, 0.4H, R2), 4.73–4.85 (m, 2.6H), 4.53 (dd, J=10, J=6.5 Hz, 0.4H, R2), 4.24–4.46 (m, 3H), 4.18–4.21 (m, 1H), 2.64–3.06 (m, 6H), 2.31 (m, 0.6H), 2.10 (m, 0.6H, R1), 1.78–1.88 (m, 0.8H), 1.50–1.55 (m, 3H), 1.38–1.42 (m, 3H), 0.90 (s, 3.6H, R2), 0.84 (s, 5.4H, R1), −0.06–1.01 (m, 6H), LC-MS (M$^+$+1), (EI) 717.

Step E:

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl]-5,5-dimethyl-N-(3-pyridinylmethyl)-4-thiazolidinecarboxamide The titled compound was obtained following the procedure described in Example 1, Step H starting with intermediate prepared in Step D (95 mg, 0.13 mmol) of this example. $^1$H NMR (CDCl$_3$, 500 MHz, mixture of rotamers R1 and R$_2$ $_{0.6/0.4}$ ratio): 8.54 (d, J=1.5 Hz, 0.4H, R2), 8.45 (dd, J=5, J=1.5 Hz, 0.4H, R2), 8.37 (dd, J=5, J=1.5 Hz, 0.6H, R1), 8.06 (d, J=1.5 Hz, 0.6H, R1), 7.63 (d, J=8 Hz, 0.4H, R2), 7.12–7.38 (m, 10H), 7.10 (dd, J=8, J=5, 0.6H, R1), 6.95 (d, J=7.5 Hz, 0.6H, R1), 6.19 (br t, J=4.5 Hz, 0.4H, R2), 5.92–6.00 (m, 1H, R1 and R2), 5.26 (dd, J=8.5, J=4.5 Hz, 0.4H, R2), 4.87–4.97 (m, 2H), 4.82 (d, J=9.5 Hz, 0.4H, R2), 4.76 (s, 0.6H, R1), 4.56–4.67 (m, 1.6H), 4.43 (s, 0.4H, R2), 4.28–4.38 (m, 0.8H), 4.21 (m, 0.4H, R2), 3.98–4.02 (m, 1.2H), 3.80 (dd, J=15, J=3.5 Hz, 0.6H, R1), 3.54 (m, 0.6H, R1), 2.98–3.05 (m, 1.4H), 2.85–2.97 (m, 2H), 2.72–2.83 (m, 2.6H), 2.08–2.23 (m, 1H), 1.54–1.73 (m, 4H), 1.42–1.48 (m, 3H), LC-MS (M$^+$+1) (EI) 603.

EXAMPLE 11

(2S)-1[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-N-[(2-methylphenyl)methyl]-2-pyrrolidinecarboxamide

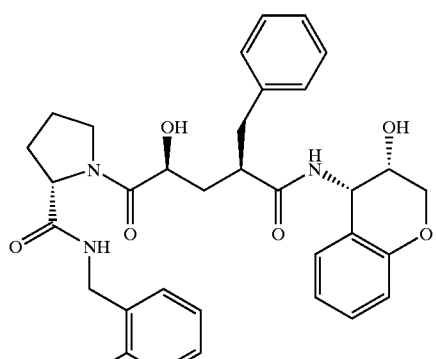

Step A

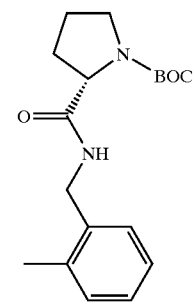

The titled compound was obtained following the procedure described in Example 2, Step A starting with 2-methylbenzylamine (1.73 mL, 13.9 mmol) and N-(tert-butoxycarbonyl)-L-proline (2.50 g, 11.6 mmol). $^1$H NMR (CDCl$_3$, 500 MHz): 7.10–7.26 (m, 4H), 6.25 (m, 1H), 4.22–4.56 (m, 3H), 3.30–3.47 (m, 2H), 2.41 (m, 1H), 2.31 (s, 3H), 2.25 (m, 1H), 1.81–2.20 (m, 2H), 1.40 (s, 9H).

Step B

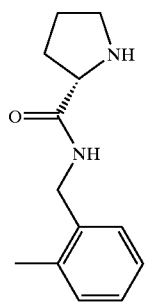

The titled compound was obtained following the procedure described in Example 1, Step D starting with the intermediate prepared in Step A (2.70 g, 8.5 mmol) of this example. The product was used in Step C without further purification. ¹H NMR (CDCl₃, 500 MHz): 8.09 (br t, 1H), 7.12–7.21 (m, 3H), 4.39 (d, J=7 Hz, 2H), 4.03 (dd, J=9, J=7 Hz, 1H), 3.95 (m, 2H), 3.08 (m, 1H), 2.99 (m, 1H), 2.29 (s, 3H), 2.22 (m, 1H), 1.95 (m, 1H), 1.77 (m, 2H), LC-MS (M⁺+1) (EI) 219.

Step C

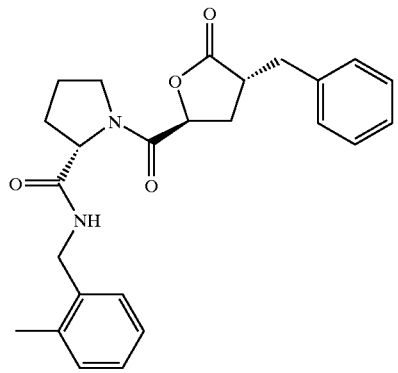

The titled compound was obtained following the procedure described in Example 5, Step B starting with the intermediate prepared in Step B (268 mg, 1.2 mmol) of this example and the intermediate prepared as in Example 1, Step A (278 mg, 1.3 mmol). ¹H NMR (CDCl₃, 500 MHz, mixture of rotamers R1 and R2 0.8/0.2 ratio): 7.40–7.48 (m, 0.4H), 7.08–7.34 (m, 8.6H), 6.72 (m, 0.8H, R1), 5.98 (m, 0.2H, R2), 4.87 (dd, J=8.5, J=2 Hz, 0.8H, R1), 4.73 (dd, J=8, J=2.5 Hz, 0.2H, R2), 4.65 (dd, J=8.5, J=2 Hz, 0.2H, R2), 4.48 (dd, J=8, J=2.5 Hz, 0.8H, R1), 4.34–4.42 (m, 1.6H), 3.48–3.64 (m, 2.4H), 3.22 (dd, J=14, J=4.5 Hz, 0.2H, R2), 3.15 (dd, J=14, J=4.5 Hz, 0.8H, R1), 3.04–3.11 (m, 1H), 2.84 (dd, J=8, J=14 Hz, 0.8H, R1), 2.76 (dd, J=8, J=14 Hz, 0.2H, R2), 2.25–2.46 (m, 4.2H), 1.89–2.22 (m, 4.8H), LC-MS (M⁺+1) (EI) 421.

Step D

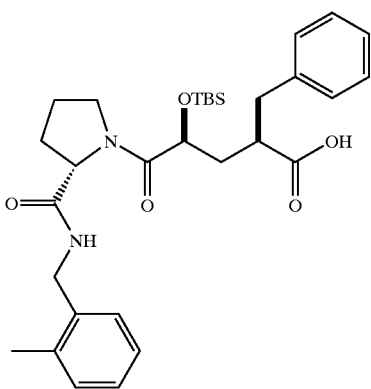

The titled compound was obtained following the procedure described in Example 1, Step F starting with intermediate prepared in Step C (110 mg, 0.26 mmol) of this example. The crude product was used in Step E without further purification. LC-MS (M⁺+1) (EI) 553.

Step E

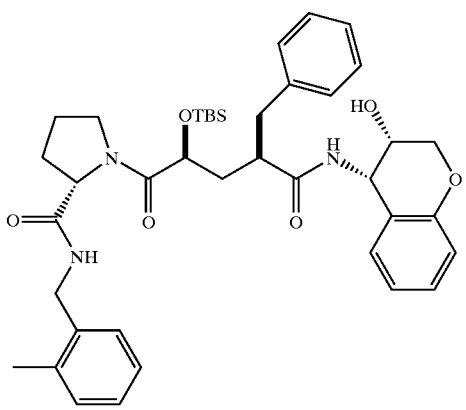

The titled compound was obtained following the procedure described in Example 3, Step A starting with intermediate prepared in Step D (72 mg, 0.13 mmol) of this example and cis-aminochromanol (23 mg, 0.14 mmol). ¹H NMR (CDCl₃, 500 MHz, mixture of rotamers R1 and R2 0.8/0.2): 7.00–7.38 (m, 13.2H), 6.91 (m, 0.8H, R1), 6.76–6.84 (m, 1H), 5.92 (d, J=8 Hz, 0.8H, R1), 5.62 (d, J=8 Hz, 0.2H, R2), 5.12 (dd, J=8, J=4 Hz, 0.8H, R1), 4.95 (m, 0.2H, R2), 4.52–4.59 (m, 1H), 4.26–4.47 (m, 2.8H), 3.97–4.16 (m, 1H), 3.76–3.88 (m, 0.4H), 3.45–3.64 (m, 2.8H), 2.64–3.06 (m, 4H), 1.80–2.45 (m, 8.6H), 1.70 (m, 0.4H, R2), 0.72–0.86 (m, 9H), −0.04–0.08 (m, 6H), LC-MS (M⁺+1) (EI) 700.

Step F:

(2S)-1-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-N-[(2-methylphenyl)methyl]-2-pyrrolidinecarboxamide The titled compound was obtained following the procedure described in Example 1, Step H starting with the intermediate prepared in Step E (40 mg, 0.057 mmol) of this example. ¹H NMR (CDCl₃, 500 MHz, mixture of rotamers R1 and R2 0.8/0.2 ratio): 7.06–7.35 (m, 11H), 7.01 (m, 0.4H), 6.94 (m, 0.2H, R2), 6.86 (m, 0.8H, R1), 6.79 (m, 0.8H, R1), 6.72 (m, 0.8H, R1), 5.78 (d, J=8 Hz, 0.8H, R1), 5.73 (d, J=8 Hz, 0.2H, R2), 5.16 (dd, J=8, J=4.5 Hz, 0.8 H, R1), 4.56–4.72 (m, 1.4H), 4.36–4.46 (m, 1.2H), 4.22 (m, 1H), 3.92–4.04 (m, 1.6H), 3.82–3.87 (m, 0.6H), 3.42–3.76 (m, 3.4H), 3.18–3.23 (m, 1H), 2.76–2.99 (m, 3H), 2.38–2.44 (m, 0.8H, R1), 2.10–2.32 (m, 2H), 1.93–2.02 (m, 1.8H), 1.74–1.77 (m, 0.4H), 1.36–1.68 (m, 3H), 0.96–1.04 (m, 2H), LC-MS (M⁺+1) (EI) 587.

EXAMPLE 12

(2S)-1-[(2S,4R)-5-[((1S,2R)-2,3-dihydro-2-hydroxy-1H-inden-1-yl)amino]-2-hydroxy-1,5-dioxo-4-(phenylmethyl)pentyl]-N-[(2-methylphenyl)methyl]-2-pyrrolidine-carboxamide

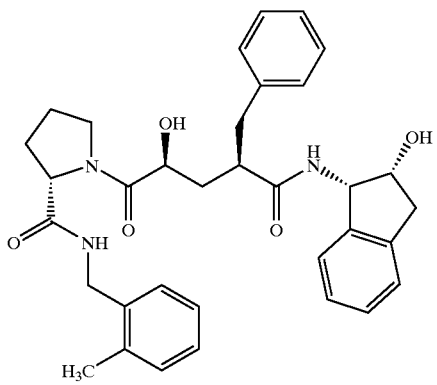

Step A

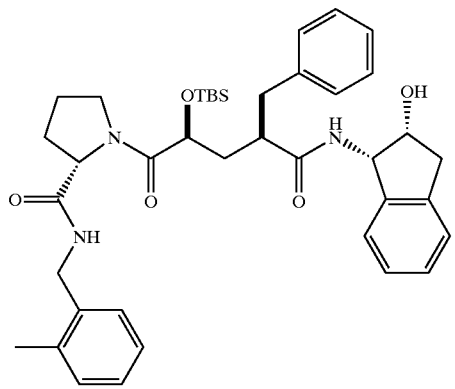

The titled compound was obtained following the procedure described in Example 3, Step A starting with the intermediate prepared in Example 11, Step D (72 mg, 0.13 mmol) and cis-aminoindanol (24 mg, 0.16 mmol). $^1$H NMR (CDCl$_3$, 500 MHz, mixture of rotamers R1 and R2 0.8/0.2 ratio): 7.00–7.39 (m, 13H), 6.82–6.92 (m, 1H), 6.24 (m, 0.2H, R2), 5.84 (d, J=8 Hz, 0.8H, R1), 5.62 (d, J=8 Hz, 0.2H, R2), 5.18 (dd, J=5, J=8 Hz, 0.8H, R1), 4.94 (dd, J=5, J=8 Hz, 0.2H, R2), 4.84–4.89 (m, 0.4H), 4.52–4.66 (m, 1.8H), 4.32–4.48 (m, 2.8H), 4.21–4.27 (m, 0.8H, R1), 4.08–4.14 (m, 0.2H, R2), 3.99 (m, 0.2H, R2), 3.65–3.74 (m, 0.8H, R1), 3.44–3.61 (m, 1.8H), 2.63–3.05 (m, 5H), 2.24–2.45 (m, 4H), 2.05–2.21 (m, 1H), 1.78–2.02 (m, 3H), 0.71–0.94 (m, 9H), −0.20–0.15 (m, 6H), LC-MS (M$^+$+1) (EI) 684.

Step B:

(2S)-1-[(2S,4R)-5-[((1S,2R)-2,3-dihydro-2-hydroxy-1H-inden-1-yl)amino]-2-hydroxy-1,5-dioxo-4-(phenylmethyl)pentyl]-N-[(2-methylphenyl)methyl]-2-pyrrolidine-carboxamide The titled compound was obtained following the procedure described in Example 1, Step H starting with the intermediate prepared in Step E (40 mg, 0.057 mmol) of this example. $^1$H NMR (CDCl$_3$, 500 MHz, mixture of rotamers R1 and R2 0.7/0.3 ratio): 7.10–7.38 (m, 12.7H), 7.01–7.06 (m, 0.3H, R2), 6.90–6.97 (m, 1H), 6.73–6.79 (m, 1.7H), 5.80 (d, J=8.5 Hz, 1H), 5.28 (dd, J=8.5, J=5 Hz, 0.7H, R1), 4.89 (dd, J=8.5, J=5 Hz, 0.3H, R2), 4.69 (m, 0.3H, R2), 4.56–4.63 (m, 1H), 4.37–4.48 (m, 1.4H), 4.18–4.26 (m, 1.4H), 3.94–4.03 (m, 0.6H), 3.82–3.87 (m, 0.3H, R2), 3.58–3.76 (m, 1.4H), 3.43–3.52 (m, 1.3H), 2.96–3.04 (m, 1H), 2.72–2.93 (m, 3.6H), 2.38–2.45 (m, 0.7H, R1), 2.10–2.34 (m, 4H), 1.90–2.03 (m, 2.3H), 1.45–1.68 (m, 1H), 0.74 (d, J=3.5 Hz, 0.7H, R1), 0.69 (d, J=3.5 Hz, 0.3H, R2), LC-MS (M$^+$+1) (EI) 570.

EXAMPLE 13

(2S,4S)-1-[(2S,4R)-5-[((1S,2R)-2,3-dihydro-2-hydroxy-1H-inden-1-yl)amino]-2-hydroxy-1,5-dioxo-4-4-(phenylmethyl)pentyl]-N-[(2-methylphenyl)methyl]-4-chloro-2-pyrrolidinecarboxamide

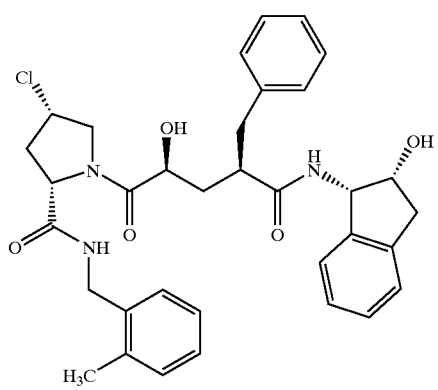

Step A

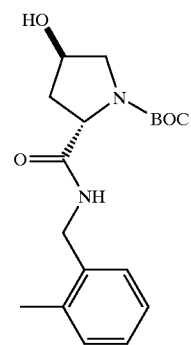

The titled compound was obtained following the procedure described in Example 2, Step A starting with 2-methylbenzylamine (0.73 mL, 6.08 mmol) and N-(tert-butoxycarbonyl)-4(R)-hydroxy-L-proline (1.28 g, 5.53 mmol). $^1$H NMR (CDCl$_3$, 500 MHz): 7.10–7.26 (m, 4H), 4.16–4.56 (m, 4H), 3.44–3.53 (m, 2H), 2.32 (s, 3H), 1.80 (br s, 1H), 1.58 (br s, 1H), 1.40 (s, 9H).

Step B

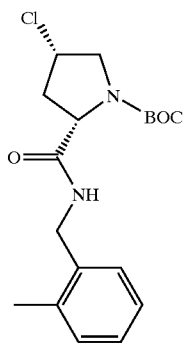

A solution of intermediate prepared in Step A (1.80 g, 5.4 mmol) and triphenylphosphine (2.3 g, 8.8 mmol) was refluxed in carbontetrachloride (70 mL) for 10 hours. The insoluble material was removed by filtration and was washed with ethyl ether (50 mL). The filtrate was concentrated in vacuo and the crude reaction mixture purified by flash column chromatography on silica gel with 1:1 ethyl acetate/hexane as the eluant to give the titled compound as a white solid. $^1$H NMR (CDCl$_3$, 500 MHz): 7.24–7.28 (m, 1H), 7.14–7.20 (m, 3H), 4.30–4.62 (m, 4H), 3.88 (dd, J=12, J=5 Hz, 1H), 3.63 (br s, 1H), 2.60–2.74 (m, 2H), 2.33 (s, 3H), 1.38 (s, 9H).

Step C

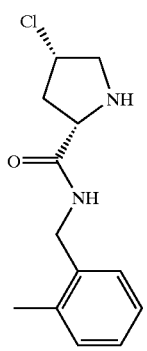

The titled compound was obtained following the procedure described in Example 1, Step D starting with the intermediate prepared in Step B (1.15 g, 3.3 mmol) of this example. The product was used in Step D without further purification. $^1$H NMR (CDCl$_3$, 500 MHz): 7.75 (br s, 1H), 7.15–7.28 (m, 4H), 4.40–4.50 (m, 2H), 4.31 (m, 1H), 3.88 (dd, J=10, J=5 Hz, 1H), 3.41 (dd, J=10, J=5 Hz, 1H), 3.09 (dd, J=11.5, J=4 Hz, 1H), 2.67–2.76 (m, 1H), 2.30–2.37 (m, 4H), LC-MS (M$^+$+1) (EI) 253.

Step D

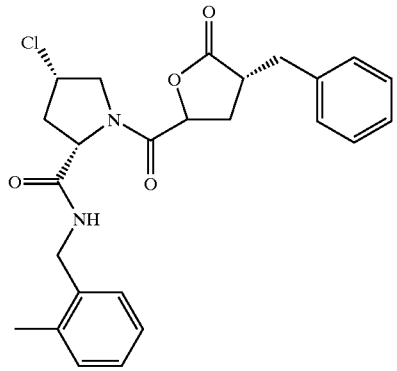

The titled compound was obtained following the procedure described in Example 5, Step B starting with the intermediate prepared in step C (345 mg, 1.4 mmol) of this example and the intermediate prepared as in Example 1, Step A (380 mg, 1.7 mmol). $^1$H NMR (CDCl$_3$, 500 MHz, mixture of rotamers R1 and R2 0.8/0.2 ratio): 7.10–7.33 (m, 9H), 6.42 (br t, 0.8 H, R1), 6.25 (br t, 0.2H, R2), 4.80 (dd, J=8.5, J=3 Hz, 0.8H, R1), 4.76 (dd, J=8.5, J=3 Hz, 0.2H, R2), 4.34–4.51 (m, 4H), 4.17 (dd, J=11, J=7 Hz, 0.8H, R1), 4.00 (dd, J=11, J=7 Hz, 0.2H, R2), 3.84 (m, 0.2H, R2), 3.62 (dd, J=11, J=6 Hz, 0.8H, R1), 3.04–3.24 (m, 2H), 2.85 (dd, J=14, J=9 Hz, 0.8H, R1), 2.58–2.78 (m, 2.4H), 2.53 (m, 0.8H, R1), 2.33 (s, 0.6H, R2), 2.28 (s, 2.4H, R1), 2.04–2.22 (m, 1H), LC-MS (M$^+$+1) (EI) 455.

Step E

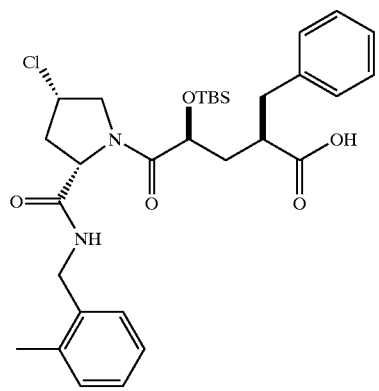

The titled compound was obtained following the procedure described in Example 1, Step F starting with intermediate prepared in Step D (307 mg, 0.68 mmol) of this example. The crude product was used in Step F without further purification. LC-MS (M$^+$+1) (EI) 587.

Step F

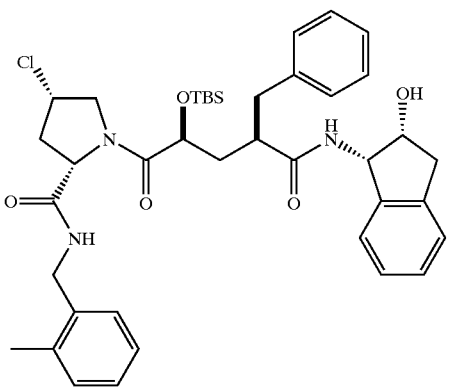

The titled compound was obtained following the procedure described in Example 3, Step A starting with the intermediate prepared in Step E (130 mg, 0.22 mmol) and cis-aminoindanol (40 mg, 0.27 mmol). $^1$H NMR (CDCl$_3$, 500 MHz, mixture of rotamers R1 and R2 0.9/0.2 ratio): 6.97–7.46 (m, 13.1H), 6.67 (br t, 0.9H, R1), 5.53–5.60 (m, 1H), 5.12 (dd, J=8.5, J=4.5 Hz, 0.9H, R1), 5.60 (m, 0.1H, R2), 4.70 (m, 0.1H, R2), 4.24–4.49 (m, 5.9H), 4.10–4.19 (m, 1.1H), 3.84 (dd, J=12, J=6 Hz, 0.9H, R1), 2.96 (dd, J=16, J=5, Hz, 0.9H, R1), 2.62–2.88 (m, 5.1H), 2.16–2.56 (m, 5H), 1.74–1.80 (m, 1H), 1.40–1.54 (m, 1H), 0.76–0.99 (m, 9H), −0.06–0.12 (m, 6H), LC-MS (M$^+$+1) (EI) 718.

Step G:

(2S,4R)-1-[(2S,4R)-5-[((1S,2R)-2,3-dihydro-2-hydroxy-1H-inden-1-yl)amino]-2-hydroxy-1,5-dioxo-4-(phenylmethyl)pentyl]-N-[(2-methylphenyl)methyl]-4-chloro-2-pyrrolidinecarboxamide The titled compound was obtained following the procedure described in Example 1, Step H starting with the intermediate prepared in Step E (40 mg, 0.057 mmol) of this example. $^1$H NMR (CDCl$_3$, 500 MHz, mixture of rotamers R1 and R2 0.7/0.3 ratio): 6.94–7.36 (m, 13H), 6.81 (br d, J=7 Hz, 0.3H, R3), 6.49 (br t, J=5 Hz, 0.7H, R1), 5.88 (d, J=9.5 Hz, 0.3H, R2), 5.83 (d, J=9.5 Hz, 0.7H R1), 5.27 (dd, J=8, J=5 Hz, 0.7H, R1), 5.01 (dd, J=8, J=5 Hz, 0.3H, R2), 4.53 (m, 0.3H, R2), 4.56–4.64 (m, 1H), 4.26–4.50 (m, 2.7H), 4.17–4.24 (m, 1.7H), 4.03 (m, 0.3H, R2), 3.96 (dd, J=11.5, J=6 Hz, 0.7H, R1), 3.74–3.88 (m, 1.3H), 3.46–3.54 (m, 1H), 2.70–3.04 (m, 6.3H), 2.50–2.63 (m, 1.7H), 2.31 (s, 2.1H, R1), 2.18 (m, 0.7H, R1), 2.07 (m, 0.3H, R2), 1.99 (s, 0.9H, R2), 1.45–1.54 (m, 1H), LC-MS (M$^+$+1) (EI) 604.

EXAMPLE 14

(αS,γR)-γ-[[((3S,4S)-3,4-dihydro-3-hydroxy-2H-1-benzopyran-4-yl)amino]carbonyl]-α-hydroxy-N-[1,1-dimethyl-2-[[(2-methylphenyl)methyl]amino]-2-oxoethyl]-benzenepentanamide

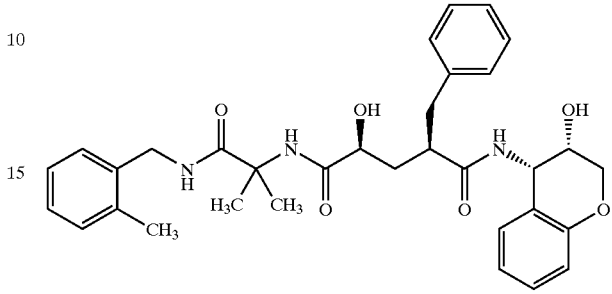

Step A

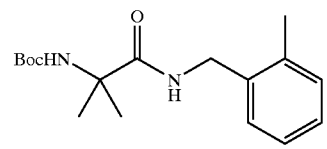

To a solution of Boc AIB acid (2.0 g, 9.84 mmol) in 10 mL of dichloromethane was added 2-methyl benzyl amide (1.46 mL, 11.81 mmol), dimethyl amino pyridine (120 mg, 0.98 mmol) and diisopropyl ethyl amine (1.88 mL, 10.82 mmol). 1-[3-(dimethylamino)propyl]-3-ethylcarbodiimide hydrochloride (2.07 g, 10.82 mmol) was added and the reaction stirred at room temperature under nitrogen for 18 hours. The reaction mixture was diluted with dichloromethane (100 mL) and washed successively with 10% citric acid, saturated sodium bicarbonate and saturated sodium chloride solution. The organic layer was dried over anhydrous sodium sulfate, filtered and concentrated in vacuo. The crude material was purified by flash chromatography with 40% ethyl acetate-hexanes to give the title compound as a white solid. $^1$H NMR (CDCl$_3$, 400 MHz), 7.2 (m, 4H), 6.6 (bs, 1H), 4.87 (bs, 1H), 4.45 (d, 2H), 2.34 (s, 3H), 1.43 (s, 3H), 1.41 (s, 3H), LC-MS (EI) (M$^+$+1−100) 207.2

Step B

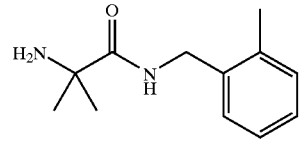

The intermediate prepared in Step A (1.6 g, 5.29 mmol) was dissolved in 10 mL of 30% trifluoroacetic acid/dichloromethane (v/v). The reaction mixture was stirred at room temperature and the progress of the reaction monitored by TLC. After 4 h the reaction mixture was diluted with 100 mL of dichloromethane and was washed with saturated sodium bicarbon solution, and brine and dried over anhydrous sodium sulfate. The solution was filtered and concentrated in vacuo to give a white solid. The product was used in step C without further purification. $^1$H NMR (CDCl$_3$, 400 MHz): 7.8 (bs, 1H), 7.18–7.23 (m, 4H), 4.43 (d, 2H), 2.34 (s, 3H), 1.41 (s, 6H), LCMS (M$^+$+1) (EI) 207.2

Step C

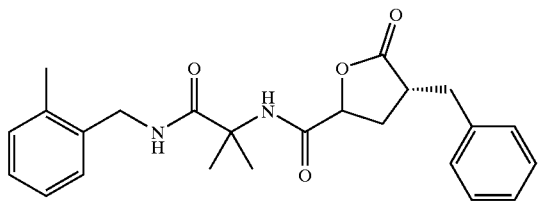

To a solution of the intermediate prepared in Step B (156 mg, 0.75 mmol), intermediate prepared in Example 1 Step A (200 mg, 0.9 mmol), and 1-hydroxy-7-azabenzotriazole (217 mg, 1.13 mmol) in 1 mL of dichloromethane was added 1-[3-(dimethylamino)propyl]-3-ethylcarbodiimide hydrochloride. The mixture was stirred at room temperature for 20 hours. The reaction mixture was diluted with dichloromethane (20 mL) and washed successively with 10% citric acid solution, saturated sodium bicarbonate and brine. The organic layer was dried over anhydrous sodium sulfate filtered and concentrated in vacuo. The crude material was purified by flash chromatography with 40% ethyl acetate-hexanes to give the desired product as a colorless oil. $^1$H NMR (CDCl$_3$): 7.26–7.35 (m, 3H), 7.18–7.21 (m, 6H), 6.85 (s, 1H), 6.33 (bs, 1H), 4.52 (dd, J=1.98, 4.9 Hz, 1H), 4.44 (dd, J=2.4, 5.3 Hz, 2H), 3.15 (dd, J=3.1, 9.0 Hz, 1H), 2.9 (m, 2H), 2.45 (m, 1H), 2.31 (m, 1H), 2.3 (s, 3H), 1.59 (s, 3H), 1.57 (s, 3H), LCMS (M$^+$+1) (EI) 409.4.

Step D

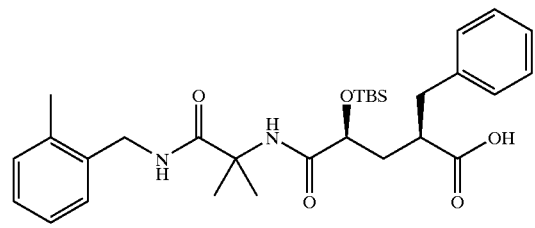

To a solution of the intermediate prepared in Step C (122 mg, 0.29 mmol) in 2 mL of p-dioxane was added a solution of lithium hydroxide monohydrate (14 mg, 0.33 mmol) in 2 mL of distilled water. The mixture was stirred at room temperature and the progress of the reaction was monitored by TLC. After 1.5 hours the reaction mixture was concentrated in vacuo. The product was azeotroped with toluene (3×10 mL) and dried under high vacuum. A white solid was obtained. N,N-dimethylformamide (4 mL) was added followed by imidazole (304 mg, 4.47 mmol) and tert-butyldimethylsilyl chloride (360 mg, 2.38 mmol). The resulting solution was stirred at room temperature for 24 hours. The reaction mixture was poured into pH=7 buffer solution and the product extracted with ethyl acetate (4×25 mL). The organic layers were combined and dried over anhydrous sodium sulfate and concentrated in vacuo to give the title compound as an oil. The crude product was used in the next step without further purification. LC-MS (M$^+$+1) (EI) 541.6

Step E

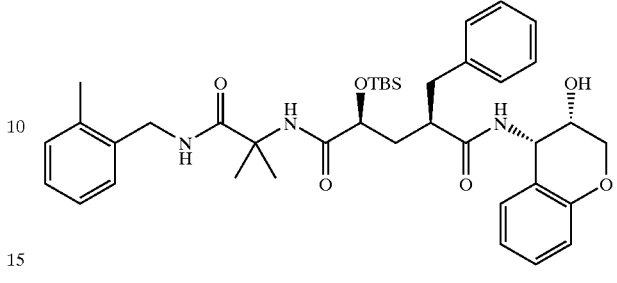

To a solution of the intermediate prepared in Step D (177 mg, 0.29 mmol), cis-aminochromanol (59 mg, 0.35 mmol) and 1-hydroxybenzotriazole (61 mg, 0.44 mmol) in 2 mL of dichloromethane was added 1-[3-(dimethylamino)propyl]-3-ethylcarbodiimide hydrochloride (85 mg, 0.44 mmol). The reaction was stirred at room temperature for 20 hours. The reaction was diluted with dichloromethane (20 mL) and washed successively with 10% citric acid, saturated sodium bicarbonate solution and brine. The organic layer was dried over anhydrous sodium sulfate filtered and concentrated in vacuo. The crude material was purified with 40% ethyl acetate-hexanes to give the title compound as a 1:1 mixture of rotamers. $^1$H NMR (CDCl$_3$): 8.47 (s, 1H), 7.62 (s, 1H), 7.35 (d, 1H), 7.1–7.28 (m, 22H), 6.93 (s, 2H), 6.76 (m, 2H), 6.27 (m, 2H), 5.15 (m, 1H), 4.58 (d, 2H), 4.51 (m, 2H), 4.22 (m, 1H), 3.86–3.94 (m, 2H), 3.7 (m, 1H), 3.5 (m, 1H), 2.94 (m, 2H), 2.78 (m, 4H), 2.5 (m, 1H), 2.39 (s, 3H), 2.33 (s, 3H), 2.25 (m, 3H), 2.1 (m, 1H), 1.84 (d, 1H), 1.68 (s, 3H), 1.63 (s, 3H), 1.57 (s, 3H), 0.97 (s, 9H), 0.75 (s, 9H), 0.24 (s, 6H), −0.002 (s, 3H), −0.02 (s, 3H). LC-MS(EI) (M$^+$+1) 574.6

Step F:

(αS,γR)-γ-[[((3S,4S)-3,4-dihydro-3-hydroxy-2H-1-benzopyran-4-yl)amino]carbonyl]-α-hydroxy-N-[1,1-dimethyl-2-[[(2-methylphenyl)methyl]amino]-2-oxoethyl]-benzenepentanamide To a solution of intermediate obtained in Step E (93 mg, 0.13 mmol) in 2 mL of anhydrous tetrahydrofuran was added tetrabutylammonium fluoride (149 μL, 0.14 mmol 1.0 M in tetrahydrofuran). The reaction mixture was stirred at room temperature and the progress of the reaction monitored by TLC. After 30 minutes the starting material was consumed and the reaction mixture was concentrated in vacuo. The crude material was purified by flash chromatography with 80% ethyl acetate-hexanes to give the title compound as a white solid. $^1$H NMR (CDCl$_3$, 400 MHz): 7.71 (d, J=9.0 Hz, 1H), 7.2–7.28 (m, 11H), 7.08 (s, 1H), 6.89 (t, J=7.4 Hz, 1H), 6.78 (d, J=8 Hz, 1H), 6.33 (t, J=5.2 Hz, 1H), 5.2 (dd, J=4.5, 9.2 Hz 1H), 4.4–4.55 (m, 3H), 3.97 (dd, J=1.6, 11.1 Hz, 1H), 3.86 (dd, J=6.4, 11.3 Hz, 1H), 3.63 (m, 1H), 2.81 (m, 4H), 2.36 (s, 3H), 2.33 (m, 1H), 2.18 (m, 1H), 1.62 (s, 3H), 0.87 (s, 3H). LC-MS (M$^+$+1) (EI) 574.6

EXAMPLE 15

(αS,γR)-γ-[[((3S,4S)-3,4-dihydro-3-hydroxy-2H-1-benzopyran-4-yl)amino]carbonyl]-α-hydroxy-N-[1-[[[(2-methylphenyl)methyl]amino]carbonyl]cyclopentyl]benzene pentanamide

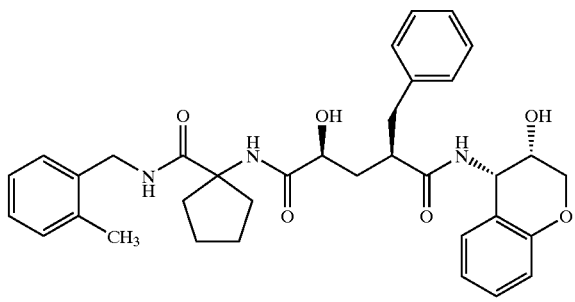

Step A

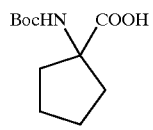

To a solution of 1-amino-1-cyclopentane carboxylic acid (5 g, 0.04 mol) in 403 mL of p-dioxane was added 43.4 mL of 1N sodium hydroxide solution. After 10 minutes di-tert-butyl Bicarbonate (10.4 g, 0.044 mol) was added and the resulting mixture stirred at room temperature for 20 hours. The reaction mixture was concentrated to half its volume and was then diluted with ethyl acetate (100 mL). The pH of the reaction mixture was adjusted to 2 by the drop wise addition of aqueous sodium hydrogen sulfate. The product was extracted with ethyl acetate (4×50 mL). The organic layers were combined, washed with brine, dried over anhydrous sodium sulfate and concentrated in vacuo to give the titled compound as a white solid. $^1$HNMR (DMSO 400 MHz): 1.8 (m, 4H), 1.6 (m, 4H), 1.25 (s, 9H). LC-MS (M$^+$+1−100) (EI) 233.3

Step B

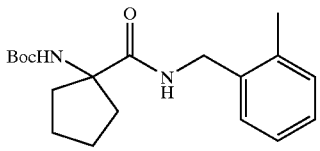

To a solution of intermediate obtained from Step A(1.0 g 4.36 mmol) in 10 mL, of dichloromethane was added 2-methyl benzylamine (0.65 mL, 5.23 mmol), dimethyl amino pyridine (53 mg, 0.43 mmol) and diisopropyl ethyl amine (1.14 mL, 6.54 mmol). 1-[3-(dimethylamino)propyl]-3-ethylcarbodiimide hydrochloride (1.25 g, 6.54 mmol) was added and the reaction stirred at room temperature under nitrogen for 18 hours. The reaction mixture was diluted with dichloromethane (100 mL) and washed successively with 10% citric acid, saturated sodium bicarbonate and brine solution. The organic layer was dried over anhydrous sodium sulfate, filtered and concentrated in vacuo. The crude material was purified by flash chromatography with 40% ethyl acetate-hexanes to give the title compound as a white solid. $^1$H NMR (CDCl$_3$, 400 MHz): 7.18–7.26 (m, 4H), 4.46 (d, 2H), 2.34 (s, 3H), 2.3 (m, 2H), 1.39–1.88 (m, 6 H).

Step C

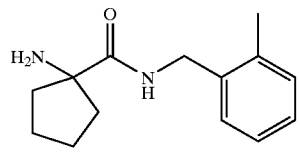

The title compound was prepared in accordance with the procedure described for Example 14 Step B.
$^1$H NMR (CDCl$_3$, 400 MHz): 8.0 (bs, 1H), 7.18–7.25 (m, 4H), 4.46 (d, J=5.7 Hz, 2H), 2.34 (s, 3H), 2.32 (m, 2H), 1.58–1.9 (m, 4H), 1.47–1.51 (m, 2H).

Step D

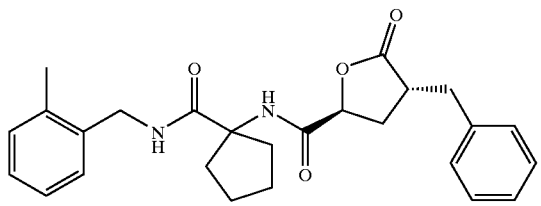

To a solution of intermediate prepared in Step C (180 mg, 0.77 mmol), intermediate prepared in Example 1 Step A (205 mg, 0.93 mmol) and 1-hydroxy-7-azabenzotriazole (158 mg, 1.16 mmol) in 2 mL of dichloromethane was added diisopropyl ethyl amine (162 μL, 0.93 mmol). 2-(1H-Benzotriazole-1-yl)-1,1,3,3-tetramethyluronium hexafluorophosphate (353 mg, 0.93 mmol) was added and the resulting reaction mixture stirred at room temperature for 20 hours. The reaction was diluted with dichloromethane (10 mL) and washed successively with 10% citric acid solution, saturated sodium bicarbonate solution and brine. The organic layer was dried over anhydrous sodium sulfate, filtered and concentrated in vacuo. The crude material was purified by flash chromatography with 40% ethyl acetate-hexanes to give the titled compound as a white solid. $^1$H NMR (CDCl$_3$, 400 MHz): 7.26–7.35 (m, 3H), 7.11–7.21 (m, 6H), 6.7 (bs, 1H), 6.51 (s, 1H), 4.51 (dd, J=5.1, 8.6 Hz, 1H), 4.42 (d, J=5.5 Hz, 2H), 3.12 (dd, J=4.3, 13.5 Hz, 1H), 2.79–2.88 (m, 3H), 2.03–2.35 (m, 6H), 1.95 (m, 1H), 1.81 (m, 1H)1.79 (m, 4H). LC-MS (M$^+$+1) (EI) 435.4

Step E

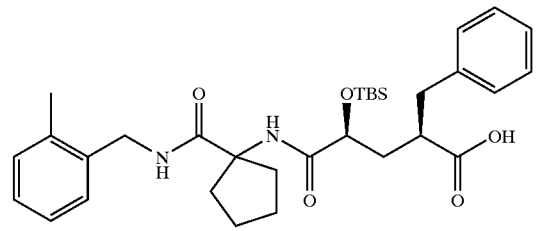

To a solution of the intermediate prepared in Step D (104 mg, 0.24 mmol) in 2 mL of p-dioxane was added a solution of lithium hydroxide monohydrate (10 mg, 0.26 mmol) in 2 mL of distilled water. The mixture was stirred at room temperature and the progress of the reaction was monitored by TLC. After 1.5 hours the reaction mixture was concentrated in vacuo. The product was azeotroped with toluene (3×10 mL) and dried under high vacuum. A white solid was obtained. N,N-dimethylformamide (3 mL) was added followed by imidazole (244 mg, 3.58 mmol) and tert-butyldimethylsilyl chloride (288 mg, 1.91 mmol). The resulting solution was stirred at room temperature for 24 hours. The reaction mixture was poured into pH=7 buffer solution and the product extracted with ethyl acetate (4×25 mL). The organic layers were combined and dried over anhydrous sodium sulfate and concentrated in vacuo to give the title compound (135 mg, 0.24 mmol) as an oil. The crude product was used in the next step without further purification. LC-MS (M$^+$+1)(EI)567.9.

Step F

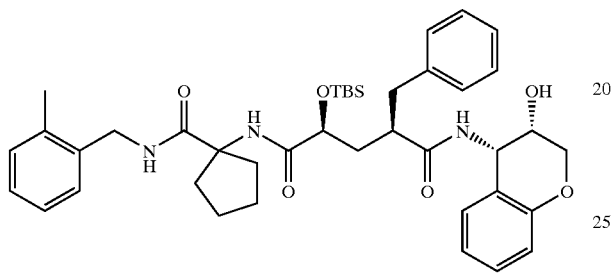

To a solution of the intermediate prepared in Step E (135 mg, 0.24 mmol), cis aminochromanol (47 mg, 0.29 mmol) and 1-hydroxybenzotriazole (48 mg, 0.36 mmol) in 2 mL of dichloromethane was added diisopropyl ethyl amine (62 μL, 0.36 mmol). 2-(1H-Benzotriazole-1-yl)-1,1,3,3-tetramethyluronium hexafluorophosphate (135 mg, 0.26 mmol) was added and the resulting reaction stirred at room temperature for 5 hours. The reaction was diluted with dichloromethane (10 mL) and washed successively with 10% citric acid, saturated sodium bicarbonate and brine. The organic layer was dried over anhydrous sodium sulfate, filtered and concentrated in vacuo. The crude material was purified with 40% ethyl acetate-hexanes to give the titled compound. $^1$H NMR(CDCl$_3$, 400 MHz): 7.67 ((d, J=8.6 Hz, 1H), 7.08–7.36 (m, 9H), 6.96 (s, 2H), 6.77–6.84 (m, 2H), 6.35 (t, J=3.4 Hz, 1H), 5.15 (dd, J=4.1 , 8.8 Hz, 1H), 4.55 (m, 2H), 4.37 (m, 1H), 3.83–3.93 (m, 2H), 3.51 (m, 1H), 2.77 (m, 3H), 2.4 (m, 1H), 2.33 (s, 3H), 2.24 (m, 1H), 1.8 (m, 3H), 1.6 (m, 3H), 1.05 (m, 1H), 0.96 (s, 9H), 0.86 (m, 1H), 0.23 (s, 6H). LC-MS (M$^+$+1) (EI)714.7

Step G:

(αS,γR)-γ-[[((3S,4S)-3,4-dihydro-3-hydroxy-2H-1-benzopyran-4-yl)amino]carbonyl]-α-hydroxy-N-[1-[[[(2-methylphenyl)methyl]amino]carbonyl]cyclopentyl]benzene pentanamide To a solution of the intermediate obtained in Step F (94 mg, 0.13 mmol) in 2 mL of anhydrous tetrahydrofuran was added tetrabutylammonium fluoride (144 μL, 0.14 mmol 1.0 M in tetrahydrofuran). The reaction mixture was stirred at room temperature and the progress of the reaction monitored by TLC. After 2 hours the starting material was consumed and the reaction mixture concentrated in vacuo. The crude material was purified by flash chromatography with 80% ethyl acetate-hexanes to give the titled compound. $^1$HNMR (CDCl$_3$, 400 MHz): 7.58 (d, J=8.6 Hz, 1H), 7.1–7.29 (m, 9H), 6.8–6.9 (m, 2H), 6.56 (m, 1H), 5.19 (dd, J=4.5, 9.4 Hz 1H), 4.5 (m, 3H), 3.8–3.95 (m, 2H), 3.6 (m, 1H), 3.05 (m, 1H), 2.8 (m, 2H), 2.35 (s, 3H), 2.3 (m, 2H), 2.05 (m, 2H), 1.4–1.8 (m, 8H). LC-MS (M$^+$+1) (EI)600.6

EXAMPLE 16

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-3,3-dimethyl-N-[(2,6-dimethylphenyl)-methyl]-2-pyrrolidinecarboxamide

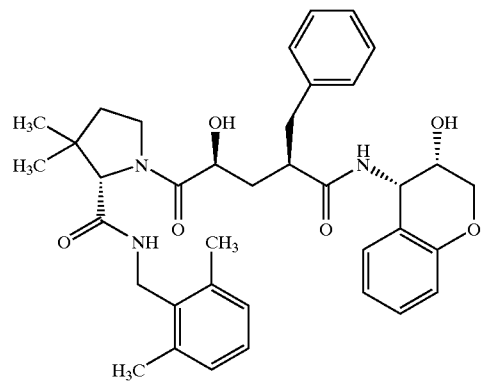

Step A

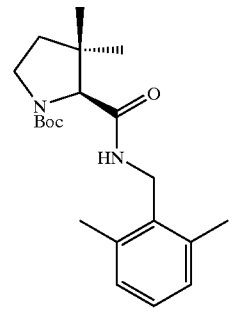

To a solution (2S)-3,3-Dimethyl-N-(Boc) praline (88 mg, 0.36 mmol) (for synthesis of this compound see Lubell, W. D., Sharma, R. *J. Org. Chem.*, 61 202, 1996) in 2 mL of dry dichloromethane was added 2,6-dimethylbenzylamine (75 mg, 0.43 mmol) and N,N-diisopropylethylamine (189 μL, 1.08 mmol). Bromo-tris-pyrrolidino-phosphonium hexafluorophosphate (202 mg, 0.43 mmol) was added and the reaction stirred at room temperature under nitrogen for three hours. The reaction mixture was diluted with dichloromethane (10 mL) and washed successively with 1N hydrochloric acid, and saturated sodium hydrogen carbonate solution. The organic layer was dried over anhydrous sodium sulfate, filtered and concentrated in vacuo. The crude material was purified by flash chromatography with 30% ethylacetate-hexanes to give the title compound as a white solid. $^1$H NMR (CDCl$_3$, 500 MHz) 7.15(m, 1H), 7.06(m, 2H), 5.59(bs, 1H), 4.46(m, 2H), 3.72(s, 1H), 3.48(bm, 2H), 2.37(s, 6H), 1.9(bm, 1H), 1.63(m, 1H), 1.38(s, 9H), 1.16(s, 3H), 1.08(s, 3H).

Step B

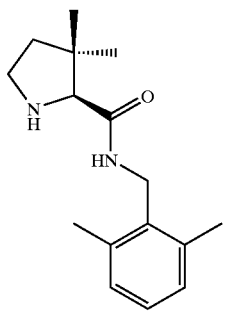

The intermediate prepared in Step A (118 mg, 0.32 mmol) was dissolved in dichloromethane (5 mL). Methanesulfonicacid (250 µL) was added and the reaction stirred at room temperature for 10 minutes. The reaction mixture was diluted with dichloromethane (10 mL) and washed with saturated solution of sodium carbonate. The organic layer was dried over anhydrous sodium sulfate filtered and concentrated in vacuo to give a colorless oil which was used in the next step without any further purification.

Step C

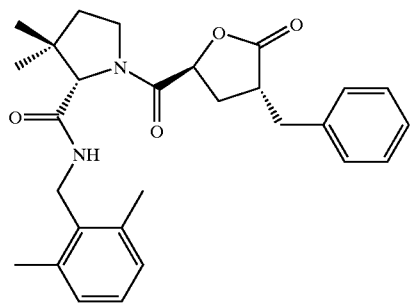

To a solution of the intermediate prepared in Step B (70 mg, 0.27 mmol), intermediate prepared in Example 1 Step A (118 mg, 0.54 mmol), and 1-hydroxy-7-azabenzotriazole (73 mg, 0.54 mmol) in 1 mL of 1:1 N,N-dimethylformamide-dichloromethane mixture was added benzotriazole-1-yl-oxy-tris-pyrrolidino-phosphonium hexafluorophosphate (280 mg. 0.54 mmol). The reaction mixture was stirred at room temperature for 16 hours. The reaction mixture was diluted with ethyl acetate (15 mL) and washed successively with 1N hydrochloric acid, saturated sodium hydrogen carbonate solution. The organic layer was dried over anhydrous sodium sulfate filtered and concentrated in vacuo. The crude material was purified by flash chromatography with 50% ethyl acetate-hexanes to give the title compound as a white solid. $^1$H NMR (CDCl$_3$, 500 MHz) 7.0–7.34 (m, 8H), 6.13 (bt, J=4.2 Hz, 1H), 4.87 (dd, J=2.5, 8.7 Hz, 1H), 4.52 (dd, J=5.5, 14.0 Hz, 1H), 4.36(dd, J=3.9, 14.0 Hz, 1H), 3.9(s, 1H), 3.65(m, 2H), 3.2 (dd, J=4.8, 14.0 Hz, 1H), 3.0(m, 1H), 2.9(dd, J=8, 14.0 Hz, 1H), 2.4 (m, 1H), 2.35(s, 6H), 2.25(m, 1H), 2.05(m, 1H), 1.65(m, 1H), 1.05(s, 3H), 1.02(s, 3H).

Step D

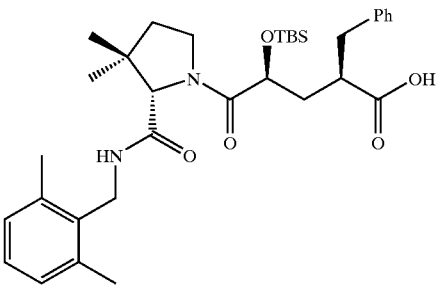

To a solution of the intermediate prepared in Step C (100 mg, 0.22 mmol) in 500 µL of p-dioxane was added a solution of 1N lithium hydroxide (250 µL). The reaction was stirred vigorously at room temperature for 1 hour. The reaction mixture was concentrated in vacuo. The product was azeotroped with toluene (4×10 mL) and dried under high vacuum. A white solid was obtained. N,N-dimethylformamide (2 mL) was added followed by imidazole (221 mg, 3.24 mmol) and tert-butyl-dimethyl-silylchloride (163 mg, 1.08 mmol). The resulting solution was stirred at room temperature for two hours. The reaction mixture was poured into pH=7 buffer solution and the product extracted with ethyl acetate (4×10 mL). The organic layers were combined and dried over anhydrous sodium sulfate and concentrated in vacuo to give the title compound as an oil. This material was used in the next step without further purification.

Step E

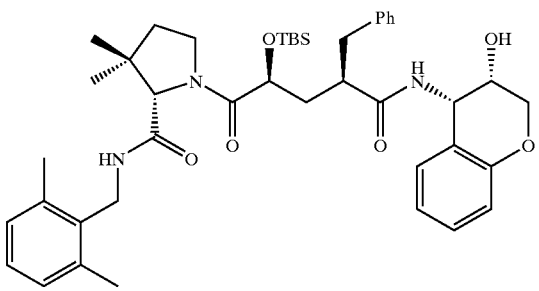

To a solution of the intermediate prepared in Step D (130 mg, 0.22 mmol), cis-aminochromanol (43 mg, 0.26 mmol) 1-hydroxy-7-azabenzotriazole (36 mg, 0.26 mmol) and N,N-diisopropylethyl amine (45 µL, 0.26 mmol) in 500 µL of 1:1 N,N-dimethyl formamide-dichloromethane was added Benzotriazole-1-yl-oxy-tris-pyrrolidino-phosphonium hexafluorophosphate (135 mg, 0.26 mmol). The reaction was stirred at roam temperature for 20 hours. The reaction mixture was diluted with ethyl acetate (20 mL) and washed successively with 1N hydrochloric acid, saturated sodium hydrogen carbonate and saturated sodium chloride solution. The organic layer was dried over anhydrous sodium sulfate filtered and concentrated in vacuo. The crude material was purified by flash chromatography with 50% ethylacetate hexanes to give a white solid. $^1$H NMR (CDCl$_3$, 500 MHz) 6.8–7.2 (m, 12H), 6.25 (d, 3=7.5 Hz, 1H), 5.42 (bt, 1H), 5.05 (m, 1H), 4.2–4.45 (m, 4 H), 4.15 (m, 2H), 3.9 (m, 3H), 3.8 (m, 2H), 3.6 (m, 2H), 2.28 (s, 3H), 2.27 (s, 2H), 1.95 (m, 2H), 1.7 (m, 2H), 1.0 (s, 3H), 0.97 (s, 3H), 0.9 (s, 9H), 0.1 (s, 3H), 0.0 (s, 3H).

Step F (4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-3,3-dimethyl-N-[(2,6-dimethylphenyl)-methyl]-2-pyrrolidine-carboxamide To a solution of intermediate obtained from Step E (95 mg, 0.13 mmol) in 1 mL of anhydrous tetrahydrofuran was added tetrabutylammonium fluoride (140 μL, 0.14 mmol, 1.0 M in tetrahydrofuran), The reaction mixture was stirred at room temperature for 3 hours. The reaction mixture was concentrated in vacuo and purified by flash chromatography with 100% ethyl acetate to give the title compound as a white solid. $^1$H NMR (CDCl$_2$, 500 MHz) 6.6–7.4 (M, 12H), 5.89 (d, J=7.7 Hz, 1H), 5.72 (d, J=8.5 Hz, 1H), 5.45 (bt, 1H), 5.19 (dd, J=3.9, 7.8 Hz, 1H), 4.52 (dd, J=5.0, 14.0 Hz, 1H), 4.43 (dd, J=4.1, 14 Hz, 1H), 4.37(m, 2H), 4.25(s,1H), 3.9–4.1(m, 4H), 3.85(m, 2H), 3.6(m,2H), 3.05(m,1H), 2.85 (m,3H), 2.4(s,3H), 2.2(s,3H), 1.15(s,6H). LC-MS (M$^+$+1) (EI)628.3

EXAMPLE 17

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-3,3-dimethyl-N-[(3-methyl-2-pyridylmethyl)]-2-pyrrolidinecarboxamide

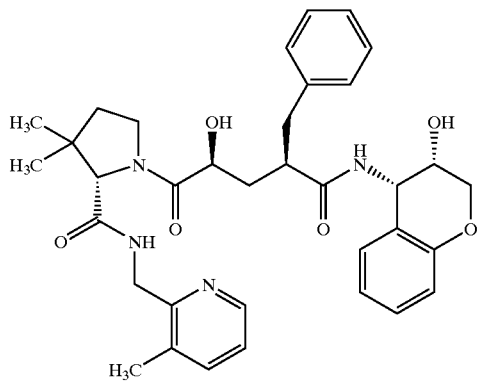

Step A

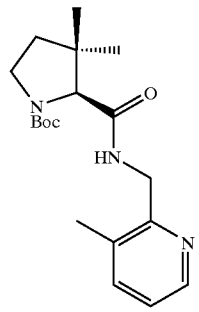

To a solution (2S)-3,3-Dimethyl-N-(Boc) proline (118 mg, 0.48 mmol) in dry dichloromethane (2 ml) was added 2-pyridyl-6-methyl benzylamine (138 mg, 0.58 mmol) and N,N-diisopropylethylamine (253 μL, 1.45 mmol). Bromo-tris-pyrrolidino-phosphonium hexafluorophosphate (271 mg, 0.58 mmol) was added and the reaction stirred at room temperature under nitrogen for 16hours. The reaction mixture was diluted with dichloromethane (10 mL) and washed successively with 1N hydrochloric acid, and saturated sodium hydrogen carbonate solution. The organic layer was dried over anhydrous sodium sulfate, filtered and concentrated in vacuo. The crude material was purified by flash chromatography with 65% ethylacetate-hexanes to give the title compound as a white solid. $^1$H NMR (CDCl$_3$, 500 MHz) 8.2 (bs, 1H), 7.72 (m, 1H), 7.16 (m, 1H), 4.52 (s, 1H), 3.9 (m, 1H), 3.65(m, 2H), 2.4 (s, 3H), 1.34 (s, 9H), 1.22 (s, 3H), 1.07 (s, 3H).

Step B

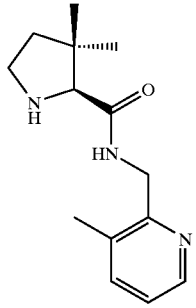

The intermediate prepared in Step A (80 mg, 0.23 mmol) was dissolved in dichloromethane (5 mL). Methanesulfonic acid (250 μL) was added and the reaction stirred at room temperature for 10 minutes. The reaction mixture was diluted with dichloromethane (10 mL) and washed with saturated solution of sodium carbonate. The organic layer was dried over anhydrous sodium sulfate filtered and concentrated in vacuo to give a colorless oil which was used in the next step without any further purification.

Step C

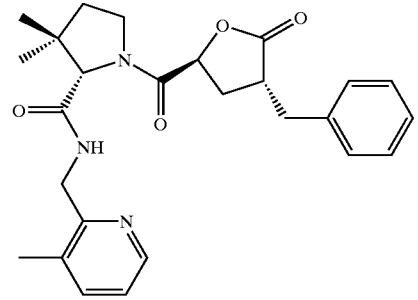

To a solution of the intermediate prepared in Step B (57 mg, 0.23 mmol), intermediate prepared in Example 1 Step A (101 mg, 0.46 mmol), and 1-hydroxy-7-azabenzotriazole (136 mg, 1.04 mmol) in 1 mL of 1:1 N,N-dimethylformamide-dichloromethane mixture was added Benzotriazole-1-yl-oxy-tris-pyrrolidino-phosphonium hexafluorophosphate (520 mg. 1.04 mmol). The reaction mixture was stirred at room temperature for 16 hours. The reaction mixture was diluted with ethylacetate (15 mL) and washed successively with 1N hydrochloric acid, saturated sodium hydrogen carbonate solution. The organic layer was dried over anhydrous sodium sulfate filtered and concentrated in vacuo. The crude material was purified by flash chromatography with 80% ethylacetate-hexanes to give the desired product as a pink foam.

Step D

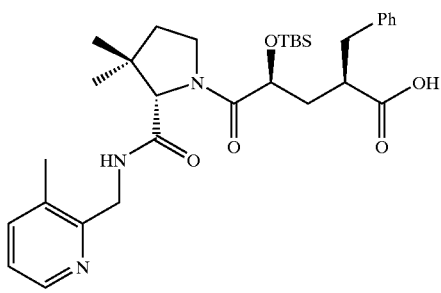

To a solution of the intermediate prepared in Step C (57 mg, 0.12 mmol) in 1 mL of p-dioxane was added a solution of 1N lithium hydroxide (140 μL). The reaction was stirred vigorously at room temperature for 2 hours. The reaction mixture was concentrated in vacuo. The product was azeotroped with toluene (4×10 mL) and dried under high vacuum. A white solid was obtained. N,N-dimethylformamide (2 mL) was added followed by imidazole (129 mg, 1.89 mmol) and tert-butyl-dimethyl-silylchloride (94 mg, 0.63 mmol). The resulting solution was stirred at room temperature for 16 hours. The reaction mixture was poured into pH=7 buffer solution and the product extracted with ethyl acetate (4×10 mL). The organic layers were combined and dried over anhydrous sodium sulfate and concentrated in vacuo to give the title compound as an oil. This material was used in the next step without further purification.

Step E

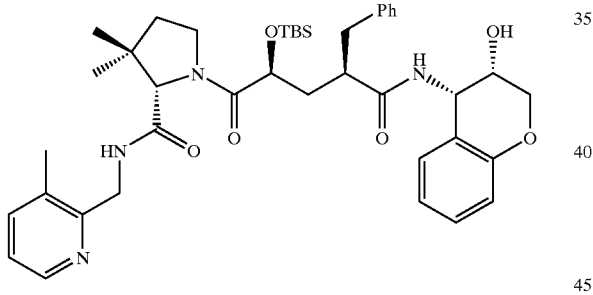

To a solution of the intermediate prepared in Step D (73 mg, 0.12 mmol), cis-aminochromanol (25 mg, 0.15 mmol) 1-hydroxy-7-azabenzotriazole (21 mg, 0.15 mmol) and N,N-diisopropylethyl amine (26 μL, 0.15 mmol) in 900 μL, of 1:1 N,N-dimethyl formamide-dichloromethane was added Benzotriazole-1-yl-oxy-tris-pyrrolidino-phosphonium hexafluorophosphate (79 mg, 0.15 mmol). The reaction was stirred at room temperature for 20 hours. The reaction mixture was diluted with ethyl acetate (20 mL) and washed successively with 1N hydrochloric acid, saturated sodium hydrogen carbonate and saturated sodium chloride solution. The organic layer was dried over anhydrous sodium sulfate filtered and concentrated in vacuo. The crude material was purified by flash chromatography with 70% ethylacetate hexanes to give a white solid. $^1$H NMR (CDC$_3$, 500 MHz) 8.3(bt, 1H), 7.64(bt, 1H), 7.3(m, 4H), 7.1(m,1H), 7.0(m, 1H), 6.9(m, 1H), 6.8(q, $^1$H), 6.6(d, J=8.0 Hz, 1H), 6.5(d, J=8.0 Hz, 1H), 5.13 (dd, J=3.9, 8.9 Hz, 1H), 4.05–4.4 (m, 5H), 3.6–4.0(m, 4H), 3.05(m, 1H), 2.8(m, 2H), 2.2 (s, 3H), 2.05(m, 1H), 1.95(m, 1H), 1.8(m, 1H), 1.2 (s, 3H), 1.05(s, 3H), 0.95(s, 9H), 0.05(s, 3H), 0.02(s, 3H).

Step F (4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-3,3-dimethyl-N-[(3-methyl-2-pyridylmethyl)]-2-pyrrolidinecarboxamide To a solution of intermediate obtained from Step E (43 mg, 0.06 mmol) in 1 mL of anhydrous tetrahydrofuran was added tetrabutylammonium fluoride (200 μL, 0.2 mmol, 1.0 M in tetrahydrofuran). The reaction mixture was stirred at room temperature for 2 hours: The reaction mixture was concentrated in vacuo and purified by flash chromatography with 3% methanol-ethyl acetate to give the title compound as a white solid. $^1$H NMR (CDCl$_3$, 500 MHz) 6.8–7.4 (m, 12H), 6.7 (bt, 1H), 6.0(m, 1H), 4.1–4.5(m, 3H), 3.4–4.0(m, 6H), 3.1 (m, 1H), 2.8(m, 2H), 2.6(m, 1H), 2.4(s, 3H), 2.0(m, 1H), 1.4–1.6(m, 4H), 1.15(m, 6H). LC-MS (M$^+$+1)(EI) 615.4

EXAMPLE 18

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2,6-dimethylphenyl) methyl]-4-oxazolidinecarboxamide

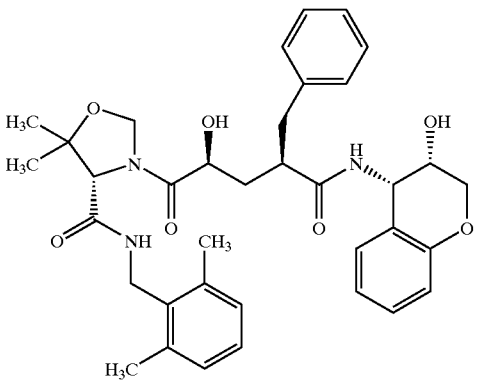

Step A

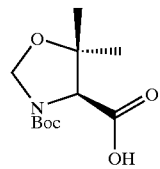

To a solution of (S)-2-amino-3-hydroxy-3-methyl-butanoic acid (500 mg, 3.75 mmol) in 2 N sodium hydroxide (3.75 mL, 7.5 mmol) at 0° C. was added 37% solution of formaldehyde (3.75 mL). The resulting solution was left stirring at room temperature for 16 hours. p-Dioxane (2 mL) was added to the reaction mixture followed by di-tert-butyl-dicarbonate (819 mg, 3.75 mmol) and the reaction stirred at room temperature far 3 hours. The reaction mixture was concentrated to half its volume. A saturated solution of sodium hydrogen sulfate was added to the reaction mixture until the pH was 2. The aqueous layer was extracted with ethyl acetate (4×10 mL). The organic layers were combined and dried over anhydrous sodium sulfate filtered and concentrated in vacuo to give a white solid. NMR (CDCl$_3$, 500 MHz) 8.9 (bs, 1H), 5.0 (t, J=44 Hz, 2H), 4.14 (d, J=54 Hz, 1H), 1.45 (s, 12 H), 1.37 (s, 3H).

Step B

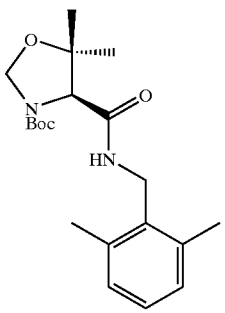

To a solution of the intermediate prepared in step A(150 mg, 0.61 mmol) in 2 mL of dry dichloromethane was added 2,6-dimethylbenzylamine (182 mg, 0.73 mmol) and N,N-diisopropyl ethyl amine (382 μL, 2.19 mmol). Bromo-tris-pyrrolidino-phosphonium hexafluorophosphate (341 mg, 0.73 mmol) was added and the reaction stirred at room temperature under nitrogen for 48 hours. The reaction mixture was diluted with dichloromethane (10 mL) and washed successively with 1N hydrochloric acid, and saturated sodium hydrogen carbonate solution. The organic layer was dried over anhydrous sodium sulfate, filtered and concentrated in vacuo. The crude material was purified by flash chromatography with 30% ethylacetate-hexanes to give the title compound as a white solid. $^1$H NMR (CDCl$_3$, 500 MHz) 7.17 (m, 1H), 7.05 (m, 2H), 5.9 (bs, 1H), 5.0 (bs, 1H), 4.88 (d, J=4.88 Hz, 1H), 4.5 (m, 2H), 3.98 (s, 1H), 2.38 (s, 6H), 1.46 (s, 3H), 1.41 (s, 9H), 1.34 (s, 3H).

Step C

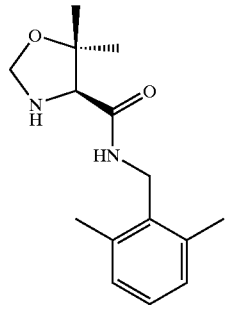

The intermediate prepared in Step B (146 mg, 0.4 mmol) was dissolved in dichloromethane (5 mL). Methanesulfonic acid (450 μL, was added and the reaction stirred at room temperature for 10 minutes. The reaction mixture was diluted with dichloromethane (10 mL) and washed with saturated solution of sodium carbonate. The organic layer was dried over anhydrous sodium sulfate filtered and concentrated in vacuo to give a white solid which was used in the next step without any further purification.

Step D

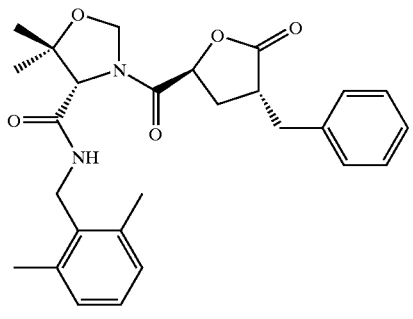

To a solution of the intermediate prepared in Step C (95 mg, 0.36 mmol), intermediate prepared in Example 1 Step A (160 mg, 0.72 mmol), and 1-hydroxy-7-azabenzotriazole (98 mg, 0.72 mmol) in 2 mL of 1:1 N,N-dimethylformamide-dichloromethane mixture was added Benzotriazole-1-yl-oxy-tris-pyrrolidino-phosphonium hexafluorophosphate (376 mg. 0.72 mmol). The reaction mixture was stirred at room temperature for 16 hours. The reaction mixture was diluted with ethyl acetate (15 mL) and washed successively with 1N hydrochloric acid, saturated sodium hydrogen carbonate solution. The organic layer was dried over anhydrous sodium sulfate filtered and concentrated in vacuo. The crude material was purified by flash chromatography with 50% ethylacetate-hexanes to give the desired product as a white solid. $^1$H NMR (CDC$_3$, 500 MHz) 7=7.2 (m, 8H), 5.9 (bs, 1H), 5.16 (dd, J=3.4, 12.3 Hz, 2 H), 4.65 (dd, J=2.9, 8.7 Hz, 1H), 4.5 (m, 2H), 4.43 (dd, J=3.9, 13.7 Hz, 1H), 4.07 (s, 1H), 3.15 (dd, J=4.8, 14 Hz, 1H), 3.05 (m, 1H), 2.9 (dd, J=8, 13.7 Hz, 1H), 2.55 (m, 1H), 2.37 (s, 3H), 2.35 (s, 3H), 1.13 (s, 6H). LC-MS (M$^+$+1)(EI) 465.2

Step E

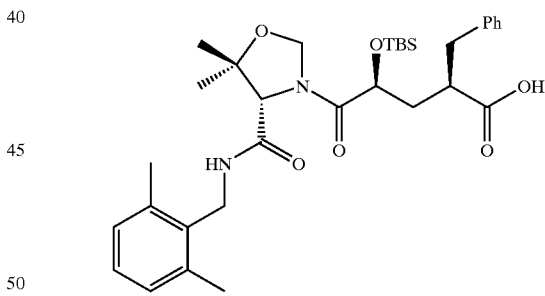

To a solution of the intermediate prepared in Step D (110 mg, 0.24 mmol) in 1.5 mL of p-dioxane was added a solution of 1N lithium hydroxide (260 μL). The reaction was stirred vigorously at room temperature for 1 hour. The reaction mixture was concentrated in vacuo. The product was azeotroped with toluene (4×10 mL) and dried under high vacuum. A white solid was obtained. N,N-dimethylformamide (2 mL) was added followed by imidazole (161 mg, 2.36 mmol) and tert-butyl-dimethyl-silylchloride (178 mg, 1.18 mmol). The resulting solution was stirred at room temperature for 16 hours. The reaction mixture was poured into pH=7 buffer solution and the product extracted with ethyl acetate (4×10 mL). The organic layers were combined and dried over anhydrous sodium sulfate and concentrated in vacuo to give the title compound as an oil. This material was used in the next step without further purification.

Step F

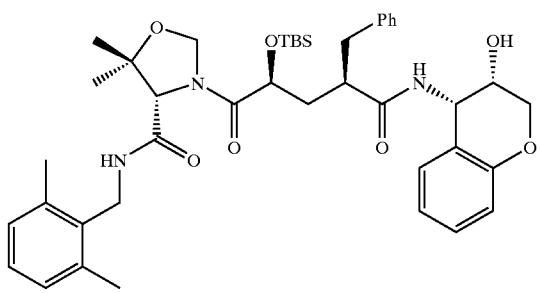

To a solution of the intermediate prepared in Step E (140 mg, 0.24 mmol), cis-aminochromanol (47 mg, 0.28 mmol) 1-hydroxy-7-azabenzotriazole (38 mg, 0.28 mmol) and N,N-diisopropylethyl amine (49 µL, 0.28 mmol) in dichloromethane (1 mL) was added Benzotriazole-1-yl-oxy-tris-pyrrolidino-phosphonium hexafluorophosphate (148 mg, 0.28 mmol). The reaction was stirred at room temperature for 20 hours. The reaction mixture was diluted with ethylacetate (20 mL) and washed successively with 1N hydrochloric acid, saturated sodium hydrogen carbonate and saturated sodium chloride solution. The organic layer was dried over anhydrous sodium sulfate filtered and concentrated in vacuo. The crude material was purified by flash chromatography with 50% ethylacetate hexanes to give a white solid. $^1$H NMR (CDCl$_3$, 500 MHz) 6.8–7.2 (m, 12H), 5.81 (d, J=7.7 Hz, 1H), 5.5 (bt, 1H), 5.1–5.25 (m, 4H), 4.5 (m, 1H), 4.4 (m, 1H), 4.2 (m, 1H), 4.1 (s, 1H), 4.05 (m, 1H), 3.8(m, 2H), 2.9 (m, 2H), 2.7 (m, 1H), 2.37(s, 3H), 2.33(s, 3H), 1.7–1.85 (m, 2H), 1.44 (s, 3H), 1.35(s, 3H), 0.8 (s, 9H), 0.0 (s, 3H), −0.06(s, 3H). LC-MS (M$^+$+1)(EI) 744.4

Step G (4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2,6-dimethylphenyl) methyl]-4-oxazolidinecarboxamide To a solution of intermediate obtained from Step F (112 mg, 0.15 mmol) in 1.5 mL of anhydrous tetrahydrofuran was added tetrabutylammonium fluoride (165 µL, 0.16 mmol, 1.0 M in tetrahydrofuran). The reaction mixture was stirred at room temperature for 1 hour. The reaction mixture was concentrated in vacuo and purified by flash chromatography with 80% ethyl acetate to give the title compound as a white solid. $^1$H NMR (CDCl$_3$, 500 MHz) 6.9–7.2(m, 12H), 6.4(bt, 1H), 5.92(dd, J=8.7, 11.7 Hz, 1H), 5.5 (bt, 1H), 5.35 (d, J=4.8 Hz, 1H), 5.17 (dd, J=4.1, 7.6 Hz, 1H), 5.0 (d, J=4.3 Hz, 1H), 4.5 (m, 2H), 4.42 (s, 1H), 4.05 (m, 3H), 3.85 (m, 2H), 2.9 (m, 2H), 2.5(m, 1H), 2.36(s, 3H), 2.26(s, 3H), 2.05(m, 1H), 1.95(m, 1H), 1.36(s, 6H). LC-MS (M$^+$+1)(EI) 630.2

EXAMPLE 19

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2,6-dimethylphenyl) methyl]-4-thiazolidinecarboxamide

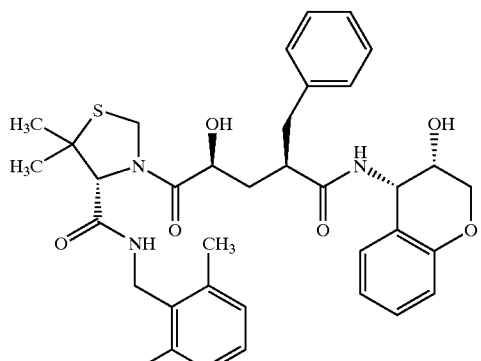

Step A

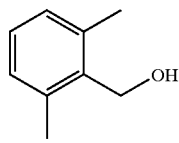

To a solution of ethyl 2,6-dimethyl phenyl carboxylate (5.0 g, 28 mmol) in THF at 0° C., Lithium aluminum hydride (30.8 mL, 30.8 mmol, 1M in THF) was added. The solution was then stirred at room temperature for 4 h. THF was removed and 2N NaOH solution was added. The mixture was extracted with methylene chloride (3×100 mL). The combined methylene chloride layers were washed with brine and dried over sodium sulfate. Upon removal of the solvent, the titled compound was obtained as a white solid. $^1$H NMR (CDCl$_3$, 400 MHz): 7.10 (m, 3H), 4.78 (s, 2H), 2.44 (s, 6H).

Step B

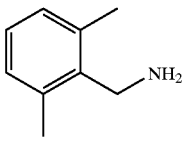

Phthalimide (5.26 g, 35.84 mmol) was added to a solution of the title compound from Step A (3.25 g, 23.89 mmol), triphenylphosphine (9.39 g, 35.84 mmol), diethyl azodicarboxylate (5.67 mL, 35.84 mmol) in THF (100 mL) at 0° C. The solution was stirred at room temperature for 4 h. Water (50 mL) was added. The mixture was extracted with EtOAc (3×50 mL). The combined EtOAc layers were washed with brine and dried over sodium sulfate. Flash column using EtOAc/hexane 2:8 as the elute afforded a white solid. To a solution of the solid (from above step) in methylene chloride (100 mL), hydrazine hydrate (10 mL) was added. The mixture was stirred at room temperature overnight. Water (100 mL) was added. The mixture was extracted with methylene chloride (3×100 mL). The combined methylene chloride layers were washed with brine, and dried over sodium sulfate. The titled compound was obtained as a white solid after flash column using CH$_2$Cl$_2$/MeOH 9:1 as the elute. $^1$H NMR ((CDCl$_3$, 400 MHz): 7.07 (m, 3H), 3.86 (s, 2H), 2.46 (s, 3H), 2.41(s, 3H).

Step C

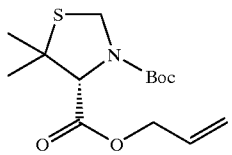

To a mixture of the titled compound from Example 1, Step B (6.10 g, 23.4 mmol) in DMF (20 mL) at room temperature, allyl bromide (2.42 mL, 28 mmol) and triethyl amine (4.92 mL, 35 mmol) were added. The mixture was stirred at room temperature for 2 days. Water (100 mL) was added. The mixture was extracted with EtOAc (3×150 mL). The combined EtOAc layers were washed with brine and dried over sodium sulfate. The titled compound was obtained as an oil after flash column using EtOAc/hexane 1:9 as the elute. $^1$H NMR (CDCl$_3$, 400 MHz, mixture of rotamers): 5.93 (m, 1H), 5.32 (m, 2H), 4.72 (m, 4H), 4.39 (s, 2/5 H), 4.20 (s, 3/5 H), 1.60 (s, 6H), 1.42 (m, 9H).

Step D

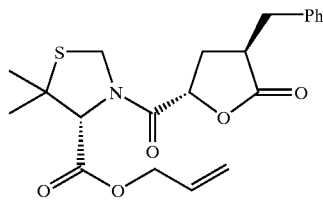

To a solution of the titled compound from Step C (5.60 g, 18.60 mmol) in methylene chloride (50 mL) at room temperature, TFA (10 mL) was added. The solution was stirred at room temperature overnight. The solvent was removed via vacuum. Saturated aqueous sodium bicarbonate solution (50 mL) was added. The mixture was extracted with methylene chloride (3×50 mL). The combined methylene chloride layers were washed with brine and dried over sodium sulfate. Upon removal of the solvent, the residue was then dissolved in methylene chloride (50 mL). To the solution, the titled compound from Example 1, Step A (4.91 g, 22 mmol), bromo-tris-pyrrolidino-phosphonium hexafluorophosphate (11.61 g, 22 mmol), diisopropylethyl amine (6.48 mL, 37.2 mmol) and 1-hydroxy-7-azabenzotriazole (3.0 g, 22 mmol, HOAT) were added. The mixture was stirred at room temperature for 2 days. Methylene chloride (200 mL) was added and the solution was washed with saturated sodium bicarbonate (50 mL), brine (100 mL), and dried over sodium sulfate. The titled compound was obtained as a white solid after flash column using EtOAc/hexane 3:7 as the elute. $^1$H NMR (CDCl$_3$, 400 MHz): 7.22 (m, 5H), 5.90 (m, 1H), 5.34 (m, 2H), 4.40–4.97 (m, 6H), 3.19 (m, 2H), 2.83 (m, 1H), 2.61 (M, 1H), 2.18 (m, 1H), 1.50 (m, 15H).

Step E

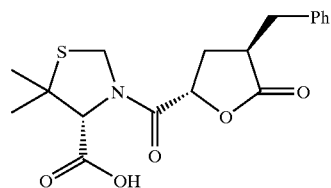

To a solution of the titled compound from Step D (4.33 g, 10.74 mmol) and morpholine (9.38 mL, 107.4 mmol) in THF (20 mL), tetrakis(triphenylphosphine)-palladium (0) (1.25 g, 1.07 mmol) was added. The whole was stirred at room temperature under nitrogen for 3 h. THF was removed. 20 mL of 1N HCl was added. The mixture was extracted with EtOAc (3×50 mL). The combined EtOAc layers were washed with water, brine, and dried over sodium sulfate. The titled compound was obtained as a yellow solid after removal of the solvent. $^1$H NMR (CDCl$_3$, 500 MHz): 7.30 (m, 5H), 4.95 (m, 1H), 4.82 (m, 1H), 4.70 (m, 1H), 4.52 (s, 1H), 3.20 (m, 2H), 2.87 (m, 1H), 2.62 (m, 1H), 2.18 (m, 1H), 1.60 (s, 3H), 1.50 (s, 3H).

Step F

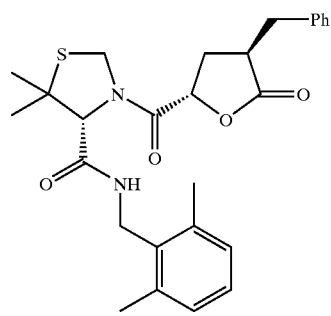

A mixture of the titled compound from Step E (2.00 g, 5.50 mmol), the titled compound from Step B (0.89 g, 6.61 mmol), EDC (1.27 g, 6.61 mmol), HOAT (0.90 g, 6.61 mmol) and diisopropylethyl amine (1.44 mL, 8.26 mmol) in methylene chloride (50 mL) was stirred at room temperature overnight. The solution was washed with water (20 mL), brine (20 mL), and dried over sodium sulfate. The titled compound was obtained as a white solid after flash column using EtOAc/hexane 3:7 as the elute. $^1$H NMR (CDCl$_3$, 300 MHz, 1:1 mixture of rotamers): 7.0–7.6 (m, 8H), 6.00 (br s, 1/2H), 5.80 (br s, 1/2H), 4.30–4.85 (m, 6H), 4.26 (s, 1/2H), 4.02 (s, 1/2H), 3.15 (m, 2H), 2.80 (m, 1H), 2.40 (s, 3H), 2.30 (s, 3H), 2.11 (m, 1H), 1.60 (s, 3H), 1.51 (m, 3H).

Step G

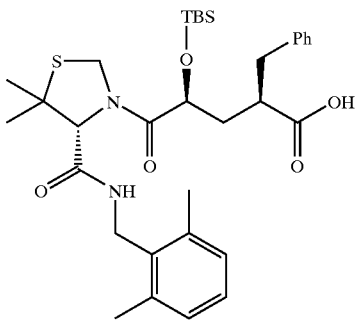

To a solution of the titled compound from Step F (2.34 g, 4.87 mmol) in p-dioxane (50 mL) at room temperature, 1 M LiOH (536 mL, 5.36 mmol) was added. The solution was stirred at room temperature overnight. The solvent was removed. The trace of water was azatropically removed with toluene (3×20 mL). The resulting white solid was dried under high vacuum for 2 h. The residue was mixed with EtOAc (100 mL), diisopropylethyl amine (3.40 mL, 19.5 mmol), and tert-butyldimethylsilyl trifluoromethane-sulfonate (2.24 mL, 9.75 mmol, TBSOTf). The mixture was stirred at room temperature for 5 h until the solvent was clear. LC/MS showed no starting material left. The solution was washed with water (20 mL), brine(20 mL), and dried over sodium sulfate. Upon removal of the solvent, the residue was dissolved in THF (50 mL), and water (10 mL) was added. The solution was stirred at room temperature overnight. The solvent was removed and dried under high vacuum. The titled compound was obtained as a pale oil. LC-MS (M$^+$+1) (EI) 613.4.

Step H

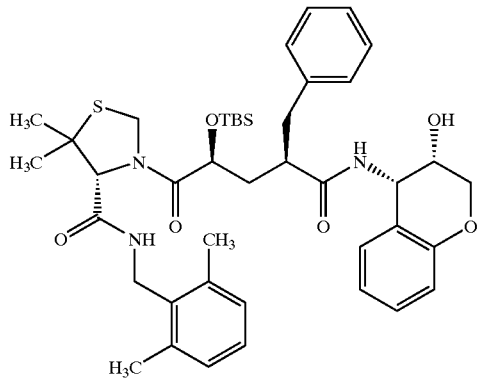

A mixture of the titled compound from Step G (1.55 g, 2.53 mmol), cis-aminochromanol (0.50 g, 3.0 mmol), diisopropylethyl amine (2.2 mL, 12.66 mmol), O-benzotriazol-1-yl-N,N,N',N'-tetramethyluronium hexafluoro-phosphate (2.40 g, 6.33 mmol) and catalytic amount of HOAT in DMF (20 mL) was stirred at room temperature overnight. Water (50 mL) was added. The mixture was extracted with EtOAc (3×100 mL). The combined EtOAc layers were washed with brine (100 mL) and dried over sodium sulfate. The titled compound was obtained as a white solid after flash column using EtOAc/hexane 4:6 as the elute. $^1$H NMR (CDCl$_3$, 400 MHz, 1:1 mixture of rotamers): 6.80–7.40 (m, 12 H), 6.58 (br s, 0.5H), 5.82 (m, 0.5H), 5.68 (m, 0.5H), 5.50 (br s, 0.5H), 5.15 (m, 0.5H), 4.90 (m, 0.5H), 3.80–4.88 (m, 9H), 2.80 (m, 2H), 2.05–2.40 (m, 8H), 1.80 (m, 1H), 1.40–1.60 (m, 6H), 0.92 (s, 4.5H), 0.83 (s, 4.5H), 0.00 (m, 6H).

Step I (4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2,6-dimethylphenyl)methyl]-4-thiazolidinecarboxamide A solution of the titled compound from Step H (1.33 g, 1.75 mmol) and 1 M tetrabutyl-ammonium fluoride (2.63 mL, 2.63 mmol) in THF was stirred at room temperature for 4 h. The solvent was removed. The titled compound was obtained as a white solid after flash column using EtOAc/hexane 7:3 as the elute. $^1$H NMR (CDCl$_3$, 400 MHz, 1:1 mixture of rotamers): 6.80–7.40 (m, 12H), 6.42 (br s, 1/2H), 5.90 (m, 1H), 5.52 (br s, 1/2H), 5.19 (m, 1/2H), 4.20–4.88 (m, 6.5H), 4.00 (m, 2H), 3.72 (m, 1H), 2.60–3.18 (m, 4H), 2.40 (s, 3H), 2.25 (s, 3H), 2.07 (m, 1H), 1.40–1.65 (m, 9H). LC-MS (M++1) (EI) 646.3.

EXAMPLE 20

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(3-methyl-2-pyridinylmethyl)]-4-thiazolidinecarboxamide

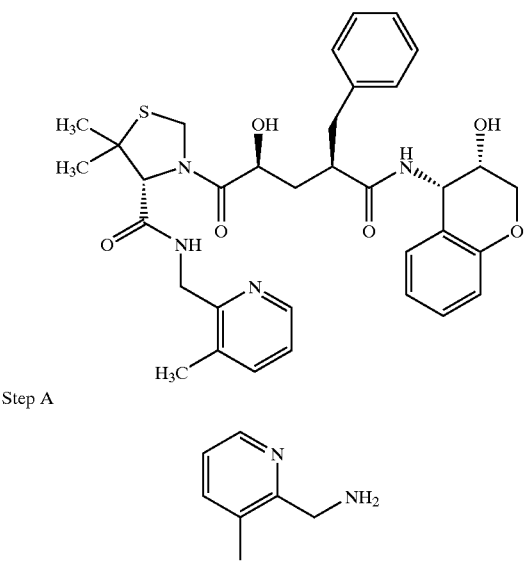

Step A

A mixture of 2-cyano-3-methylpyridine (1.00 g, 8.47 mmol), catalytic amount of palladium on carbon (10%) and 2 mL of concentrated HCl in 30 mL of EtOH was charged with hydrogen at 40 psi at room temperature for 2 h. The mixture was then filtered through celite and washed with EtOH (3×10 mL). The filtrate was concentrated via vacuum to give a light yellow solid as the titled compound. $^1$H NMR (CDCl$_3$, 400 MHz): 8.42 (m, 1H), 7.44 (m, 1H), 7.10 (m, 1H), 3.99 (s, 2H), 2.33 (s, 3H).

Step B

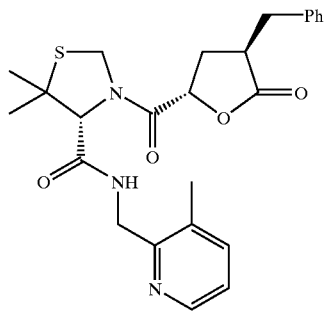

A mixture of the titled compound from Step A (0.67 g, 5.5 mmol), the titled compound from Example 19, Step E (2.00 g, 5.5 mmol), EDC (1.27 g, 6.61 mmol), HOAT (0.899 g, 6.6 mmol), and diisopropylethyl amine (1.44 mL, 8.26 mmol) in 50 mL of methylene chloride was stirred at room temperature overnight. The solution was washed with water (20 mL), brine (10 mL), and dried over sodium sulfate. The titled compound was obtained as a white solid after flash column using EtOAc/hexane 8:2 as the elute. $^1$H NMR (CDCl$_3$, 400 MHz, 2:3 mixture of rotamers): 8.38 (m, 2/5H), 8.20 (m, 3/5H), 8.08 (m, 2/5H), 7.78 (m, 3/5H), 7.10–7.72 (m, 6H), 4.80–5.05 (m, 3H), 4.08–4.60 (m, 3H), 3.08 (m, 2H), 2.78 (m, 2H), 2.12 (m, 4H), 1.50 (m, 6H).

Step C

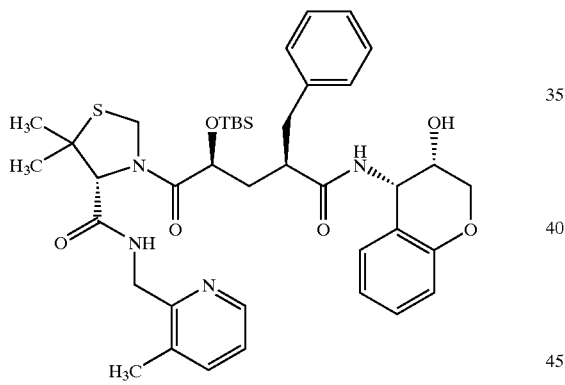

To a solution of the titled compound from Step B (1.20 g, 2.57 mmol) in dioxane (20 mL), 1M LiOH (2.83 mL, 2.83 mmol) was added. The solution was stirred at room temperature for 6 h. The solvent was removed and the trace of water was removed azatropically with toluene (3×20 mL). The residue was dried under high vacuum for 4 h. The resulting solid was then mixed with 50 mL of EtOAc, diisopropylethyl amine (2.69 mL, 15.4 mmol), and TBSOTf (1.77 mL, 7.7 mmol). The mixture was stirred at room temperature for 5 h until it became clear. LC/MS showed no starting material left. The solution was washed with water (10 mL), brine (10 mL), and dried over sodium sulfate. Upon removal of the solvent, the residue was mixed with 1:5 of water/THF (20 mL). The mixture was stirred at room temperature overnight. LC/MS showed that only the acid existed. The solvent was removed and dried under high vacuum. The resulting white solid was then mixed with cis-aminochromanol (0.42 g, 2.57 mmol), diisopropylethyl amine (2.23 mL, 12.84 mmol), O-benzotriazol-1-yl-N,N,N', N'-tetramethyluronium hexafluoro-phosphate (2.43 g, 6.42 mmol) and catalytic amount of HOAT in DMF (20 mL) was stirred at room temperature overnight. Water (50 mL) was added. The mixture was extracted with EtOAc (3×100 mL). The combined EtOAc layers were washed with brine (100 mL) and dried over sodium sulfate. The titled compound was obtained as a white solid after flash column using EtOAc/hexane 8:2 as the elute. $^1$H NMR (CDCl$_3$, 400 MHz, 2:3 mixture of rotamers): 8.38 (m, 2/5H), 8.35 (m, 3/5H), 8.09 (m, 2/5H), 7.98 (m, 3/5H), 6.64–7.45 (m, 10H), 6.20 (m, 3/5H), 5.60 (m, 2/5H), 5.20 (m, 1H), 4.72–4.98 (m, 3H), 4.54 (s, 3/5H), 3.78–4.50 (m, 5H), 3.50 (s, 2/5H), 2.76–3.00 (m, 3H), 2.40 (m, 1H), 2.20 (s, 9/5H), 2.12 (s, 6/5H), 1.96 (m, 2H), 1.40–1.65 (m, 7H), 0.90 (m, 9H), 0.00 (m, 6H).

Step D (4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(3-methyl-2-pyridinylmethyl)]-4-thiazolidinecarboxamide A mixture of the titled compound from Step C (0.74 g, 0.99 mmol) and tetrabutyl ammonium fluoride (1.98 mL, 1.98 mmol 1 M in THF) in THF (20 mL) was stirred at room temperature for 3 h. The solvent was removed. The titled compound was obtained as a white solid after flash column using EtOAc/hexane 9:1 as the elute. $^1$H NMR (CDCl$_3$, 400 MHz, 1:1 mixture of rotamers): 8.41 (m, 1/2H), 8.38 (m, 1/2H), 7.96 (m, 1H), 6.60–7.50 (m, 10H), 6.04 (m, 1/2H), 5.78 (m, 1/2H), 5.10 (m, 1/2H), 5.08 (m, 1/2H), 3.58–5.02 (m, 10H), 2.80–3.10 (m, 3H), 2.70 (m, 1/2H), 2.20 (m, 1/2H), 1.70 (s, 3H), 1.62 (s, 3H), 1.52 (m, 3H), 1.40 (m, 1H). LC-MS (M$^+$+1) (EI) 633.3.

EXAMPLE 21

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(3,5-dimethyl-4-isoxazolemethyl)]-4-thiazolidinecarboxamide

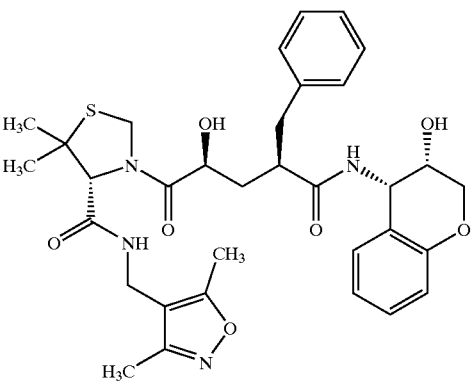

Step A 4-(Chloromethyl)-3,5-dimethylisoxazole (0.50 g, 3.4 mmol) was mixed with sodium azide (0.45 g, 6.87 mmol), and catalytic amount of sodium iodide in DMF (3 mL). The mixture was stirred at room temperature overnight. Water (10 mL) was added. The mixture was extracted with EtOAc (3×15 mL). The combined EtOAc layers were washed with brine (10 mL) and dried over sodium sulfate. Upon removal of the solvent, a colorless oil was obtained. The oil was mixed with 20 mL of 1:1 mixture of aqueous THF and triphenylphosphine (1.08 g, 4.1 mmol). The mixture was stirred at room temperature overnight. THF was removed. The mixture was then extracted with EtOAc (3×15 mL). The combined EtOAc layers were washed brine and dried over sodium sulfate. The titled compound was obtained as a colorless oil after flash column using methylene chloride/MeOH 95:5 as the elute. $^1$H NMR (CDCl$_3$, 400 MHz): 3.63 (s, 2H), 2.40 (s, 3H), 2.31 (s, 3H).

Step B

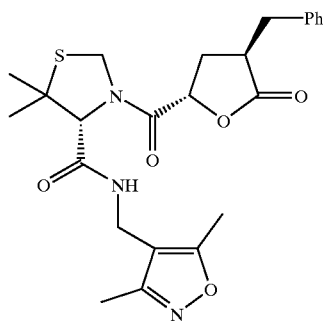

A mixture of the titled compound from Step A (0.026 g, 0.2 mmol), the titled compound from Example 19, Step E (0.063 g, 0.17 mmol), EDC (0.05 g, 0.26 mmol), HOAT (0.035 g, 0.26 mmol), and diisopropylethyl amine (0.06 mL, 0.34 mmol) in 5 mL of methylene chloride was stirred at room temperature overnight. The solvent was removed. The titled compound was obtained as a white solid using preparative TLC plate and EtOAc/hexane 1:1 as the elute. $^1$H NMR (CDCl$_3$, 400 MHz, 2:1 mixture of rotamers): 7.21 (m, 5H), 6.88 (br s, 2/3H), 6.00 (br s, 1/3H), 4.80 (m, 2H), 4.40 (s, 2/3H), 4.08 (m, 2H), 4.05 (s, 1/3H), 3.61 (m, 1H), 3.10 (m, 3H), 2.70 (m, 1H), 2.10–2.40 (m, 7H), 1.40 (m, 6H).

Step C

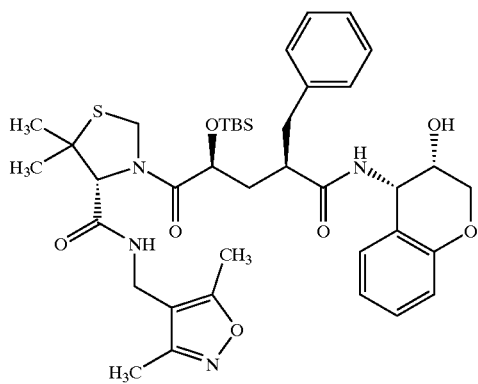

To a solution of the titled compound from Step B (0.032 g, 0.068 mmol) in dioxane (2 mL), 1M LiOH (0.081 mL, 0.081 mmol) was added. The solution was stirred at room temperature overnight. The solvent was removed and the trace of water was removed azatropically with toluene (3×2 mL). The residue was dried under high vacuum for 3 h. The resulting solid was then mixed with 20 mL of EtOAc, diisopropylethyl amine (0.095 mL, 0.54 mmol), and TBSOTf (0.063 mL, 0.27 mmol). The mixture was stirred at room temperature for 5 h until it became clear. LC/MS showed no starting material left. The solution was washed with water (5 mL), brine (5 mL), and dried over sodium sulfate. Upon removal of the solvent, the residue was mixed with 1:1 of water/THF (5 mL). The mixture was stirred at room temperature overnight. LC/MS showed that only the acid existed. The solvent was removed and dried under high vacuum. The resulting white solid was then mixed with cis-aminochromanol (0.017 g, 0.1 mmol), diisopropylethyl amine (0.059 mL, 0.34 mmol), O-benzotriazol-1-yl-N,N,N', N'-tetramethyluronium hexafluorophosphate (0.064 g, 0.17 mmol) and catalytic amount of HOAT in DMF (1 mL) was stirred at room temperature for 2 h. Water (5 mL) was added. The mixture was extracted with EtOAc (3×10 mL). The combined EtOAc layers were washed with brine (10 mL) and dried over sodium sulfate. The titled compound was obtained using preparative TLC plate and EtOAc/hexane 6:4 as the elute. $^1$H NMR (CDCl$_3$, 400 MHz, 1:1 mixture of rotamers): 6.80–7.40 (m, 9.5H), 5.92 (m, 1H), 5.78 (m, 1/2H), 5.16 (m, 1H), 4.74–4.98 (m, 3H), 3.82–4.40 (m, 8H), 2.80 (m, 3H), 2.30 (m, 7H), 1.89 (m, 1H), 1.50 (m, 6H), 0.97 (m, 9H), 0.02 (m, 6H).

Step D (4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(3,5-dimethyl-4-isoxazolemethyl)]-4-thiazolidinecarboxamide A mixture of the titled compound from Step C (0.013 g, 0.017 mmol) and tetrabutyl ammonium fluoride (0.034 mL, 0.034 mmol 1 M in THF) in THF (2 mL) was stirred at room temperature for 3 h. The solvent was removed. The titled compound was obtained as a white solid using preparative TLC plate and EtOAc/hexane 9:1 as the elute. $^1$H NMR (CDCl$_3$, 400 MHz, 1:1 mixture of rotamers): 6.79–7.40 (m, 9.5H), 5.92 (m, 1H), 5.82 (m, 0.5H), 5.20 (m, 0.5 H), 4.95 (m, 0.5H), 8.85 (m, 1H), 4.62 (m, 1H), 4.38 (s, 0.5H), 4.25 (m, 1.5H), 4.02 (m, 2H), 3.80 (m, 1H), 2.94 (m, 3H), 2.40 (s, 1.5H), 2.28 (s, 1.5H), 2.20 (s, 1.5H), 2.18 (s, 1.5H), 1.75 (m, 1H), 1.60 (s, 1.5H), 1.57 (s, 1.5H), 1.42 (s, 1.5H), 1.40 (s, 1.5H). LC-MS (M$^+$+1) (EI) 637.4.

EXAMPLE 22

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2,6-dimethylphenyl)methyl]-4-thiazolidinecarboxamide-1,1-dioxide

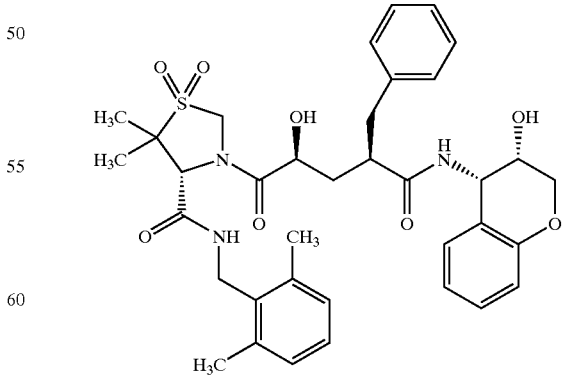

Step A

A mixture of the titled compound from Example 19, Step I (0.017 g, 0.026 mmol) and mCPBA (0.04 g, 0.13 mmol, 58%) in methylene chloride (2 mL) was stirred at room temperature for 4 h. 10 mL of methylene chloride were added. The solution was washed with saturated sodium bicarbonate (2 mL), brine, and dried over sodium sulfate. The titled compound was obtained as a white solid using preparative TLC plate and EtOAc/hexane 6:4 as the elute. $^1$H NMR (CDCl$_3$, 400 MHz, 1:1 mixture of rotamers): 6.75–7.40 (m, 12H), 6.08 (m, 0.5H), 5.97 (m, 0.5H), 5.80 (m, 0.5H), 5.08 (m, 1.5H), 4.20–4.80 (m, 3H), 4.00 (m, 2H), 3.70 (m, 1H), 3.00 (m, 1H), 2.80 (m, 1H), 2.40 (s, 4.5H), 2.20 (s, 1.5H), 2.02 (m, 1H), 1.48 (m, 6H). LC-MS (M$^+$+1) (EI) 678.4.

EXAMPLE 23

(4R)-N-[(2-chloro-6-methylphenyl)methyl]-3-[(2S, 4S)-5-[((3S,4S)-3,4-dihydro-3-hydroxy-2H-1-benzopyran-4-yl)amino]-4-(furo[2,3-c]pyridin-2-ylmethyl)-2-hydroxy-1,5-dioxopentyl]-5,5-dimethyl-4-thiazolidinecarboxamide

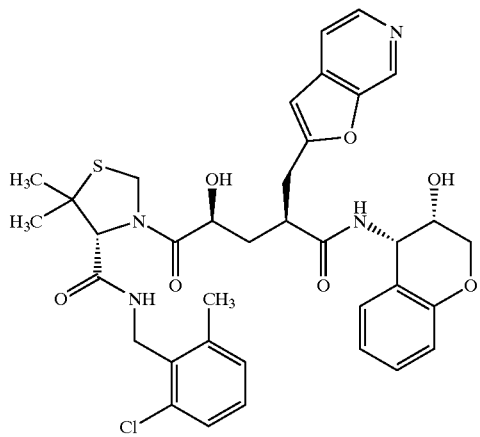

Step A:

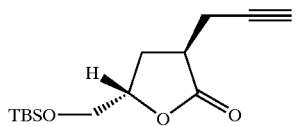

LDA was formed by adding n-butyl lithium (3.47 mL; 8.68 mmol) to a solution of diisopropyl amine (1.25 mL; 9.55 mmol) in 28 mL of anhydrous THF cooled to 0° C. under nitrogen. After 15 minutes the solution was cooled to −78° C. and a solution of dihydro-5-(S)-[[(tert-butyldiphenylsilyl)oxy]methyl]-3-(2H)-furanone (2.0 g; 8.68 mmol) in 8 mL of anhydrous THF was added dropwise. After 30 minutes propargyl bromide (1.55 g; 10.4 mmol) was added dropwise and the reaction was stirred 1.5 hours. The contents of the reaction vessel were then poured into diethyl ether (400 mL) and washed with water and brine. Drying (MgSO$_4$), filtration and removal of the solvent in vacuo provided the crude product which was purified by flash chromatography (8% EtOAc/hexane) to provide 1.27 g of desired compound (55% yield).

Step B:

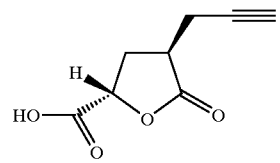

To the compound derived from Step A above (645 mg; 2.40 mmol) in anhydrous THF (15 mL) in a teflon flask was added HF•pyridine solution (1 mL). After 48 hours the reaction vessel was cooled to 0° C. and quenched with NH$_4$OH/H$_2$O (2:1) to pH=9–10. The solvent was removed in vacuo and the residue dissolved in EtOAc followed by washing with water and brine. After drying (MgSO$_4$), filtration and removal of the solvent in vacuo, purification employing flash chromatography (50% EtOAc/hex) provided a quantitative yield of the desired alcohol. To the entire amount of the alcohol (2.4 mmol) dissolved in 25 mL of acetone was added 1.25 mL of Jones reagent. After stirring overnight, the reaction was quenched by the addition of EtOH. Filtration of the reaction through celite was followed by dilution with water and concentration in vacuo. The residual aqueous layer was extracted with EtOAc (3×). Drying (MgSO$_4$), filtration and removal of the solvent in vacuo provided 370 mg (34%) of the desired carboxylic acid which was used without further purification.

Step C:

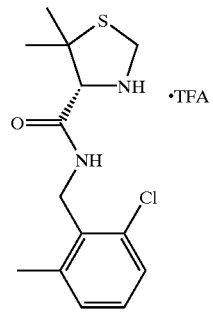

To a solution of carboxylic acid derived in Example 1 Step B (3.76 g; 14.3 mmol) in anhydrous NMP at 0° C. was added DIEA (7.5 mL; 42.9 mmol) followed by HBTU (8.13 g; 21.45 mmol). After 15 minutes, 2-chloro-6-methylbenzylamine (2.67 g; 17.1 mmol) was added. The next day, the contents of the reaction mixture were poured into EtOAc, washed with water, 1N HCl, water, and brine. Drying (MgSO$_4$), filtration, and removal of solvents in vacuo was followed by Biotage column chromatography (25% EtOAc/hexane) to provide the Boc derivative which was dissolved in DCM, cooled to 0° C., and TFA added.

After 4 hours the solvents were removed in vacuo and the residue azeotroped twice from DCM to provide the desired amine.

Step D:

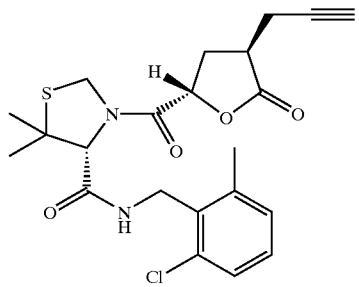

To a stirred solution of the acid from Step B (370 mg; 2.2 mmol) and the amine from Step C (550 mg; 1.84 mmol) in anhydrous DCM (12 mL) and anhydrous DMF (1 mL) cooled to 0° C. was added DIEA (0.770 mL; 4.42 mmol). The following solids were then added, waiting until complete dissolution occurred before adding the next: HOAt (299 mg; 2.2 mmol); and PyBop (1.14 g; 2.2 mmol). The ice bath was removed and the reaction was allowed to stir overnight. The DCM was then removed in vacuo, the residue poured into EtOAc and washed with NaHCO$_3$ solution, H$_2$O and brine. Drying (MgSO$_4$), filtration and removal of the solvent in vacuo followed by purification employing Biotage flash chromatography (40% EtOAc/hex) provided 565 mg (68% yield) of the desired product.

Step E:

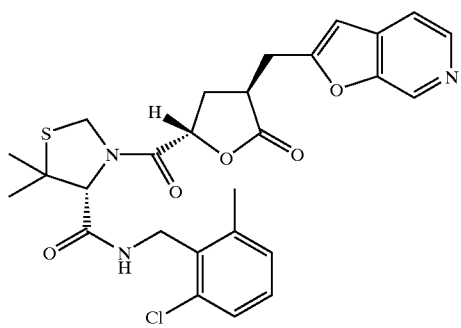

To a stirred solution of terminal acetylene (56 mg; 0.125 mmol) from Step D above and 4-iodo-3-pyridinol (41 mg; 0.019 mmol) in 1.5 mL of anhydrous pyridine under nitrogen was added Cu$_2$O (27 mg; 0.19 mmol). The reaction was heated to 120–125° C. for 40 minutes. The reaction was allowed to cool, filtered through celite, diluted with EtOAc and washed with water, NaHCO$_3$ solution and brine. Drying (MgSO$_4$), filtration and removal of the solvent in vacuo (azeotrope 1× from hexane) followed by purification employing flash chromatography (100% EtOAc) provided 36 mg of the desired compound (57% yield) after lyophilization from MeCN/water.

Step F:

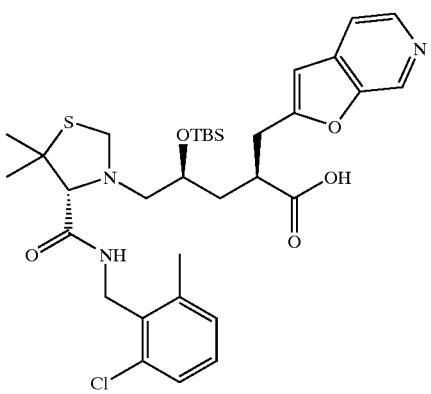

To a solution of the lactone from Step E (35 mg; 0.065 mmol) in anhydrous DME (1 mL) cooled to 0° C. was added an aqueous solution of LiOH (0.072 mL; 0.072 mmol). An additional 0.010 mL of LiOH was added after 1 hour. The reaction was stirred 30 minutes. The solvents were removed in vacuo at no greater than 35° C. and the residue azeotroped from benzene and MeCN until a foam was obtained. This solid was dissolved in dry DMF (1 mL). Imidazole was added (89 mg; 1.3 mmol), and the resulting solution cooled to 0° C. TBDMSCl (98 mg; 0.65 mmol) was then added, the ice bath removed and the mixture allowed to stir at ambient temperature overnight. The reaction was quenched with pH=7 buffer and extracted with EtOAc (2×20 mL). Drying (MgSO$_4$), filtration and removal of the solvent in vacuo provided a mixture of mono- and bis-protected intermediate. This ester/acid mixture was dissolved in THF (0.5 mL)/H$_2$O (0.25 mL) and stirred 2 hours. Solvents were removed in vacuo and the residue azeotroped from toluene and MeCN and finally from diethyl ether to provide the crude acid which was used without further purification.

Step G:

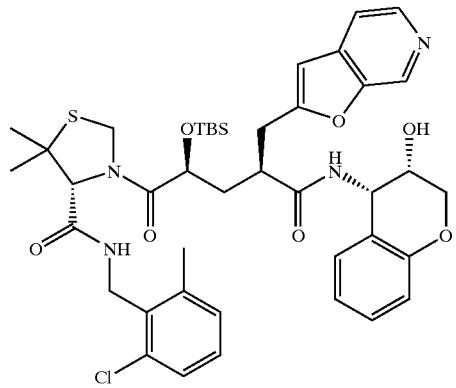

The crude product from Step F above was dissolved in anhydrous NMP (1.1 mL) cooled to 0° C. and DIEA (0.034 mL; 0.195 mmol) was added. The following solids were then added sequentially, waiting until complete dissolution of solid occurred before adding the next: HOBt (20 mg; 0.146 mmol); cis-aminochromanol, prepared as in Example 1 Step L, (13 mg; 0.078 mmol); and HBTU (37 mg; 0.098 mmol).

The solution was allowed to stir at ambient temperature overnight. The reaction was poured into 25 mL EtOAc, washed with dilute NaHCO₃ solution, H₂O and brine. Drying (MgSO₄), filtration and removal of the solvent in vacuo followed by purification employing flash chromatography (2% MeOH/EtOAc) provided 43 mg of the desired product.

Step H:

(4R)-N-[(2-chloro-6-methylphenyl)methyl]-3-[(2S,4S)-5-[((3S,4S)-3,4-dihydro-3-hydroxy-2H-1-benzopyran-4-yl)amino]-4-(furo[2,3-c]pyridin-2-ylmethyl)-2-hydroxy-1,5-dioxopentyl]-5,5-dimethyl-4-thiazolidinecarboxamide The intermediate from Step G above (43 mg; 0.052 mmol) was dissolved in anhydrous THF (0.4 mL) under nitrogen and TBAF (0.130 mL; 0.13 mmol) was added. The solution was heated to 55–60° C. After 1 hour, the reaction was poured into EtOAc (30 mL) and washed alternately with dilute NaHCO₃, H₂O and brine. Drying (MgSO₄), filtration, and removal of solvent in vacuo was followed by column chromatography (5% MeOH/DCM) and then by reverse phase MPLC chromatography (MeCN/water gradient 10:90 to 90:10 over 30 minutes; LiChroprep 100 RP-18 40–63 μm particle size) to provide 10 mg of the final product as a white solid. Electrospray ionization mass spectrum: m/e 707.1 (MH⁺ calcd for $C_{36}H_{40}ClN_4O_7S$, 707.23).

EXAMPLE 24

(4R)-N-[(2-chloro-6-methylphenyl)methyl]-3-[(2S,4S)-5-[((3S,4S)-3,4-dihydro-3-hydroxy-2H-1-benzopyran-4-yl)amino]-2-hydroxy-4-(5-oxazolylmethyl)-1,5-dioxopentyl]-5,5-dimethyl-4-thiazolidinecarboxamide

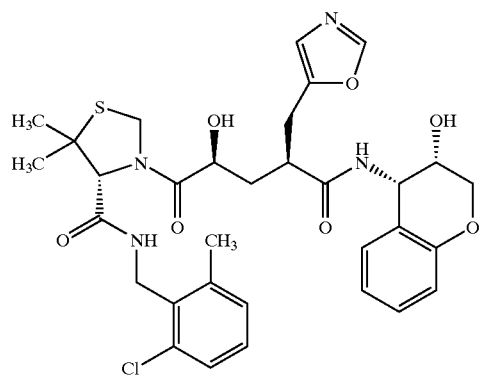

Step A:

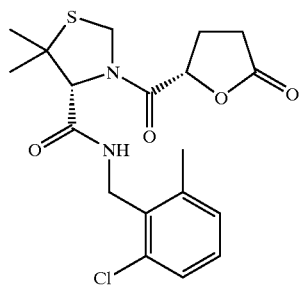

(S)-(+)-5-oxo-2-tetrahydrofurancarboxylic acid (290 mg; 2.2 mmol) was suspended in anhydrous DCM (10 mL) and the TFA salt of amine from Example 23 Step C (769 mg; 1.86 mmol) was added; dissolution occurred. The solution was cooled to 0° C., and DIEA (1.3 mL; 7.44 mmol) added followed by HOAt (229 mg; 2.2 mmol) and then PyBop (1.14 g; 2.2 mmol). The next morning, the reaction mixture was poured into ethyl acetate and washed with water and brine. Drying (MgSO₄), filtration and removal of the solvent in vacuo followed by flash column chromatography (75% EtOAc/hexane) provided the desired compound.

Step B:

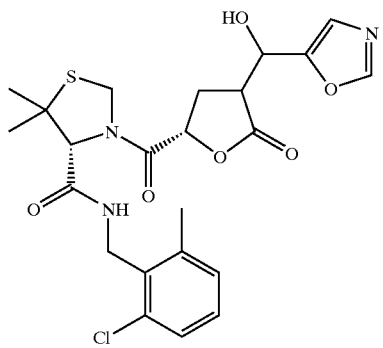

To a solution of the intermediate obtained in Step A above (150 mg; 0.37 mmol) in 2.5 mL anhydrous THF at −78° C. under nitrogen was added dropwise LHMDS (0.77 mmol; 0.77 mL). After 1 hr 20 min, a solution of 5-oxazolecarboxaldehyde (39 mg; 0.40 mmol) in 0.5 mL anhydrous THF was added dropwise. After 1.25 hr, the reaction was quenched with saturated ammonium chloride. The mixture was poured into EtOAc and washed with 50% brine and brine. Drying (MgSO₄), filtration, and removal of the solvent in vacuo followed by flash column chromatography (gradient elution 75% EtOAc/hexane to 100% EtOAc) provided the desired compound.

Step C:

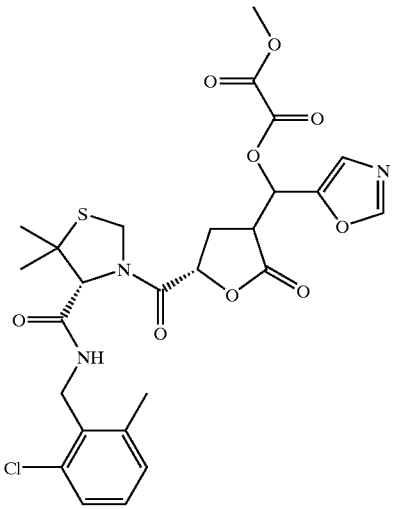

To a solution of the material from Step B (67 mg; 0.13 mmol) in 0.75 mL anhydrous THF cooled to 0° C. was added TEA (20 μL; 0.143 mmol) and 4-pyrrolidinopyridine (cat.); methyl oxalyl chloride (13 μL; 0.143 mmol) was then added dropwise. After 2.25 hours, the reaction mixture was diluted with EtOAc (40 mL) and washed with NaHCO₃ solution and brine. Drying (MgSO₄), filtration, and removal of the solvent in vacuo followed by flash column chromatography (75% EtOAc/hexane) provided the desired compound.

Step D:

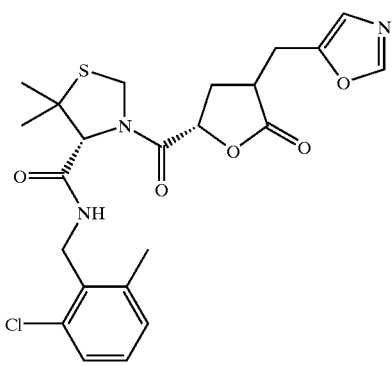

To a solution of the intermediate from Step C (50 mg; 0.084 mmol) in anhydrous toluene (1.0 mL) was added AIBN (cat.) followed by Ph$_3$SnH (43 μL; 0.168 mmol). Twenty minutes at reflux was followed by 1.5 hours at 100° C. Removal of solvent in vacuo was followed by flash column chromatography (75% EtOAc/hexane) to provide the desired compound.

Step E:

(4R)-N-[(2-chloro-6-methylphenyl)methyl]-3-[(2S,4S)-5-[((3S,4S)-3,4-dihydro-3-hydroxy-2H-1-benzopyran-4-yl)amino]-2-hydroxy-4-(5-oxazolylmethyl)-1,5-dioxopentyl]-5,5-dimethyl-4-thiazolidinecarboxamide The intermediate from Step D was carried forward in the same manner as Example 23, Steps F, G, and H. Final purification by reverse phase MPLC chromatography (MeCN/water gradient 10:90 to 90:10 over 30 minutes; LiChroprep 100 RP-18 40–63 μm particle size) provided the title compound as a white solid. Electrospray ionization mass spectrum: m/e 657.2 (MH$^+$ calcd for C$_{32}$H$_{37}$ClN$_4$O$_7$S, 657.21).

EXAMPLE 25

Preparation of Enzymes

Synthetic oligonucleotide cassettes of 444 base pairs were designed according to the wild-type sequence of pET-3b-HIVPR. Point mutations were incorporated into the DNA with a bias toward optimal codon usage in *E. coli* to yield amino acid mutations listed in Table 2 below. The oligonucleotides were annealed and ligated into pUC-18 or pUC-19 by Midland Certified Reagent Company. The primary sequence was verified before subcloning into a pET-3b expression vector via Nde I and Bpu1102 I sites and reconfirmed by automated double-stranded DNA sequencing. Clones carrying the mutant DNA were transformed and expressed as previously described in Schock et al., *J. Biol. Chem.* 1996, 271: 31957–31963 and Chen et al., *J. Biol. Chem.* 1995, 270:: 21433–21436. The cells were lysed in 50 mM Tris-HCl pH 8.0, 1 mM EDTA, 0.1% NP40, 10 mM MgCl$_2$, and 100 μg/mL DNase I using a microfluidizer processor (Microfluidics International Corp., Newton, Mass.). The mutant protease was extracted, refolded, and purified over affinity columns as previously described in Schock et al., *J. Biol. Chem.* 1991, 271: 31957–31963. Protein concentrations were determined by amino acid analysis and purity was confirmed by SDS gel electrophoresis.

EXAMPLE 26

Assay for Inhibition of Microbial Expressed HIV Protease

Inhibition studies of the reaction of the protease (which was expressed in *Eschericia coli*) with a peptide substrate [Val-Ser-Gln-Asn-(betanapthyl) Ala-Pro-Ile-Val, 0.5 mg/mL at the time the reaction is initiated] were in 50 mM Na acetate, pH 5.5, 0.1% bovine serum albumin, 3.75% DMSO at 30° C. for 1 hour. Various concentrations of inhibitor in 2 mL DMSO were added to 50 μL of the peptide solution in buffer. The reaction is initiated by the addition of 28 μL of 14.3 pM (wild type, K-60, Q-60) and 28.6 pM (V-18) protease in a solution of 50 mM Na acetate pH 5.5 and 0.1% bovine serum albumin. The reaction was quenched with 120 μL of 10% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. The compounds of the invention prepared in Examples 1–24 exhibited IC$_{50}$ values ranging from about 0.05 to about 1 nM against the wild-type enzyme. The indinavir IC$_{50}$ value against the wild type enzyme is 0.6 nM (average). The compounds of the invention prepared in Examples 1–24 exhibited IC$_{50}$ values in the range of 0.2 to 5 nM against the mutant enzymes Q-60, K-60, and V-18. These IC$_{50}$ values range from 4-fold to greater than 100-fold more potent than indinavir's values of 20 to 50 nM against these same mutant enzymes.

TABLE 2

| | Wild-type and Mutant HIV-1 Protease Sequences | | | | | | | | | | | | | | | | | | |
|---|---|---|---|---|---|---|---|---|---|---|---|---|---|---|---|---|---|---|---|
| Wild-type | L10 | K20 | L24 | M36 | S37 | R41 | M46 | I54 | R57 | Q58 | I62 | L63 | I64 | A71 | G73 | V77 | V82 | I84 | L90 | I93 |
| Q-60 | I | | | | | K | I | V | | | V | P | | V | | | I | A | M | L |
| K-60 | I | | | | | | I | V | | E | | P | V | | | | I | F | M | L |
| V-18 | I | | I | D | | | I | | K | | | P | | V | S | | | V | M | L |

See Condra et al., *J. Virol* 1996, 70: 8270–8276 and Olsen et al., *J. Biol. Chem.* 1999, in press, for further details.

EXAMPLE 27

Preparation of Viral Constructs

Mutant viruses were constructed using gapped-duplex oligonucleotide mutagenesis of a subclone of plasmid pWT-6 as described in Colonno et al., *Proc. Nat'l Acad. Sci.* 1988, 85: 5449–5453. Infectious mutant proviral clones were constructed by subcloning the 833-b.p. ApaI-Sse83871 fragment containing the mutagentized protease gene into the corresponding sites of plasmid pNL4-3 (see *J. Virol.* 1986, 59: 284–291). After transfection of the mutant proviral clone into HeLa cells and growth of viral stocks in cocultivated H9 human T-lymphoid cells, the complete sequence of the viral protease gene from the mutant viral population was verified as described in *Nature* 1995, 374: 569–571. The amino acid changes from wild type sequence for three of these viral constructs are shown in Table 2.

EXAMPLE 28

Cell Spread Assay

Inhibition of the spread of HIV in cell culture was measured according to Nunberg et al., *J. Virol.* 1991, 65: 4887. In this assay, MT-4 T-lymphoid cells were infected with HIV-1 (wild-type, unless otherwise indicated) by using a predetermined inoculum, and cultures were incubated for 24 h. At this time, ≦1% of the cells were positive by indirect immunofluorescence. Cells were then extensively washed and distributed into 96-well culture dishes. Serial twofold dilutions of inhibitor were added to the wells, and cultures were continued for 3 additional days. At 4 days postinfection, 100% of the cells in control cultures were infected. HIV-1 p24 accumulation was directly correlated with virus spread. The cell culture inhibitory concentration was defined as the inhibitor concentration in nanomoles/liter which reduced the spread of infection by at least 95%, or $CIC_{95}$. The compounds of the invention prepared in Examples 1–24 exhibited $CIC_{95}$ values in the range of from about 8 to about 50 nM against the wild-type viral construct. The $CIC_{95}$ of indinavir against the wild-type viral construct is from 50 to 100 nM. The compounds of the invention prepared in Examples 1–24 exhibited $CIC_{95}$ values in the range of about 8 to about 125 nM against the viral constructs Q60, K-60, and V-18. These $CIC_{95}$ values range from about 8-fold to more than about 35-fold more potent than indinavir's values of greater than 1000 nM against these same viral constructs.

EXAMPLE 29

Inhibition of Virus Spread

A. Preparation of HIV-infected MT-4 Cell Suspension

MT cells were infected at Day 0 at a concentration of 250,000 per ml with a 1:1000 dilution of HIV-1 strain IIIb stock (final 125 pg p24/ml; sufficient to yield ≦1% infected cells on day 1 and 25–100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C. in 5% $CO_2$ atmosphere.

B. Treatment with Inhibitors

A matrix of nanomolar range concentrations of the pairwise combinations is prepared. At Day 1, aliquots of 125 ml of inhibitors are added to equal volumes of HIV-infected MT-4 cells (50,000 per well) in a 96-well microtiter cell culture plate. Incubation is continued for 3 days at 37° C. in 5% $CO_2$ atmosphere.

C. Measurement of Virus Spread

Using a multichannel pipettor, the settled cells are resuspended and 125 ml harvested into a separate microtiter plate. The supernatant is assayed for HIV p24 antigen.

The concentration of HIV p24 antigen is measured by an enzyme immunoassay, described as follows. Aliquots of p24 antigen to be measured are added to microwells coated with a monoclonal antibody specific for HIV core antigen. The microwells are washed at this point, and at other appropriate steps that follow. Biotinylated HIV-specific antibody is then added, followed by conjugated streptavidin-horseradish peroxidase. A color reaction occurs from the added hydrogen peroxide and tetramethylbenzidine substrate. Color intensity is proportional to the concentration of HIV p24 antigen.

Calculation of Degree of Synergy

When there is synergy, pairwise combinations of inhibitors are found to exhibit markedly enhanced inhibition of virus spread, in comparison to each inhibitor alone, or in comparison to merely additive inhibition of each inhibitor.

The data is processed as follows: fractional inhibitory concentration ratios (FIC) are calculated according to Elion, et al., *J. Biol. Chem.* 1954, 208: 477. The minimum sum of FICs, which is the maximum synergy, is determined for various pairwise combinations. The smaller the number, the greater the synergy.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of formula:

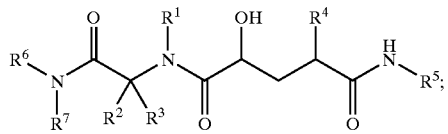

wherein
$R^1$, $R^2$, and $R^3$ are defined in (A) or in (B) as follows:
(A) $R^1$ is
1) hydrogen
2) $C_1$–$C_6$ alkyl, or
3) substituted $C_1$–$C_6$ alkyl wherein each substituent is independently selected from
   a) halo,
   b) hydroxy,
   c) $C_1$–$C_3$ alkoxy,
   d) aryl,
   e) substituted aryl, wherein each substituent is independently selected from halo, hydroxy, $C_1$–$C_4$ alkyl, fluorinated $C_1$–$C_4$ alkyl, and aryl,
   f) heterocycle, and
   g) substituted heterocycle, wherein each substituent is independently selected from halo, hydroxy, $C_1$–$C_4$ alkyl, fluorinated $C_1$–$C_4$ alkyl, and aryl;
$R^2$ and $R_3$ are each independently selected from
1) hydrogen,
2) $C_1$–$C_6$ alkyl,
3) substituted $C_1$–$C_6$ alkyl wherein each substituent is independently selected from
   a) halo,
   b) hydroxy,
   c) $C_1$–$C_3$ alkoxy,
   d) aryl,
   e) substituted aryl, wherein each substituent is independently selected from cyano, halo, hydroxy, $C_1$–$C_4$ alkyl, fluorinated $C_1$–$C_4$ alkyl, and aryl,
   f) heterocycle, and
   g) substituted heterocycle, wherein each substituent is independently selected from cyano, halo, hydroxy, $C_1$–$C_4$ alkyl, fluorinated $C_1$–$C_4$ alkyl, and aryl,
4) aryl,
5) substituted aryl wherein each substituent is independently selected from
   a) halo,
   b) hydroxy,
   c) $C_1$–$C_3$ alkoxy,
   d) aryl,
   e) substituted aryl wherein each substituent is independently selected from cyano, halo, hydroxy, $C_1$–$C_4$ alkyl, and fluorinated $C_1$–$C_4$ alkyl, f) heterocycle,
g) substituted heterocycle wherein each substituent is independently selected from cyano, halo, hydroxy, $C_1$–$C_4$ alkyl, and fluorinated $C_1$–$C_4$ alkyl,
6) heterocycle, and
7) substituted heterocycle wherein each substituent is independently selected from
   a) halo,
   b) hydroxy,
   c) $C_1$–$C_3$ alkoxy,
   d) aryl,
   e) substituted aryl wherein each substituent is independently selected from cyano, halo, hydroxy, $C_1$–$C_4$ alkyl, and fluorinated $C_1$–$C_4$ alkyl,
   f) heterocycle, and
   g) substituted heterocycle wherein each substituent is independently selected from cyano, halo, hydroxy, $C_1$–$C_4$ alkyl, and fluorinated $C_1$–$C_4$ alkyl;

or $R^2$ and $R^3$ together with the carbon to which they are attached from $C_3$–$C_6$ cycloalkyl which is optionally substituted with one or more substituents independently selected from
1) hydroxy
2) $C_1$–$C_6$ alkyl,
3) $C_1$–$C_3$ alkoxy,
4) aryl,
5) substituted aryl wherein each substituent is independently selected from
   a) halo,
   b) hydroxy,
   c) $C_1$–$C_3$ alkoxy,
   d) $C_1$–$C_4$ alkyl,
   e) fluorinated $C_1$–$C_4$ alkyl,
   f) aryl,
   g) substituted aryl wherein each substituent is independently selected from halo, hydroxy, $C_1$–$C_4$ alkyl, and fluorinated $C_1$–$C_4$ alkyl,
   h) heterocycle,
   i) substituted heterocycle wherein each substituent is independently selected from halo, hydroxy, $C_1$–$C_4$ alkyl, and fluorinated $C_1$–$C_4$ alkyl,
6) heterocycle, and
7) substituted heterocycle wherein each substituent is independently selected from
   a) halo,
   b) hydroxy,
   c) $C_1$–$C_3$ alkoxy,
   d) $C_1$–$C_4$ alkyl,
   e) fluorinated $C_1$–$C_4$ alkyl,
   f) aryl,
   g) substituted aryl wherein each substituent is independently selected from halo, hydroxy, $C_1$–$C_4$ alkyl, and fluorinated $C_1$–$C_4$ alkyl,
   h) heterocycle, and
   i) substituted heterocycle wherein each substituent is independently selected from halo, hydroxy, $C_1$–$C_4$ alkyl, and fluorinated $C_1$–$C_4$ alkyl
or
(B) $R_1$ and $R^2$ together with the nitrogen to which $R^1$ is attached and the carbon to which $R^2$ is attached to a 4- to 8-membered monocyclic heterocycle containing from 1 to 3 heteroatoms selected from nitrogen, oxygen, and sulfur, wherein at least one heteroatom in the monocyclic heterocycle is nitrogen and wherein the monocyclic heterocycle is optionally substituted with one or more substituents independently selected from 1) halo
2) hydroxy
3) $C_1$–$C_6$ alkyl,
4) $C_1$–$C_3$ alkoxy,
5) aryl, and
6) heterocycle;

and $R^3$ is as defined in (A) when $R^3$ is independent from and not joined to $R^2$;

$R^4$ is $(CH_2)_m R^a$, wherein m is an integer from zero to 3 and $R^a$ is
1) hydrogen,
2) $C_1$–$C_6$ alkyl,
3) substituted $C_1$–$C_6$ alkyl wherein each substituent is independently selected from
   a) halo,
   b) hydroxy, and
   c) $C_1$–$C_3$ alkoxy,
4) aryl,
5) substituted aryl wherein each substituent is independently selected from
   a) halo,
   b) hydroxy,
   c) $C_1$–$C_3$ alkoxy,
   d) $C_1$–$C_4$ alkyl,
   e) fluorinated $C_1$–$C_4$ alkyl,
   f) aryl,
   g) substituted aryl wherein each substituent is independently selected from halo, hydroxy, $C_1$–$C_4$ alkyl, and fluorinated $C_1$–$C_4$ alkyl,
   h) heterocycle, and
   i) substituted heterocycle wherein each substituent is independently selected from halo, hydroxy, $C_1$–$C_4$ alkyl, and fluorinated $C_1$–$C_4$ alkyl,
6) heterocycle, or
7) substituted heterocycle wherein each substituent is independently selected from
   a) halo,
   b) hydroxy,
   c) $C_1$–$C_3$ alkoxy,
   d) $C_1$–$C_4$ alkyl,
   e) fluorinated $C_1$–$C_4$ alkyl,
   f) aryl,
   g) substituted aryl wherein each substituent is independently selected from halo, hydroxy, $C_1$–$C_4$ alkyl, and fluorinated $C_1$–$C_4$ alkyl,
   h) heterocycle, and
   i) substituted heterocycle wherein each substituent is independently selected from halo, hydroxy, $C_1$–$C_4$ alkyl, and fluorinated $C_1$–$C_4$ alkyl;

$R^5$ is chroman, thiochroman, indanyl, dioxoisothiochroman, cyclopentyl, substituted chroman, substituted thiochroman, substituted indanyl, substituted dioxothiochroman, or substituted cyclopentyl; wherein each of the substituents on substituted chroman, thiochroman, indanyl, dioxoisothiochroman, or cyclopentyl is independently selected from halogen, cyano, hydroxy, $C_1$–$C_6$ alkyl, fluorinated $C_1$–$C_6$ alkyl, $C_1$–$C_4$ alkoxy, or fluorinated $C_1$–$C_4$ alkoxy; and $R^6$ and $R^7$ are each independently
1) hydrogen,
2) $C_1$–$C_6$ alkyl, or
3) substituted $C_1$–$C_6$ alkyl wherein each substituent is independently selected from a) halo,
b) hydroxy,
c) aryl,
d) substituted aryl, wherein each substituent is independently selected from halo, hydroxy, $C_1$–$C_4$ alkyl, fluorinated $C_1$–$C_4$ alkyl, and aryl,
e) heterocycle, and
f) substituted heterocycle wherein each substituent is independently selected from halo, hydroxy, $C_1$–$C_4$ alkyl, fluorinated $C_1$–$C_4$ alkyl, and aryl, or $R^6$ and $R^7$ together with the nitrogen to which they are attached from $C_3$–$C_6$ azacycloalkyl which is optionally substituted with one or more substituents independently selected from
1) halo,
2) hydroxy,
3) $C_1$–$C_6$ alkyl,
4) $C_1$–$C_3$ alkoxy,
5) aryl,
6) substituted aryl wherein each substituent is independently selected from
   a) halo,
   b) hydroxy,
   c) $C_1$–$C_3$ alkoxy,
   d) $C_1$–$C_4$ alkyl, and
   e) fluorinated $C_1$–$C_4$ alkyl
7) heterocycle, and
8) substituted heterocycle wherein each substituent is independently selected from
   a) halo,
   b) hydroxy,
   c) $C_1$–$C_3$ alkoxy,
   d) $C_1$–$C_4$ alkyl, and
   e) fluorinated $C_1$–$C_4$ alkyl;
or pharmaceutically acceptable salt thereof.

2. The compound according to claim 1, wherein $R^1$, $R^2$, and $R^3$ are as defined in (A);
or a pharmaceutically acceptable salt thereof.

3. The compound according to claim 2, wherein
$R^1$ is hydrogen or $C_1$–$C_4$ alkyl;
$R^2$ and $R^3$ are each independently selected from hydrogen or $C_1$–$C_4$ alkyl; or $R^2$ and $R^3$ together with the carbon to which they are attached from $C_3$–$C_6$ cycloalkyl;
$R^4$ is $(CH_2)_m R^a$, wherein m is an integer from zero to 3 and $R^a$ is
1) hydrogen,
2) $C_1$–$C_4$ alkyl,
3) substituted $C_1$–$C_4$ alkyl wherein each substituent is independently selected from
   a) halo
   b) hydroxy, and
   c) $C_1$–$C_3$ alkoxy,
4) phenyl,
5) mono- or di- or tri-substituted phenyl wherein each substituent is independently selected from
   a) halo,
   b) hydroxy,
   c) $C_1$–$C_3$ alkoxy,
   d) $C_1$–$C_4$ alkyl,
   e) $(CH_2)_{0-3}CF_3$,
   f) phenyl,
   g) mono- or di- or tri-substituted phenyl, wherein each substituent is independently selected from halo, hydroxy, $C_1$–$C_4$ alkyl, and $(CH_2)_{0-3}CF_3$,
   h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and
   i) mono- or di- or tri-substituted heterocycle, wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, pyrazolyl, triazolyl, and tetrazolyl, and wherein each substituent is independently selected from halo, hydroxy, $C_1$–$C_4$ alkyl, and $(CH_2)_{0-3}CF_3$;
6) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, tetrazolyl, and furopyridyl, or
7) mono- or di or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, tetrazolyl, and furopyridyl, and wherein each substituent is independently selected from
   a) halo,
   b) hydroxy,
   c) $C_1$–$C_3$ alkoxy,
   d) $C_1$–$C_4$ alkyl,
   e) $(CH_2)_{0-3}CF_3$,
   f) phenyl,
   g) mono- or di or tri-substituted phenyl wherein each substituent is independently selected from halo, hydroxy, $C_1$–$C_4$ alkyl, and $(CH_2)_{0-3}CF_3$,
   h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and
   i) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and wherein each substituent is independently selected from halo, hydroxy, $C_1$–$C_4$ alkyl, and $(CH_2)_{0-3}CF_3$;

$R^5$ is chroman, thiochroman, indanyl, dioxoisothiochroman, cyclopentyl, substituted chroman, substituted thiochroman, substituted indanyl, substituted dioxothiochroman, or substituted cyclopentyl; wherein each of the substituents on substituted chroman, thiochroman, indanyl, dioxoisothiochroman, or cyclopentyl is independently selected from halogen, cyano, hydroxy, $C_1$–$C_4$ alkyl, $(CH_2)_{0-3}CF_3$, $C_1$–$C_4$ alkoxy, or $(CH_2)_{0-3}OCF_3$; and $R_6$ and $R^7$ are each independently
1) hydrogen,
2) $C_1$–$C_4$ alkyl, or
3) substituted $C_1$–$C_4$ alkyl wherein each substituent is independently selected from
   a) halo
   b) hydroxy,
   c) phenyl,
   d) mono- or di- or tri-substituted phenyl, wherein each substituent is independently selected from halo, hydroxy, $C_1$–$C_4$ alkyl, $(CH_2)_{0-3}CF_3$, and phenyl, e) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and f) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and wherein each substituent is independently selected from halo, hydroxy, $C_1$–$C_4$ alkyl, $(CH_2)_{0-3}CF_3$, and phenyl;

or $R^6$ and $R^7$ together with the nitrogen to which they are attached form $C_3$–$C_6$ azacycloalkyl which is optionally substituted with one or more substituents independently selected from 1) halo
2) hydroxy
3) $C_1$–$C_4$ alkyl, and
4) $C_1$–$C_3$ alkoxy;

or pharmaceutically acceptable salt thereof.

4. The compound according to claim 3, wherein $R^5$ is chroman, indanyl, substituted chroman, or substituted indanyl;

or a pharmaceutically acceptable salt thereof.

5. The compound according to claim 4, wherein $R^a$ is

1) $C_1$–$C_4$,
2) substituted $C_1$–$C_4$ alkyl wherein each substituent is independently selected from
   a) halo,
   b) hydroxy, and
   c) $C_1$–$C_3$ alkoxy,
3) phenyl,
4) mono- or di- or tri-substituted phenyl wherein each substituent is independently selected from
   a) halo
   b) hydroxy,
   c) $C_1$–$C_3$ alkoxy,
   d) $C_1$–$C_4$ alkyl,
   e) $CF_3$,
   f) phenyl,
   g) mono- or di- or tri-substituted phenyl, wherein each substituent is independently selected from halo, hydroxy, $C_1$–$C_4$ alkyl, and $CF_3$,
   h) heterocycle selected from pyridyl, pyrazinyl and pyrimidinyl, and
   i) mono- or di- or tri-substituted heterocycle, wherein heterocycle is selected from pyridyl, pyrazinyl, and pyrimidinyl, and wherein each substituent is independently selected from halo, hydroxy, $C_1$–$C_4$ alkyl, and $CF_3$;
5) heterocycle selected from pyridyl, pyrazinyl and pyrimidinyl, or
6) mono- or di- or tri-substituted heterocycle wherein heterocycle is selected from pyridyl, pyrazinyl and pyrimidinyl; and wherein each substituent is independently selected from
   a) halo,
   b) hydroxy,
   c) $C_1$–$C_3$ alkoxy,
   d) $C_1$–$C_4$ alkyl,
   e) $CF_3$,
   f) phenyl,
   g) mono- or di- or tri-substituted phenyl wherein each substituent is independently selected from cyano, halo, hydroxy, $C_1$–$C_4$ alkyl, and $CF_3$,
   h) heterocycle selected from pyridyl, pyrazinyl and pyrimidinyl, and
   i) mono- or di- or tri-substituted heterocycle wherein heterocycle is selected from pyridyl, pyrazinyl and pyrimidinyl, and wherein each substituent is independently selected from cyano, halo, hydroxy, $C_1$–$C_4$ alkyl, and $CF_3$; and $R_6$ and $R_7$ are each independently 1) hydrogen,
2) $C_1$–$C_4$ alkyl, or
3) substituted $C_1$–$C_4$ alkyl wherein each substituent is independently selected from
   a) halo,
   b) hydroxy,
   c) phenyl,
   d) mono- or di- or tri-substituted phenyl, wherein each substituent is independently selected from halo, hydroxy, $C_1$–$C_4$ alkyl, and $CF_3$,
   e) heterocycle selected from pyridyl, pyrazinyl and pyrimidinyl, and
   f) mono- or di- or tri-substituted heterocycle wherein heterocycle is selected from pyridyl, pyrazinyl and pyrimidinyl, and wherein each subsequent is independently selected from halo, hydroxy, $C_1$–$C_4$ alkyl, and $(CH_2)_{0-3}$ $CF_3$;

or pharmaceutically acceptable salt thereof.

6. The compound according to claim 4, wherein $R_4$ is $CH_2R^a$, wherein $R^a$ is 1) phenyl,
2) mono- or di or tri-substituted phenyl wherein each substituent is independently selected from
   a) halo,
   b) hydroxy,
   c) $C_1$–$C_3$ alkoxy,
   d) $C_1$–$C_4$ alkyl, and
   e) $CF_3$,
3) heterocycle selected from pyridyl, pyrazinyl and pyrimidinyl, or
4) mono- or di- or tri-substituted heterocycle wherein heterocycle is selected from pyridyl, pyrazinyl and pyrimidinyl; and wherein each substituent is independently selected from
   a) halo,
   b) hydroxy,
   c) $C_1$–$C_3$ alkoxy,
   d) $C_1$–$C_4$ alkyl, and
   e) $CF_3$;

or a pharmaceutically acceptable salt thereof.

7. The compound according to claim 6, selected from group consisting of (αS, γR)-γ-[[((3S,4S)-3,4-dihydro-3-hydroxy-2H-1-benzopyran-4-yl)amino]carbonyl]-α-hydroxy-N-[1-[[[(2-methylphenyl)methyl]amino]carbonyl]cyclopentyl]benzene pentanamide;

(αS, γR)-γ-[[(3S,4S)-3,4-dihydro-3-hydroxy-2H-1-benzopyran-4-yl)amino]carbonyl]-α-hydroxy-N-[1,1-dimethyl-2-[[(2-methylphenyl)methyl]amino]-2-oxoethyl]benzenepentanamide;

and pharmaceutically acceptable salts thereof.

8. A compound of formula:

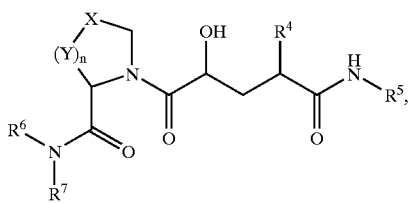

wherein X is
1) $S(O)_p$ wherein p is an integer equal to 0,1, or 2
2) O, or
3) $CR^bR^c$, wherein $R^b$ and $R^c$ are each independently
   a) hydrogen,
   b) hydroxy,
   c) halo,
   d) $C_1–C_4$ alkyl,
   e) $C_1–C_3$ alkoxy,
   f) aryl, or
   g) heterocycle;
Y is $CR^dR^e$, wherein $R^d$ and $R^e$ are each independently
   a) hydrogen,
   b) halo, or
   b) $C_1–C_4$ alkyl;
$R^4$ is $(CH_2)_mR^a$, wherein m is an integer from zero to 3 and $R^a$ is
1) hydrogen,
2) $C_1–C_6$ alkyl,
3) substituted $C_1–C_6$ alkyl wherein each substituent is independently selected from
   a) halo,
   b) hydroxy, and
   c) $C_1–C_3$ alkoxy,
4) aryl,
5) substituted aryl wherein each substituent is independently selected from
   a) halo,
   b) hydroxy,
   c) $C_1–C_3$ alkoxy,
   d) $C_1–C_4$ alkyl,
   e) fluorinated $C_1–C_4$ alkyl,
   f) aryl,
   g) substituted aryl wherein each substituent is independently selected from halo, hydroxy $C_1–C_4$ alkyl, and fluorinated $C_1–C_4$ alkyl,
   h) heterocycle, and
   i) substituted heterocycle wherein each substituent is independently selected from halo, hydroxy, $C_1–C_4$ alkyl, and fluorinated $C_1–C_4$ alkyl,
6) heterocycle, or
7) substituted heterocycle wherein each substituent is independently selected from
   a) halo,
   b) hydroxy,
   c) $C_1–C_3$ alkoxy,
   d) $C_1–C_4$ alkyl,
   e) fluorinated $C_1–C_4$ alkyl,
   f) aryl,
   g) substituted aryl wherein each substituent is independently selected from halo, hydroxy, $C_1–C_4$ alkyl, and fluorinated $C_1–C_4$ alkyl,
   h) heterocycle, and
   i) substituted heterocycle wherein each substituent is independently selected from halo, hydroxy, $C_1–C_4$ alkyl, and fluorinated $C_1–C_4$ alkyl;

$R^5$ is chroman, thiochroman, indanyl, dioxoisothiochroman, cyclopentyl, substituted chroman, substituted thiochroman, substituted indanyl, substituted, dioxothiochroman, or substituted cyclopentyl; wherein each of the substituents on substituted chroman, thiochroman, indanyl, dioxoisothiochroman, or cyclopentyl is independently selected from halogen, cyano, hydroxy, $C_1–C_6$ alkyl, fluorinated $C_1–C_6$ alkyl, $C_1–C_4$ alkoxy, or fluorinated $C_1–C_4$ alkoxy; and
$R^6$ and $R^7$ are each independently
1) hydrogen,
2) $C_1–C_6$ alkyl, or
3) substituted $C_1–C_6$ alkyl wherein each substituent is independently selected from
   a) halo,
   b) hydroxy,
   c) aryl,
   d) substituted aryl, wherein each substituent is independently selected from halo, hydroxy, $C_1–C_4$ alkyl, fluorinated $C_1–C_4$ alkyl, and aryl,
   e) heterocycle, and
   f) substituted heterocycle wherein each substituent is independently selected from halo, hydroxy, $C_1–C_4$ alkyl, fluorinated $C_1–C_4$ alkyl, and aryl,
or
$R^6$ and $R^7$ together with the nitrogen to which they are attached from $C_3–C_6$ azacycloalkyl which is optionally substituted with one or more substituents independently selected from
1) halo,
2) hydroxy,
3) $C_1–C_6$ alkyl,
4) $C_1–C_3$ alkoxy,
5) aryl,
6) substituted aryl wherein each substituent is independently selected from
   a) halo,
   b) hydroxy,
   c) $C_1–C_3$ alkoxy,
   d) $C_1–C_4$ alkyl, and
   e) fluorinated $C_1–C_4$ alkyl
7) heterocycle, and
8) substituted heterocycle wherein each substituent is independently selected from
   a) halo,
   b) hydroxy,
   c) $C_1–C_3$ alkoxy,
   d) $C_1–C_4$ alkyl, and
   e) fluorinated $C_1–C_4$ alkyl;
and
n is an integer equal to 0, 1, or 2;
or a pharmaceutically acceptable salt thereof.

9. The compound according to claim 8, wherein
$R^4$ is $(CH_2)_mR^a$, wherein m is an integer from zero to 3 and $R^a$ is
1) hydrogen,
2) $C_1–C_4$ alkyl,
3) substituted $C_1–C_4$ alkyl wherein each substituent is independently selected from
   a) halo,
   b) hydroxy, and
   c) $C_1–C_3$ alkoxy,
4) phenyl,
5) mono- or di- or tri substituted phenyl wherein each substituent is independently selected from a) halo,
b) hydroxy,
c) $C_1$–$C_3$ alkoxy,
d) $C_1$–$C_4$ alkyl,
e) $(CH_2)_{0-3}CF_3$,
f) phenyl,
g) mono- or di- or tri-substituted phenyl, wherein each substituent is independently selected from halo, hydroxy, $C_1$–$C_4$ alkyl, and $(CH_2)_{0-3}CF_3$,
h) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and
i) mono- or di- or tri-substituted heterocycle, wherein heterocycle is selected from pyrrolidinyl, piperidinyl, piperazinyl, imidazolindinyl, pyrrolyl, pyridyl, pyrazinyl, pyrimidinyl, pyridazinyl, imidazolyl, oxazolyl, thiazolyl, pyrazolyl, triazolyl, and tetrazolyl, and wherein each substituent is independently selected from halo, hydroxy, $C_1$–$C_4$ alkyl, and $(CH_{20})_{0-3}CF_3$;
6) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, tetrazolyl, and furopyridyl, or
7) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, tetrazolyl, and furopyridyl, and wherein each substituent is independently selected from
a) halo,
b) hydroxy,
c) $C_1$–$C_3$ alkoxy,
d) $C_1$–$C_4$ alkyl,
e) $(CH_2)_{0-3}CF_3$,
f) phenyl,
g) mono- or di- or tri-substituted phenyl wherein each substituent is independently selected from halo, hydroxy, $C_1$–$C_4$ alkyl, and $(CH_2)_{0-3}CF_3$,
h) heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and
i) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and wherein each substituent is independently selected from halo, hydroxy, $C_1$–$C_4$ alkyl, and $(CH_2)_{0-3}CF_3$;

$R^5$ is chroman, thiochroman, indanyl, dioxoisothiochroman, cyclopentyl, substituted chroman, substituted thiochroman, substituted indanyl, substituted dioxothiochroman, or substituted cyclopentyl; wherein each of the substituents on substituted chroman, thiochroman, indanyl, dioxoisothiochroman, or cyclopentyl is independently selected from halogen, cyano, hydroxy, $C_1$–$C_4$ alkyl, $(CH_2)_{0-3}CF_3$, $C_1$–$C_4$ alkoxy, or $(CH_2)_{0-3}OCF_3$; and $R^6$ and $R^7$ are each independently
1) hydrogen,
2) $C_1$–$C_4$ alkyl, or
3) substituted $C_1$–$C_4$ alkyl wherein each substituent is independently selected from
a) halo,
b) hydroxy,
c) phenyl, and
d) mono- or di- or tri-substituted phenyl, wherein each substituent is independently selected from halo, hydroxy, $C_1$–$C_4$ alkyl, and $(CH_2)_{0-3}CF_3$,
e) heterocycle selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyl, pyrazolyl, triazolyl, and tetrazolyl, and
f) mono- or di- or tri-substituted heterocycle wherein heterocycle is selected from pyrrolidinyl, piperidinyl, piperazinyl, imidazolidinyl, pyrrolyl, pyridyl, pyrazinyl, pyrimidinyl, pyridazinyl, imidazolyl, oxazolyl, thiazolyol, pyrazolyl, triazolyl, and tetrazolyl, and wherein each substituent is independently selected from halo, hydroxy, $C_1$–$C_4$ alkyl, and $(CH_2)_{0-3}CF_3$;

or
$R^6$ and $R^7$ together with the nitrogen to which they are attached form $C_3$–$C_6$ azacycloalkyl which is optionally substituted with one or more substituents independently selected from
1) halo
2) hydroxy
3) $C_1$–$C_4$ alkyl, and
4) $C_1$–$C_3$ alkoxy;
or a pharmaceutically acceptable salt thereof.

10. The compound according to claim 9, wherein the compound is of formula:

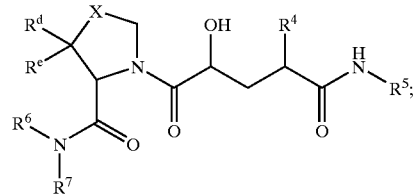

wherein
X is S, O or $CR^bR^c$, wherein $R^b$ and $R^c$ are each independently hydrogen, hydroxy, halo, or $C_1$–$C_3$ alkoxy;
or a pharmaceutically acceptable salt thereof.

11. The compound according to claim 10, wherein
$R^5$ is chroman, indanyl, cyclopentyl, substituted chroman, substituted indanyl, or substituted cyclopentyl;
or a pharmaceutically acceptable salt thereof.

12. The compound according to claim 11, wherein
$R^a$ is
1) $C_1$–$C_4$ alkyl,
2) substituted $C_1$–$C_4$ alkyl wherein each substituent is independently selected from
a) halo,
b) hydroxy, and
c) $C_1$–$C_3$ alkoxy,
3) phenyl,
4) mono- or di- or tri-substituted phenyl wherein each substituent is independently selected from a) halo,
b) hydroxy,
c) $C_1-C_3$ alkoxy,
d) $C_1-C_4$ alkyl,
e) $CF_3$,
f) phenyl,
g) mono- di- or tri-substituted phenyl, wherein each substituent is independently selected from halo, hydroxy, $C_1-C_4$ alkyl, and $CF_3$,
h) heterocycle selected from pyridyl, pyrazinyl and pyrimidinyl, and
i) mono- or di- or tri-substituted heterocycle, wherein heterocycle is selected from pyridyl, pyrazinyl, and pyrimidinyl, and wherein each substituent is independently selected from halo, hydroxy, $C_1-C_4$ alkyl, and $CF_3$;
5) heterocycle selected from pyridyl, pyrazinyl, pyrimidinyl, oxazolyl, thiazolyl, and furopyridyl, or
6) mono- or di- or tri-substituted heterocycle wherein heterocycle is selected from pyridyl, pyrazinyl, pyrimidinyl, oxazolyl, thiazolyl, and furopyridyl; and wherein each substituent is independently selected from
a) halo,
b) hydroxy,
c) $C_1-C_3$ alkoxy,
d) $C_1-C_4$ alkyl,
e) $CF_3$,
f) phenyl,
g) mono- or di- or tri-substituted phenyl wherein each substituent is independently selected from cyano, halo, hydroxy, $C_1-C_4$ alkyl, and $CF_3$,
h) heterocycle selected from pyridyl, pyrazinyl and pyrimidinyl, and
i) mono- or di- or tri-substituted heterocycle wherein heterocycle is selected from pyridyl, pyrazinyl and pyrimidinyl, and wherein each substituent is independently selected from cyano, halo, hydroxy, $C_1-C_4$ alkyl, and $CF_3$; and $R^6$ and $R^7$ are each independently
1) hydrogen,
2) $C_1-C_4$ alkyl, or
3) substituted $C_1-C_4$ alkyl wherein each substituent is independently selected from
a) halo,
b) hydroxy,
c) phenyl,
d) mono- or di- or tri-substituted phenyl, wherein each substituent is independently selected from halo, hydroxy, $C_1-C_4$ alkyl, and $CF_3$,
e) heterocycle selected from pyridyl, pyrazinyl and pyrimidinyl, and
f) mono- or di- or tri-substituted heterocycle wherein heterocycle is selected from pyridyl, pyrazinyl and pyrimidinyl, and wherein each substituent is independently selected from halo, hydroxy, $C_1-C_4$ alkyl, and $(CH_2)_{0-3}CF_3$;

or a pharmaceutically acceptable salt thereof.

13. The compound according to claim 12, wherein $R^4$ is $CH_2R^a$, wherein $R^a$ is
1) phenyl,
2) mono- or di- or tri-substituted phenyl wherein each substituent is independently selected from
a) halo,
b) hydroxy,
c) $C_1-C_3$ alkoxy,
d) $C_1-C_4$ alkyl, and
e) $CF_3$,
3) heterocycle selected from pyridyl, pyrazinyl, pyrimidinyl, oxazolyl, thiazolyl, and furopyridyl, or
4) mono- or di- or tri-substituted heterocycle wherein heterocycle is selected from pyridyl, pyrazinyl, pyrimidinyl, oxazolyl, thiazolyl, and furopyridyl; and wherein each substituent is independently selected from
a) halo,
b) hydroxy,
c) $C_1-C_3$ alkoxy,
d) $C_1-C_4$ alkyl, and
e) $CF_3$;

or a pharmaceutically acceptable salt thereof.

14. The compound according to claim 13, wherein
X is S or $CR^bR^c$;
or a pharmaceutically acceptable salt thereof.

15. The compound according to claim 13, selected from the group consisting of (4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[2-methylphenyl)methyl]-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(2,2,2-trifluoroethyl)-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmentyl)pentyl]-5,5-dimethyl-N-(1,1-dimethyl)-4-thiazolidinecarboxamide;

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl]-5,5-dimethyl-N-(2,2,2-trifluoroethyl)-4-thiazolidinecarboxamide;

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl]-5,5-dimethyl-N-(1,1-dimethylethyl)-4-thiazolidinecarboxaimide;

(4R)-3-[(2S,4R)-5-[((1S,2R)-2,3-dihydro-2-hydroxy-1H-inden-1-yl)amino]-2-hydroxy-1,5-dioxo-4-(phenylmethyl)pentyl]-5,5-dimethyl-N-[(2-methylphenyl)-methyl]-4-thiazolidinecarboxamide;

(2S)-1-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-N-[(2-methylphenyl)-methyl]-2-pyrrolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(4-pyridinylmethyl)-4-thiazolidinecarboxamide;

(2S)-1-[(2S,4R)-5-[((1S,2R)-2,3-dihydro-2-hydroxy-1H-iden-1-yl)amino]-2-hydroxy-1,5-dioxo-4-(phenylmethyl)pentyl]-N-[(2-methylphenyl)methyl]-2-pyrrolidinecarboxamide;

(4R)-3-[(2S,4R)-5-[((1S,2R)-2,3-dihydro-2-hydroxy-1H-iden-1-yl)amino]-2-hydroxy-1,5-dioxo-4-(phenylmethyl)pentyl]-5,5-dimethyl-N-(3-pyridinylmethyl)-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-(2-phenylethyl)-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(3-pyridinylmethyl)pentyl]-5,5-dimethyl-N-[(2-methylphenyl)methyl]-4-thiazolidinecarboxamide;

(4R)-3-[(2S,4)-5-[((1S,2R,5R)-5-methyl-2-hydroxy-1-cyclopentyl)amino]-2-hydroxy-1,5-dioxo-4-(phenylmethyl)pentyl]-5,5-dimethyl-N-[(2-methylphenyl)-methyl]-4-thiazolidinecarboxamide;

(2S,4S)-1-[(2S,4)-5-[((1S,2R)-2,3-dihydro-2-hydroxy-1H-inden-1-yl)amino]-2-hydroxy-1,5-dioxo-4-(phenylmethyl)pentyl]-N-[(2-methylphenyl)methyl]-4-chloro-2-pyrrolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-3,3-dimethyl-N-[(2,6-dimethylphenyl)-methyl]-2-pyrrolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-3,3-dimethyl-N-[(3-methyl-2-pyridylmethyl)]-2-pyrrolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2,6-dimethylphenyl)methyl]-4-oxazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2,6-dimethylphenyl)methyl]-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(3-methyl-2-pyridinylmethyl)]-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(3,5-dimethyl-4-isoxazolemethyl)]-4-thiazolidinecarboxamide;

(4R)-3-[(2S,4R)-5-[((3S,4S)-3,4-dihydro-3-hydroxy-2H-1-benzopyran-4-yl)amino]-2-hydroxy-1,5-dioxo-4-(phenylmethyl)pentyl]-5,5-dimethyl-N-[(2,6-dimethylphenyl)methyl]-4-thiazolidinecarboxamide-1,1-dioxide;

(4R)-N-[(2-chloro-6-methylphenyl)methyl]-3-[(2S,4S)-5-[((3S,4S)-3,4-dihydro-3-hydroxy-2H-1-benzopyran-4-yl)amino]-4-furo[2,3-c]pyridin-2-ylmethyl)-2-hydroxy-1,5-dioxopentyl]-5,5-dimethyl-4-thiazolidinecarboxamide;

(4R)-N-[(2-chloro-6-methylphenyl)methyl]-3-[(2S,4S)-5-[((3S,4S)-3,4-dihydro-3-hydroxy-2H-1-benzopyran-4-yl)amino]-2-hydroxy-4-(5-oxazolylmethyl)-1,5-dioxopentyl]-5,5-dimethyl-4-thiazolidinecarboxamide;

and pharmaceutically acceptable salts thereof.

16. A pharmaceutical composition comprising a therapeutically effective amount of a compound according to claim 1 and a pharmaceutically acceptable carrier; wherein the therapeutically effective amount is an amount effective to inhibit HIV protease, treat or prevent HIV infection, or treat AIDS.

17. A pharmaceutical composition made by combining a therapeutically effective amount of a compound according to claim 1 and a pharmaceutically acceptable carrier; wherein the therapeutically effective amount is an amount effective to inhibit HIV protease, treat or prevent HIV infection, or to treat AIDS.

18. The pharmaceutical composition according to claim 16, wherein the composition further comprises a therapeutically effective amount of at least one HIV infections/AIDS treatment agent selected from the group consisting of HIV/AIDS antiviral agents, immunomodulators, and anti-infective agents.

19. The pharmaceutical composition according to claim 16, wherein the composition further comprises a therapeutically effective amount of at least one antiviral selected from the group consisting of non-nucleoside HIV reverse transcriptase inhibitors and nucleoside HIV reverse transcriptase inhibitors.

20. The pharmaceutical composition according to claim 19, further comprising a therapeutically effective amount of an additional HIV protease inhibitor.

21. A method of inhibiting HIV protease in a subject in need thereof which comprises administering to the subject a therapeutically effective amount of the compound according to claim 1.

22. A method of preventing or treating infection by HIV in a subject in need thereof which comprises administering to the subject a therapeutically effective amount of the compound according to claim 1.

23. The method according to claim 22, wherein the compound is administered in combination with a therapeutically effective amount of at least one HIV infection/AIDS treatment agent selected from the group consisting of HIV/AIDS antiviral agents, immunomodulators, and anti-infective agents.

24. The method according to claim 22, wherein the compound is administered in combination with a therapeutically effective amount of at least one antiviral selected from the group consisting of non-nucleoside HIV reverse transcriptase inhibitors and nucleoside HIV reverse transcriptase inhibitors.

25. A method of treating AIDS in a subject in need thereof which comprises administering to the subject a therapeutically effective amount of the compound according to claim 1.

26. The method according to claim 25, wherein the compound is administered in combination with a therapeutically effective amount of at least one HIV infection/AIDS treatment agent selected from the group consisting of HIV/AIDS antiviral agents, immunomodulators, and anti-infective agents.

27. The method according to claim 25, wherein the compound is administered in combination with a therapeutically effective amount of at least one antiviral selected from the group consisting of non-nucleoside HIV reverse transcriptase inhibitors and nucleoside HIV reverse transcriptase inhibitors.

28. A method of inhibiting HIV protease in a subject in need thereof which comprises administering to the subject a therapeutically effective amount of the composition according to claim 16.

29. A method of preventing or treating infection by HIV in a subject in need thereof which comprises administering to the subject a therapeutically effective amount of the composition according to claim 16.

30. A method of preventing or treating infection by HIV in a subject in need thereof which comprises administering to the subject a therapeutically effective amount of the composition according to claim 17.

31. A method of preventing or treating HIV infection in a subject in need thereof which comprises administering to the subject a therapeutically effective amount of the composition according to claim 18.

32. A method of preventing or treating HIV infection in a subject in need thereof which comprises administering to the subject a therapeutically effective amount of the composition according to claim 19.

33. A method of treating AIDS in a subject in need thereof which comprises administering to the subject a therapeutically effective amount of the composition according to claim 16.

34. A method of treating AIDS in a subject in need thereof which comprises administering to the subject a therapeutically effective amount of the composition according to claim 17.

35. A method of treating AIDS in a subject in need thereof which comprises administering to the subject a therapeutically effective amount of the composition according to claim 18.

36. A method of treating AIDS in a subject in need thereof which comprises administering to the subject a therapeutically effective amount of the composition according to claim 19.

37. A pharmaceutical composition comprising a therapeutically effective amount of a compound according to claim 8 and a pharmaceutically acceptable carrier wherein the therapeutically effective amount is an amount effective to inhibit HIV protease, treat or prevent HIV infection, or to treat AIDS.

38. A pharmaceutical composition made by combining a therapeutically effective amount of a compound according to claim 8 and a pharmaceutically acceptable carrier; wherein the therapeutically effective amount is an amount effective to inhibit HIV protease, treat or prevent HIV infection, or to treat AIDS.

39. A method of inhibiting HIV protease in a subject in need thereof which comprises administering to the subject a therapeutically effective amount of the compound according to claim 8.

40. A method of preventing or treating infection by HIV in a subject in need thereof which comprises administering to the subject a therapeutically effective amount of the compound according to claim 8.

41. A method of treating AIDS in a subject in need thereof which comprises administering to the subject a therapeutically effective amount of the compound according to claim 8.

42. A method of preventing or treating infection by HIV in a subject in need thereof which comprises administering to the subject a therapeutically effective amount of the composition according to claim 37.

43. A method of preventing or treating infection by HIV in a subject in need thereof which comprises administering to the subject a therapeutically effective amount of the composition according to claim 38.

44. A method of treating AIDS in a subject in need thereof which comprises administering to the subject a therapeutically effective amount of the composition according to claim 37.

45. A method of treating AIDS in a subject in need thereof which comprises administering to the subject a therapeutically effective amount of the composition according to claim 38.

* * * * *